United States Patent
Maus et al.

(10) Patent No.: US 11,613,574 B2
(45) Date of Patent: Mar. 28, 2023

(54) METHODS AND COMPOSITIONS RELATING TO EX VIVO CULTURE AND MODULATION OF T CELLS

(71) Applicant: The General Hospital Corporation, Boston, MA (US)

(72) Inventors: Marcela V. Maus, Lexington, MA (US); Felipe Bedoya, Medford, MA (US)

(73) Assignee: The General Hospital Corporation, Boston, MA (US)

( * ) Notice: Subject to any disclaimer, the term of this patent is extended or adjusted under 35 U.S.C. 154(b) by 544 days.

(21) Appl. No.: 16/476,592

(22) PCT Filed: Jan. 10, 2018

(86) PCT No.: PCT/US2018/013215
§ 371 (c)(1),
(2) Date: Jul. 9, 2019

(87) PCT Pub. No.: WO2018/132508
PCT Pub. Date: Jul. 19, 2018

(65) Prior Publication Data
US 2019/0330343 A1     Oct. 31, 2019

Related U.S. Application Data

(60) Provisional application No. 62/580,256, filed on Nov. 1, 2017, provisional application No. 62/485,679, filed on Apr. 14, 2017, provisional application No. 62/444,608, filed on Jan. 10, 2017.

(51) Int. Cl.
| | | |
|---|---|---|
| *C07K 16/28* | (2006.01) | |
| *A61P 35/02* | (2006.01) | |
| *A61P 35/00* | (2006.01) | |
| *A61K 35/17* | (2015.01) | |
| *C07K 14/725* | (2006.01) | |
| *C07K 14/705* | (2006.01) | |
| *C12N 5/0783* | (2010.01) | |

(52) U.S. Cl.
CPC .......... *C07K 16/2809* (2013.01); *A61K 35/17* (2013.01); *A61P 35/00* (2018.01); *A61P 35/02* (2018.01); *C07K 14/7051* (2013.01); *C07K 14/70517* (2013.01); *C07K 16/2803* (2013.01); *C07K 16/2818* (2013.01); *C07K 16/2875* (2013.01); *C07K 16/2878* (2013.01); *C12N 5/0636* (2013.01); *C07K 2317/622* (2013.01); *C07K 2319/02* (2013.01); *C07K 2319/03* (2013.01); *C07K 2319/30* (2013.01); *C07K 2319/33* (2013.01); *C12N 2510/00* (2013.01)

(58) Field of Classification Search
None
See application file for complete search history.

(56) References Cited

U.S. PATENT DOCUMENTS

2014/0212446 A1   7/2014   Riley et al.
2016/0340406 A1   11/2016  Zhao et al.

FOREIGN PATENT DOCUMENTS

WO   WO-2016/069282 A1   5/2016
WO   WO 2018/132508 A1   7/2018

OTHER PUBLICATIONS

Leitner et al. (Journal of Immunological Methods 362 (2010) 131-141). (Year: 2010).*
Janeway et al., Immunobiology, 5th Ed., Garland Science, pp. 313-315, (2001). (Year: 2001).*
Pollock et al., J Immunol 1993; 150:771-781. (Year: 1993).*
International Search Report and Written Opinion for International Application No. PCT/US18/13215, dated May 8, 2018 (20 pages).
International Preliminary Report on Patentability for International Application No. PCT/US2018/013215, dated Jul. 16, 2019 (9 pages).
Otahal et al., "Release of Vesicular Stomatitis Virus Spike Protein G-Pseudotyped Lentivirus from the Host Cell Is Impaired upon Low-Density Lipoprotein Receptor Overexpression," J Virol. 89(22):11723-6 (2015).

* cited by examiner

Primary Examiner — Zachary S Skelding
(74) Attorney, Agent, or Firm — Wolf, Greenfield & Sacks, P.C.

(57) ABSTRACT

Described herein are methods for producing and utilizing an artificial antigen presenting cell (aAPC). An aAPC is engineered to express a first and second chimeric stimulatory receptor that specifically bind antigen presenting on a T cell of interest. The aAPC as described herein is designed for use in activating and/or expanding a T cell or chimeric antigen receptor (CAR) T cell. Further, this invention relates to methods of treating cancer by administering to a subject in need thereof an aAPC-activated CART cell.

17 Claims, 15 Drawing Sheets

Specification includes a Sequence Listing.

T7E1 Data
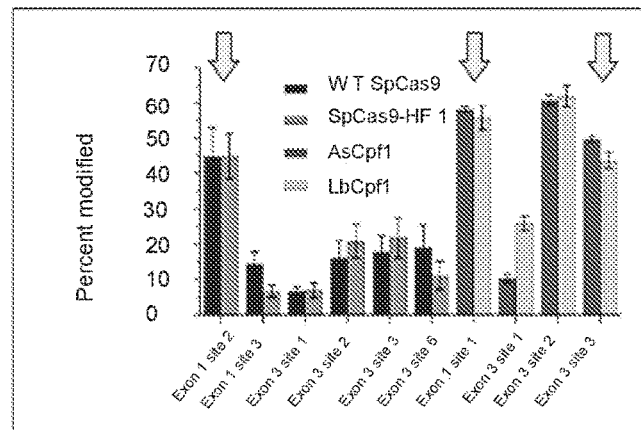
FACS Data
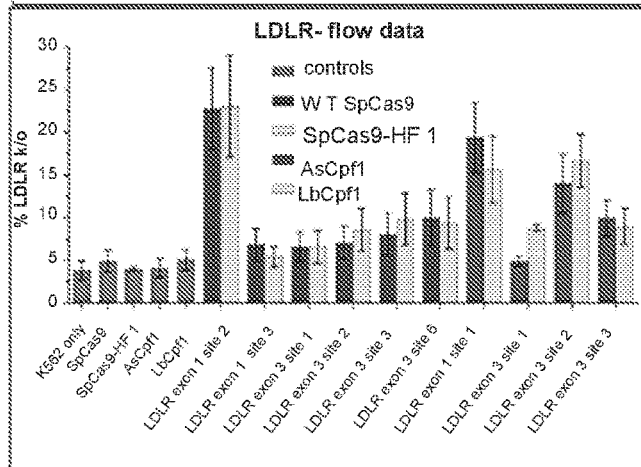
FIG. 9

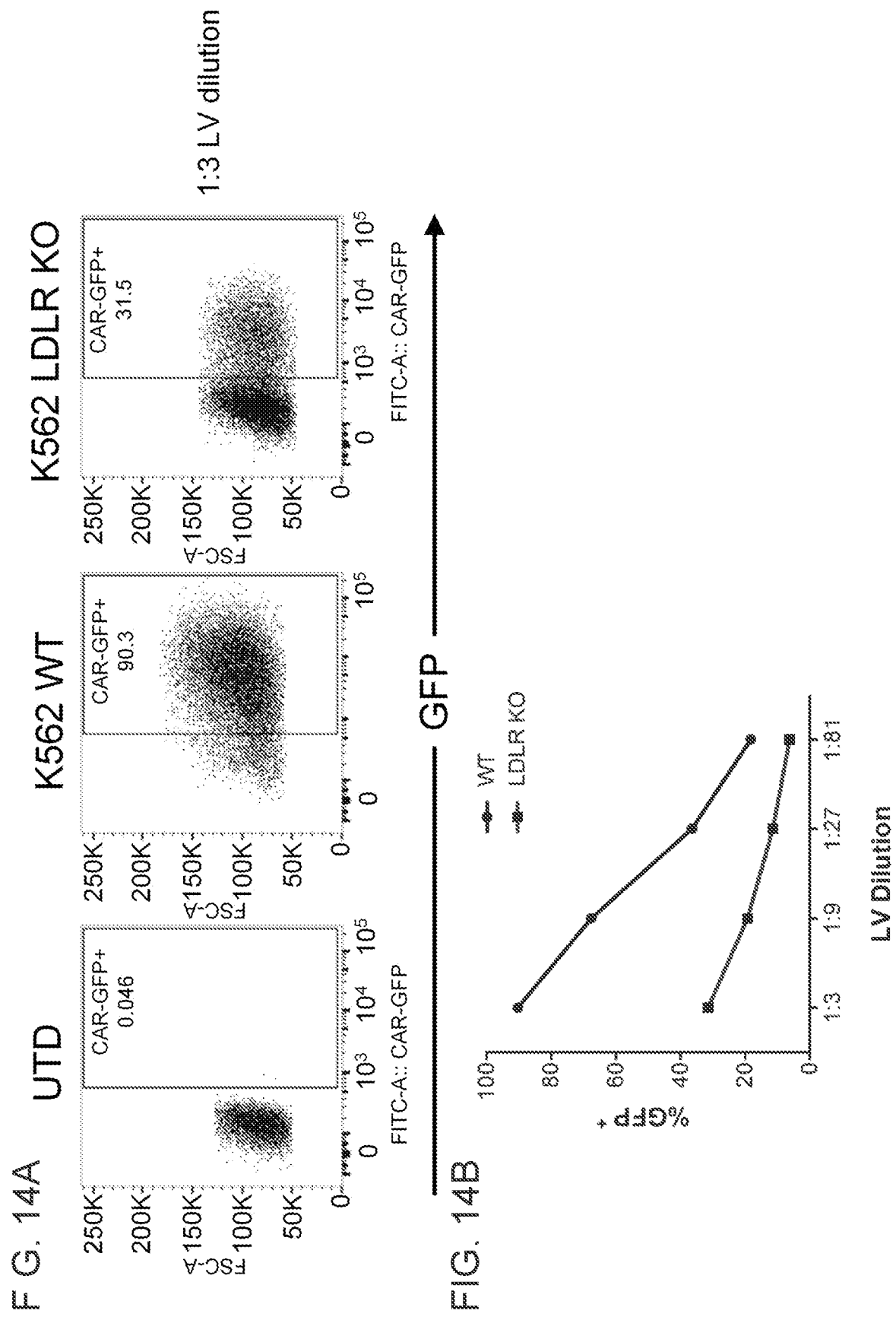

METHODS AND COMPOSITIONS RELATING TO EX VIVO CULTURE AND MODULATION OF T CELLS

CROSS-REFERENCE TO RELATED APPLICATIONS

This application claims benefit under 35 U.S.C. § 119(e) of U.S. Provisional Application Nos. 62/444,608, filed Jan. 10, 2017, 62/485,679, filed Apr. 14, 2017, and 62/580,256, filed Nov. 1, 2017, the contents of which are incorporated herein by reference in their entirety.

SEQUENCE LISTING

The instant application contains a Sequence Listing which has been submitted electronically in ASCII format and is hereby incorporated by reference in its entirety. Said ASCII copy, created Jun. 18, 2019, is named 51295-003004_Sequence_Listing_06.18.19_ST25 and is 48,615 bytes in size.

TECHNICAL FIELD

The technology described herein relates to cancer immunotherapies.

BACKGROUND

T cell therapies targeting tumor antigens have shown unprecedented complete remissions in patients with refractory and relapsing cancers in the past few years. The clinical doses of these T cell products are commonly achieved through the expansion of naive T cells by stimulation with paramagnetic microspheres, which are covalently bound to antibodies crosslinking key molecules signaling T cell growth, namely CD3 and CD28. Improved methods bearing the features required to generate and expand tumor-targeting T cells ex vivo for clinical use are needed.

SUMMARY

Provided herein are methods for producing an artificial antigen presenting cell (aAPC) and utilizing the aAPC for the activation of a T cell, including, but not limited to a chimeric antigen receptor (CAR) T cell. Additionally provided herein, are methods for the treatment of a plasma cell disease or disorder, or an autoimmune disease or disorder by administering an activated T cell or CAR T cell to a subject in need thereof.

Accordingly, in one aspect, described herein is an artificial antigen presenting cell (aAPC) comprising a first chimeric stimulatory receptor (CSR) that binds specifically with a first co-stimulatory peptide or polypeptide region, and a second CSR that binds specifically with a second co-stimulatory peptide or polypeptide region.

Another aspect described herein relates to an aAPC comprising a first chimeric stimulatory receptor (CSR) that binds specifically with CD3, and a second CSR that binds specifically with CD28.

As used herein, "chimeric stimulatory receptor" refers to a polypeptide comprising, from N-terminus to C-terminus an antibody reagent or a natural ligand specific for a T cell activating receptor (e.g. CD3 or CD28); a linker domain; and a transmembrane domain.

In some embodiments of any of the aspects, the aAPC has been engineered to lack an expressible LDLR gene. In some embodiments of any of the aspects, the aAPC comprises a deletion in the native LDLR-encoding nucleic acid sequence. In other embodiments of any of the aspects, the aAPC comprises a deletion of the native LDLR-encoding nucleic acid sequence.

In some embodiments of any of the aspects, the aAPC is viable but non-dividing.

In some embodiments of any of the aspects, the aAPC has been gamma-irradiated.

In some embodiments of any of the aspects, the aAPC is further engineered to comprise a T-cell target molecule. In some embodiments of any of the aspects, the T-cell target molecule is CD19, BCMA, CD37, SLAMF7, EGFR, or EGFR variant III. In some embodiments of any of the aspects, the T-cell target molecule is CD19. In some embodiments of any of the aspects, the T-cell target molecule is any molecule that can be targeted by a CAR T cell.

In some embodiments of any of the aspects, the first and second CSRs are expressed on the cell surface of the aAPC.

In some embodiments of any of the aspects, the first and second CSRs are constitutively expressed.

In some embodiments of any of the aspects, the first and second CSRs are encoded by a first recombinant nucleic acid sequence and a second recombinant nucleic acid sequence, respectively. In some embodiments of any of the aspects, the sequence encoding the first and/or second CSR is operatively linked to a constitutive promoter. In some embodiments of any of the aspects, the constitutive promoter is an EF1-α promoter. Non-limiting examples of additional constitutive promoters include the MND promoter and the PGK promoter.

In some embodiments of any of the aspects, the aAPC is a human cell.

In some embodiments of any of the aspects, aAPC is engineered from an erythromyeloid cell. In some embodiments of any of the aspects, the erthromyeloid cell is a K562 cell.

In some embodiments of any of the aspects, the first and second CSRs bind specifically with human CD3 and CD28, respectively.

In some embodiments of any of the aspects, the first CSR binds specifically with 4-1BBL, and the second CSR binds specifically with OX40L.

Another aspect of the technology described herein relates to a method of expanding and/or activating a T cell, the method comprising contacting an aAPC as described herein with a T cell.

Another aspect of the technology described herein relates to a method of treating a cancer, a plasma cell disease or disorder, or an autoimmune disease or disorder in a subject in need thereof, the method comprising contacting an aAPC as described herein with a CAR T cell, thereby activating the CAR T cell, and administering the activated CAR T cell to the subject.

In some embodiments, the contacting step occurs in vitro. In some embodiments, the contacting step occurs in suspension.

In some embodiments, the cancer is a leukemia, lymphoma, multiple myeloma, or solid tumor. In some embodiments, the leukemia is ALL or CLL. In some embodiments, the lymphoma is follicular lymphoma or diffuse large B cell lymphoma.

Another aspect of the technology described herein relates to a composition comprising an aAPC as described herein and a T cell. In one embodiment, the T cell is a CAR T cell.

Another aspect of the technology described herein relates to a composition comprising activated CAR T cells described herein, and optionally a pharmaceutically acceptable carrier, for the treatment of cancer.

Definitions

For convenience, the meaning of some terms and phrases used in the specification, examples, and appended claims, are provided below. Unless stated otherwise, or implicit from context, the following terms and phrases include the meanings provided below. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs. If there is an apparent discrepancy between the usage of a term in the art and its definition provided herein, the definition provided within the specification shall prevail.

Definitions of common terms in immunology and molecular biology can be found in The Merck Manual of Diagnosis and Therapy, 19th Edition, published by Merck Sharp & Dohme Corp., 2011 (ISBN 978-O-911910-19-3); Robert S. Porter et al. (eds.), The Encyclopedia of Molecular Cell Biology and Molecular Medicine, published by Blackwell Science Ltd., 1999-2012 (ISBN 9783527600908); and Robert A. Meyers (ed.), Molecular Biology and Biotechnology: a Comprehensive Desk Reference, published by VCH Publishers, Inc., 1995 (ISBN 1-56081-569-8); Immunology by Werner Luttmann, published by Elsevier, 2006; Janeway's Immunobiology, Kenneth Murphy, Allan Mowat, Casey Weaver (eds.), Taylor & Francis Limited, 2014 (ISBN 0815345305, 9780815345305); Lewin's Genes XI, published by Jones & Bartlett Publishers, 2014 (ISBN-1449659055); Michael Richard Green and Joseph Sambrook, Molecular Cloning: A Laboratory Manual, $4^{th}$ ed., Cold Spring Harbor Laboratory Press, Cold Spring Harbor, N.Y., USA (2012) (ISBN 1936113414); Davis et al., Basic Methods in Molecular Biology, Elsevier Science Publishing, Inc., New York, USA (2012) (ISBN 044460149X); Laboratory Methods in Enzymology: DNA, Jon Lorsch (ed.) Elsevier, 2013 (ISBN 0124199542); Current Protocols in Molecular Biology (CPMB), Frederick M. Ausubel (ed.), John Wiley and Sons, 2014 (ISBN 047150338X, 9780471503385), Current Protocols in Protein Science (CPPS), John E. Coligan (ed.), John Wiley and Sons, Inc., 2005; and Current Protocols in Immunology (CPI) (John E. Coligan, ADA M Kruisbeek, David H Margulies, Ethan M Shevach, Warren Strobe, (eds.) John Wiley and Sons, Inc., 2003 (ISBN 0471142735, 9780471142737), the contents of which are all incorporated by reference herein in their entireties.

The terms "decrease," "reduced," "reduction," and "inhibit" are all used herein to mean a decrease by a statistically significant amount. In some embodiments, "reduce," "reduction" or "decrease" or "inhibit" typically means a decrease by at least 10% as compared to a reference level (e.g. the absence of a given treatment or agent) and can include, for example, a decrease by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, or more. As used herein, "reduction" or "inhibition" does not encompass a complete inhibition or reduction as compared to a reference level. "Complete inhibition" is a 100% inhibition as compared to a reference level. Where applicable, a decrease can be preferably down to a level accepted as within the range of normal for an individual without a given disorder.

The terms "increased," "increase," "enhance," and "activate" are all used herein to mean an increase by a statically significant amount. In some embodiments, the terms "increased", "increase", "enhance", or "activate" can mean an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level. In the context of a marker or symptom, an "increase" is a statistically significant increase in such level.

As used herein, a "subject" means a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. In some embodiments, the subject is a mammal, e.g., a primate, e.g., a human. The terms, "individual," "patient," and "subject" are used interchangeably herein.

Preferably, the subject is a mammal. The mammal can be a human, non-human primate, mouse, rat, dog, cat, horse, or cow, but is not limited to these examples. Mammals other than humans can be advantageously used as subjects that represent animal models of e.g., cancer. A subject can be male or female.

A subject can be one who has been previously diagnosed with or identified as suffering from or having a condition in need of treatment (e.g., ALL or another type of cancer) or one or more complications related to such a condition, and optionally, have already undergone treatment for the condition or the one or more complications related to the condition. Alternatively, a subject can also be one who has not been previously diagnosed as having such condition or related complications. For example, a subject can be one who exhibits one or more risk factors for the condition or one or more complications related to the condition or a subject who does not exhibit risk factors.

A "subject in need" of treatment for a particular condition can be a subject having that condition, diagnosed as having that condition, or at risk of developing that condition.

A "disease" is a state of health of an animal, for example a human, wherein the animal cannot maintain homeostasis, and wherein if the disease is not ameliorated, then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

The term "cancer" and its grammatical equivalents as used herein can refer to a hyperproliferation of cells whose unique trait—loss of normal cellular control—results in unregulated growth, lack of differentiation, local tissue invasion, and metastasis. With respect to the inventive methods, the cancer can be any cancer recognized by a skilled person. Cancer can include, but is not limited to, any of acute lymphocytic cancer, acute myeloid leukemia, alveolar rhabdomyosarcoma, bone cancer, brain cancer, breast cancer, cancer of the anus, anal canal, rectum, cancer of the eye, cancer of the intrahepatic bile duct, cancer of the joints, cancer of the neck, gallbladder, or pleura, cancer of the nose, nasal cavity, or middle ear, cancer of the oral cavity, cancer of the vulva, chronic lymphocytic leukemia, chronic myeloid cancer, colon cancer, esophageal cancer, cervical cancer, fibrosarcoma, gastrointestinal carcinoid tumor, Hodgkin lymphoma, hypopharynx cancer, kidney cancer, larynx cancer, liquid tumors, liver cancer, lung cancer, lymphoma, malignant mesothelioma, mastocytoma, melanoma, multiple myeloma, nasopharynx cancer, non-Hodgkin lymphoma, ovarian cancer, pancreatic cancer, peritoneum, omentum, and mesentery cancer, pharynx cancer, prostate cancer, skin cancer, small intestine cancer, soft tissue cancer, solid tumors, stomach cancer, testicular cancer, thyroid cancer, ureter cancer, and/or urinary bladder cancer. As used herein, the term "tumor" refers to an abnormal growth of cells or tissues, e.g., of malignant type or benign type.

An "autoimmune disease or disorder" is characterized by the inability of one's immune system to distinguish between a foreign cell and a healthy cell of one's own body. This results in one's immune system mounting a response to target one's healthy cells. Non-limiting examples of an autoimmune disease or disorder include rheumatoid arthritis, multiple sclerosis (MS), systemic lupus erythematosus, Graves' disease (overactive thyroid), Hashimoto's thyroiditis (underactive thyroid), celiac disease, Crohn's disease and ulcerative colitis, Guillain-Barre syndrome, primary biliary sclerosis/cirrhosis, sclerosing cholangitis, autoimmune hepatitis, Raynaud's phenomenon, scleroderma, Sjogren's syndrome, Goodpasture's syndrome, Wegener's granulomatosis, polymyalgia rheumatica, temporal arteritis/ giant cell arteritis, chronic fatigue syndrome CFS), psoriasis, autoimmune Addison's Disease, ankylosing spondylitis, Acute disseminated encephalomyelitis, antiphospholipid antibody syndrome, aplastic anemia, idiopathic thrombocytopenic purpura, Myasthenia gravis, opsoclonus myoclonus syndrome, optic neuritis, Ord's thyroiditis, pemphigus, pernicious anaemia, polyarthritis in dogs, Reiter's syndrome, Takayasu's arteritis, warm autoimmune hemolytic anemia, Wegener's granulomatosis and fibromyalgia (FM).

A plasma cell is a white blood cell produces from B lymphocytes which function to generate and release antibodies needed to fight infections. A "plasma cell disease or disorder" is characterized by abnormal multiplication of a plasma cell. Abnormal plasma cells are capable of "crowding out" healthy plasma cells, which results in a decreased capacity to fight a foreign object, such as a virus or bacterial cell. Non-limiting examples of plasma cell disorders include amyloidosis, Waldenstrom's macroglobulinemia, osteosclerotic myeloma (POEMS syndrome), Monoclonal gammopathy of unknown significance (MGUS), and plasma cell myeloma.

As used herein, the terms "tumor antigen" and "cancer antigen" are used interchangeably to refer to antigens which are differentially expressed by cancer cells and can thereby be exploited in order to target cancer cells. Cancer antigens are antigens which can potentially stimulate substantially tumor-specific immune responses. Some of these antigens are encoded, although not necessarily expressed, by normal cells. These antigens can be characterized as those which are normally silent (i.e., not expressed) in normal cells, those that are expressed only at certain stages of differentiation and those that are temporally expressed such as embryonic and fetal antigens found on or expressed by cancer cells. Other cancer antigens are encoded by mutant cellular genes, such as oncogenes (e.g., activated ras oncogene), suppressor genes (e.g., mutant p53), and fusion proteins resulting from internal deletions or chromosomal translocations. Still other cancer antigens can be encoded by viral genes such as those carried on RNA and DNA tumor viruses. Many tumor antigens have been defined in terms of multiple solid tumors: MAGE 1, 2, & 3, defined by immunity; MART-1/ Melan-A, gp100, carcinoembryonic antigen (CEA), HER2, mucins (i.e., MUC-1), prostate-specific antigen (PSA), and prostatic acid phosphatase (PAP). Tumor antigens readily targeted by T cells, such as CAR T cells, are generally expressed on the surface of a cancer cell.

As used herein, the term "chimeric" refers to the product of the fusion of portions of at least two or more different polynucleotide molecules. In one embodiment, the term "chimeric" refers to a gene expression element produced through the manipulation of known elements or other polynucleotide molecules In some embodiments, "activation" can refer to the state of a T cell that has been sufficiently stimulated to induce detectable cellular proliferation. In some embodiments activation can refer to induced cytokine production. In other embodiments, activation can refer to detectable effector functions. At a minimum, an "activated T cells" as used herein is a proliferative T cell. In one embodiment, an activated T cell can be assessed by its cell-surface molecule profile. Non-limiting examples of molecules expressed the surface of an activated T cell include CD25, 4-1BB, and HLA-DR. Activated T cells also secrete cytokines, including, but not limited to IL-2. Methods to identify these surface molecules and secreted cytokines are known in the art.

As used herein, the terms "specific binding," "binds specifically," and "specifically binds" refer to a physical interaction between two molecules, compounds, cells and/or particles wherein the first entity binds to the second, target entity with greater specificity and affinity than it binds to a third entity which is a non-target. In some embodiments, specific binding can refer to an affinity of the first entity for the second target, entity, which is at least 10 times, at least 50 times, at least 100 times, at least 500 times, at least 1000 times or more greater than the affinity for the third non-target entity under the same conditions. A reagent specific for a given target is one that exhibits specific binding for that target under the conditions of the assay being utilized. A non-limiting example includes an antibody or a ligand, which recognizes and binds with a cognate binding partner (for example, a stimulatory and/or costimulatory molecule present on a T cell) protein.

A "stimulatory ligand," as used herein, refers to a ligand that when present on an antigen presenting cell (e.g., an aAPC, a dendritic cell, a B-cell, and the like) can specifically bind with a cognate binding partner (referred to herein as a "stimulatory molecule" or "co-stimulatory molecule") on a T cell, thereby mediating a primary response by the T cell, including, but not limited to, proliferation, activation, initiation of an immune response, and the like. Stimulatory ligands are well-known in the art and encompass, inter alia, an MHC Class I molecule loaded with a peptide, an anti- CD3 antibody, a superagonist anti-CD28 antibody, and a superagonist anti-CD2 antibody.

A "stimulatory molecule," as the term is used herein, means a molecule on a T cell that specifically binds with a cognate stimulatory ligand present on an antigen presenting cell (including an aAPC as described herein).

"Co-stimulatory ligand," as the term is used herein, includes a molecule on an antigen presenting cell (e.g., an aAPC, dendritic cell, B cell, and the like) that specifically binds a cognate co-stimulatory molecule on a T cell, thereby providing a signal which, in addition to the primary signal provided by, for instance, binding of a TCR/CD3 complex with an MHC molecule loaded with peptide, mediates a T cell response, including, but not limited to, proliferation, activation, differentiation, and the like. A co-stimulatory ligand can include, but is not limited to, 4-1BBL, OX40L, CD7, B7-1 (CD80), B7-2 (CD86), PD-L1, PD-L2, inducible COStimulatory ligand (ICOS-L), intercellular adhesion molecule (ICAM), CD30L, CD40, CD70, CD83, HLA-G, MICA, MICB, HVEM, lymphotoxin beta receptor, 3/TR6, ILT3, ILT4, HVEM, an agonist or antibody that binds Toll-like receptor and a ligand that specifically binds with B7-H3. A co-stimulatory ligand also can include, but is not limited to, an antibody that specifically binds with a co-stimulatory molecule present on a T cell, such as, but not limited to, CD27, CD28, 4-1BB, OX40, CD30, CD40, PD-1, ICOS, lymphocyte function-associated antigen-1 (LFA-1), CD2, CD7, LIGHT, NKG2C, B7-H3, and a ligand that specifically binds with CD83.

A "co-stimulatory molecule" refers to the cognate binding partner on a T cell that specifically binds with a co-stimulatory ligand, thereby mediating a co-stimulatory response by the T cell, such as, but not limited to, proliferation. Co-stimulatory molecules include, but are not limited to an MHC class I molecule, BTLA, a Toll-like receptor, CD27, CD28, 4-1BB, OX40, CD30, CD40, PD-1, ICOS, lymphocyte function-associated antigen-1 (LFA-1), CD2, CD7, LIGHT, NKG2C, B7-H3, and CD83.

In one embodiment, the term "engineered" and its grammatical equivalents as used herein can refer to one or more human-designed alterations of a nucleic acid, e.g., the nucleic acid within an organism's genome. In another embodiment, engineered can refer to alterations, additions, and/or deletion of genes. An "engineered cell" can refer to a cell with an added, deleted and/or altered gene. The term "cell" or "engineered cell" and their grammatical equivalents as used herein can refer to a cell of human or non-human animal origin.

"Chimeric antigen receptor" or "CAR" or "CARs" as used herein refers to engineered receptors, which graft an antigen specificity onto cells (for example T cells such as naïve T cells, central memory T cells, effector memory T cells or combination thereof). CARs are also known as artificial T-cell receptors, chimeric T-cell receptors or chimeric immunoreceptors. In one embodiment, the CARs useful in the technology described herein comprise at least two antigen-specific targeting regions, an extracellular domain, a transmembrane domain, and an intracellular signaling domain. In such embodiments, the two or more antigen-specific targeting regions target at least two different antigens and may be arranged in tandem and separated by linker sequences. In another embodiment, the CAR is a bispecific CAR. A bispecific CAR is specific to two different antigens.

As used herein, a "CAR T cell" refers to a T cell which expresses a CAR. When expressed in a T cell, CARs have the ability to redirect T-cell specificity and reactivity toward a selected target in a non-MHC-restricted manner, exploiting the antigen-binding properties of monoclonal antibodies. The non-MHC-restricted antigen recognition gives T-cells expressing CARs the ability to recognize an antigen independent of antigen processing, thus bypassing a major mechanism of tumor escape.

In one embodiment, the CAR's extracellular binding domain is composed of a single chain Fv fragment (scFv) derived from fusing the variable heavy and light regions of a monoclonal antibody. Alternatively, scFvs may be used that are derived from Fab's (instead of from an antibody, e.g., obtained from Fab libraries), in various embodiments, this scFv is fused to a transmembrane domain and then to an intracellular signaling domain. "First-generation" CARs include those that solely provide CD3zeta (CD3ζ) signals upon antigen binding, "Second-generation" CARs include those that provide both costimulation (e.g., CD28 or CD 137) and activation (CD3ζ). "Third-generation" CARs include those that provide multiple costimulatory (e.g., CD28 and CD 137) domains and activation domains (e.g., CD3ζ). In various embodiments, the CAR is selected to have high affinity or avidity for the antigen. A more detailed description of CARs and CAR T cells can be found in Maus et al. Blood 2014 123:2624-35; Reardon et al. Neuro-Oncology 2014 16:1441-1458; Hoyos et al. Haematologica 2012 97:1622; Byrd et al. J Clin Oncol 2014 32:3039-47; Maher et al. Cancer Res 2009 69:4559-4562; and Tamada et al. Clin Cancer Res 2012 18:6436-6445; each of which is incorporated by reference herein in its entirety.

An "antigen presenting cell" (APC) is a cell that is capable of activating T cells by presenting an antigen and necessary co-stimulatory ligand to promote T cell activation, and includes, but is not limited to, monocytes/macrophages, B cells and dendritic cells. As used herein, "artificial" refers to something made or produced, rather than occurring naturally. As used herein, "artificial antigen presenting cell" (aAPC) refers to a cell which has been engineered to copy or mimic at least one function of a naturally occurring APC. In one embodiment, the aAPC can at least stimulate proliferation of a T cell or CAR T cell. In another embodiment, the aAPC can stimulate proliferation and/or activation of a T cell or CAR T cell.

As used herein, the term "operably linked" refers to a first polynucleotide molecule, such as a promoter, connected with a second transcribable polynucleotide molecule, such as a gene of interest, where the polynucleotide molecules are so arranged that the first polynucleotide molecule affects the function of the second polynucleotide molecule. The two polynucleotide molecules may or may not be part of a single contiguous polynucleotide molecule and may or may not be adjacent. For example, a promoter is operably linked to a gene of interest if the promoter regulates or mediates transcription of the gene of interest in a cell. In one embodiment, the promoter is the EF1-α promoter. In an alternative embodiment, the promoter is the MND promoter or the PGK promoter.

In the various embodiments described herein, it is further contemplated that variants (naturally occurring or otherwise), alleles, homologs, conservatively modified variants, and/or conservative substitution variants of any of the particular polypeptides described are encompassed. As to amino acid sequences, one of ordinary skill will recognize that individual substitutions, deletions or additions to a nucleic acid, peptide, polypeptide, or protein sequence which alters a single amino acid or a small percentage of amino acids in the encoded sequence is a "conservatively modified variant" where the alteration results in the substitution of an amino acid with a chemically similar amino acid and retains the desired activity of the polypeptide. Such conservatively modified variants are in addition to and do not exclude polymorphic variants, interspecies homologs, and alleles consistent with the disclosure.

A given amino acid can be replaced by a residue having similar physiochemical characteristics, e.g., substituting one aliphatic residue for another (such as Ile, Val, Leu, or Ala for one another), or substitution of one polar residue for another (such as between Lys and Arg; Glu and Asp; or Gln and Asn). Other such conservative substitutions, e.g., substitutions of entire regions having similar hydrophobicity characteristics, are well known. Polypeptides comprising conservative amino acid substitutions can be tested in any one of the assays described herein to confirm that a desired activity, e.g. CSR activity and specificity of a native or reference polypeptide is retained.

Amino acids can be grouped according to similarities in the properties of their side chains (in A. L. Lehninger, in Biochemistry, second ed., pp. 73-75, Worth Publishers, New York (1975)): (1) non-polar: Ala (A), Val (V), Leu (L), Ile (I), Pro (P), Phe (F), Trp (W), Met (M); (2) uncharged polar: Gly (G), Ser (S), Thr (T), Cys (C), Tyr (Y), Asn (N), Gln (Q); (3) acidic: Asp (D), Glu (E); (4) basic: Lys (K), Arg (R), His (H). Alternatively, naturally occurring residues can be divided into groups based on common side-chain properties: (1) hydrophobic: Norleucine, Met, Ala, Val, Leu, Be; (2) neutral hydrophilic: Cys, Ser, Thr, Asn, Gln; (3) acidic: Asp, Glu; (4) basic: His, Lys, Arg; (5) residues that influence chain orientation: Gly, Pro; (6) aromatic: Trp, Tyr, Phe. Non-conservative substitutions will entail exchanging a member of one of these classes for another class. Particular conservative substitutions include, for example; Ala into Gly or into Ser; Arg into Lys; Asn into Gln or into His; Asp into Glu; Cys into Ser; Gln into Asn; Glu into Asp; Gly into Ala or into Pro; His into Asn or into Gln; Ile into Leu or into Val; Leu into Ile or into Val; Lys into Arg, into Gln or into Glu; Met into Leu, into Tyr or into Ile; Phe into Met, into Leu or into Tyr; Ser into Thr; Thr into Ser; Trp into Tyr; Tyr into Trp; and/or Phe into Val, into Ile or into Leu.

In some embodiments, the polypeptide described herein (or a nucleic acid encoding such a polypeptide) can be a functional fragment of one of the amino acid sequences described herein. As used herein, a "functional fragment" is a fragment or segment of a peptide which retains at least 50% of the wildtype reference polypeptide's activity according to an assay known in the art or described below herein. A functional fragment can comprise conservative substitutions of the sequences disclosed herein.

In some embodiments, the polypeptide described herein can be a variant of a sequence described herein. In some embodiments, the variant is a conservatively modified variant. Conservative substitution variants can be obtained by mutations of native nucleotide sequences, for example. A "variant," as referred to herein, is a polypeptide substantially homologous to a native or reference polypeptide, but which has an amino acid sequence different from that of the native or reference polypeptide because of one or a plurality of deletions, insertions or substitutions. Variant polypeptide-encoding DNA sequences encompass sequences that comprise one or more additions, deletions, or substitutions of nucleotides when compared to a native or reference DNA sequence, but that encode a variant protein or fragment thereof that retains activity of the non-variant polypeptide. A wide variety of PCR-based site-specific mutagenesis approaches are known in the art and can be applied by the ordinarily skilled artisan.

A variant amino acid or DNA sequence can be at least 90%, at least 91%, at least 92%, at least 93%, at least 94%, at least 95%, at least 96%, at least 97%, at least 98%, at least 99%, or more, identical to a native or reference sequence. The degree of homology (percent identity) between a native and a mutant sequence can be determined, for example, by comparing the two sequences using freely available computer programs commonly employed for this purpose on the world wide web (e.g., BLASTp or BLASTn with default settings).

Alterations of the native amino acid sequence can be accomplished by any of a number of techniques known to one of skill in the art. Mutations can be introduced, for example, at particular loci by synthesizing oligonucleotides containing a mutant sequence, flanked by restriction sites permitting ligation to fragments of the native sequence. Following ligation, the resulting reconstructed sequence encodes an analog having the desired amino acid insertion, substitution, or deletion. Alternatively, oligonucleotide-directed site-specific mutagenesis procedures can be employed to provide an altered nucleotide sequence having particular codons altered according to the substitution, deletion, or insertion required. Techniques for making such alterations are very well established and include, for example, those disclosed by Walder et al. (Gene 42:133, 1986); Bauer et al. (Gene 37:73, 1985); Craik (BioTechniques, January 1985, 12-19); Smith et al. (Genetic Engineering: Principles and Methods, Plenum Press, 1981); and U.S. Pat. Nos. 4,518,584 and 4,737,462, which are herein incorporated by reference in their entireties. Any cysteine residue not involved in maintaining the proper conformation of the polypeptide also can be substituted, generally with serine, to improve the oxidative stability of the molecule and prevent aberrant crosslinking. Conversely, cysteine bond(s) can be added to the polypeptide to improve its stability or facilitate oligomerization.

As used herein, the term "DNA" is defined as deoxyribonucleic acid. The term "polynucleotide" is used herein interchangeably with "nucleic acid" to indicate a polymer of nucleosides. Typically a polynucleotide is composed of nucleosides that are naturally found in DNA or RNA (e.g., adenosine, thymidine, guanosine, cytidine, uridine, deoxyadenosine, deoxythymidine, deoxyguanosine, and deoxycytidine) joined by phosphodiester bonds. However the term encompasses molecules comprising nucleosides or nucleoside analogs containing chemically or biologically modified bases, modified backbones, etc., whether or not found in naturally occurring nucleic acids, and such molecules may be preferred for certain applications. Where this application refers to a polynucleotide it is understood that both DNA, RNA, and in each case both single- and double-stranded forms (and complements of each single-stranded molecule) are provided. "Polynucleotide sequence" as used herein can refer to the polynucleotide material itself and/or to the sequence information (i.e. the succession of letters used as abbreviations for bases) that biochemically characterizes a specific nucleic acid. A polynucleotide sequence presented herein is presented in a 5' to 3' direction unless otherwise indicated.

The term "polypeptide" as used herein refers to a polymer of amino acids. The terms "protein" and "polypeptide" are used interchangeably herein. A peptide is a relatively short polypeptide, typically between about 2 and 60 amino acids in length. Polypeptides used herein typically contain amino acids such as the 20 L-amino acids that are most commonly found in proteins. However, other amino acids and/or amino acid analogs known in the art can be used. One or more of the amino acids in a polypeptide may be modified, for example, by the addition of a chemical entity such as a carbohydrate group, a phosphate group, a fatty acid group, a linker for conjugation, functionalization, etc. A polypeptide that has a nonpolypeptide moiety covalently or noncovalently associated therewith is still considered a "polypeptide." Exemplary modifications include glycosylation and palmitoylation. Polypeptides can be purified from natural sources, produced using recombinant DNA technology or synthesized through chemical means such as conventional solid phase peptide synthesis, etc. The term "polypeptide sequence" or "amino acid sequence" as used herein can refer to the polypeptide material itself and/or to the sequence information (i.e., the succession of letters or three letter codes used as abbreviations for amino acid names) that biochemically characterizes a polypeptide. A polypeptide sequence presented herein is presented in an N-terminal to C-terminal direction unless otherwise indicated.

In some embodiments, a nucleic acid encoding a polypeptide as described herein (e.g. a CAR polypeptide) is comprised by a vector. In some of the aspects described herein, a nucleic acid sequence encoding a given polypeptide as described herein, or any module thereof, is operably linked to a vector. The term "vector," as used herein, refers to a nucleic acid construct designed for delivery to a host cell or for transfer between different host cells. As used herein, a vector can be viral or non-viral. The term "vector" encompasses any genetic element that is capable of replication when associated with the proper control elements and that can transfer gene sequences to cells. A vector can include, but is not limited to, a cloning vector, an expression vector, a plasmid, phage, transposon, cosmid, artificial chromosome, virus, virion, etc.

As used herein, the term "expression vector" refers to a vector that directs expression of an RNA or polypeptide from sequences linked to transcriptional regulatory sequences on the vector. The sequences expressed will often, but not necessarily, be heterologous to the cell. An expression vector may comprise additional elements, for example, the expression vector may have two replication systems, thus allowing it to be maintained in two organisms, for example in human cells for expression and in a prokaryotic host for cloning and amplification. The term "expression" refers to the cellular processes involved in producing RNA and proteins and as appropriate, secreting proteins, including where applicable, but not limited to, for example, transcription, transcript processing, translation and protein folding, modification and processing. "Expression products" include RNA transcribed from a gene, and polypeptides obtained by translation of mRNA transcribed from a gene. The term "gene" means the nucleic acid sequence which is transcribed (DNA) to RNA in vitro or in vivo when operably linked to appropriate regulatory sequences. The gene may or may not include regions preceding and following the coding region, e.g. 5' untranslated (5'UTR) or "leader" sequences and 3' UTR or "trailer" sequences, as well as intervening sequences (introns) between individual coding segments (exons).

As used herein, the term "viral vector" refers to a nucleic acid vector construct that includes at least one element of viral origin and has the capacity to be packaged into a viral vector particle. The viral vector can contain the nucleic acid encoding a polypeptide as described herein in place of non-essential viral genes. The vector and/or particle may be utilized for the purpose of transferring nucleic acids into cells either in vitro or in vivo. Numerous forms of viral vectors are known in the art.

By "recombinant vector" is meant a vector that includes a heterologous nucleic acid sequence, or "transgene" that is capable of expression in vivo. It should be understood that the vectors described herein can, in some embodiments, be combined with other suitable compositions and therapies. In some embodiments, the vector is episomal. The use of a suitable episomal vector provides a means of maintaining the nucleotide of interest in the subject in high copy number extra-chromosomal DNA thereby eliminating potential effects of chromosomal integration.

As used herein, the terms "treat," "treatment," "treating," and "amelioration" refer to therapeutic treatments, wherein the object is to reverse, alleviate, ameliorate, inhibit, slow down or stop the progression or severity of a condition associated with a disease or disorder, e.g. ALL or other cancer. The term "treating" includes reducing or alleviating at least one adverse effect or symptom of a condition, disease or disorder. Treatment is generally "effective" if one or more symptoms or clinical markers are reduced. Alternatively, treatment is "effective" if the progression of a disease is reduced or halted. That is, "treatment" includes not just the improvement of symptoms or markers, but also a cessation of, or at least slowing of, progress or worsening of symptoms compared to what would be expected in the absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, remission (whether partial or total), and/or decreased mortality, whether detectable or undetectable. The term "treatment" of a disease also includes providing relief from the symptoms or side-effects of the disease (including palliative treatment).

As used herein, the term "pharmaceutical composition" refers to the active agent in combination with a pharmaceutically acceptable carrier e.g. a carrier commonly used in the pharmaceutical industry. The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. In some embodiments of any of the aspects, a pharmaceutically acceptable carrier can be a carrier other than water. In some embodiments of any of the aspects, a pharmaceutically acceptable carrier can be a cream, emulsion, gel, liposome, nanoparticle, and/or ointment. In some embodiments of any of the aspects, a pharmaceutically acceptable carrier can be an artificial or engineered carrier, e.g., a carrier in which the active ingredient would not be found to occur in nature.

As used herein, the term "administering" refers to the placement of a therapeutic or pharmaceutical composition as disclosed herein into a subject by a method or route which results in at least partial delivery of the agent at a desired site. Pharmaceutical compositions comprising agents as disclosed herein can be administered by any appropriate route which results in an effective treatment in the subject.

The term "statistically significant" or "significantly" refers to statistical significance and generally means a two standard deviation (2SD) or greater difference.

Other than in the operating examples, or where otherwise indicated, all numbers expressing quantities of ingredients or reaction conditions used herein should be understood as modified in all instances by the term "about." The term "about" when used in connection with percentages can mean ±1%.

As used herein, the term "comprising" means that other elements can also be present in addition to the defined elements presented. The use of "comprising" indicates inclusion rather than limitation.

The term "consisting of" refers to compositions, methods, and respective components thereof as described herein, which are exclusive of any element not recited in that description of the embodiment.

As used herein the term "consisting essentially of" refers to those elements required for a given embodiment. The term permits the presence of additional elements that do not materially affect the basic and novel or functional characteristic(s) of that embodiment of the invention.

The singular terms "a," "an," and "the" include plural referents unless context clearly indicates otherwise. Similarly, the word "or" is intended to include "and" unless the context clearly indicates otherwise. Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example."

Other terms are defined within the description of the various aspects and embodiments of the technology of the following.

BRIEF DESCRIPTION OF THE DRAWINGS

FIGS. 9 and 10 depict single-cell FACS sorting, expansion and validation of productive clones.

FIGS. 14A and 14B demonstrate a reduction in transduction efficiency of LDLR KO K562 cells.

DETAILED DESCRIPTION

Embodiments of the technology described herein relate to the discovery that an artificial antigen presenting cell (aAPC) can activate T cells more efficiently both in terms of time and cost, than commonly used methods. aAPCs as described herein are engineered to express chimeric stimulatory receptors (CSR). In some embodiments, a further improvement is achieved by knock down or inactivation of LDLR expression in the aAPC. The following provides description of the methods and various considerations necessary to practice the technology.

Accordingly, one aspect of the invention described herein relates to an aAPC engineered to comprise a first CSR that binds specifically with CD3; and a second CSR that binds specifically with CD28. As used herein, "chimeric stimulatory receptor" and "CSR" refers to a polypeptide comprising: i) an antibody reagent or natural ligand specific for a T cell co-stimulatory receptor (e.g., CD3, CD28, OX40, or 4-1BB, among others), or a T cell receptor (TCR); ii) a linker domain; and iii) a transmembrane domain.

An antigen presenting cell or APC is a cell which displays an antigen complexed with major histocompatibility complexes (MHC) on its surface. A T cell will recognize these complexes via a TCR. The role of an APC is to continuously process antigens and present the antigen to a T cell. Non-limiting examples of common, naturally occuring APCs include macrophages, B cells, and dendritic cells.

APCs are essential for the immune system to mount an effective adaptive immune response; the function of both cytotoxic and helper T cells require APCs. Antigen presentation determines the specificity of adaptive immunity and contributes to the immune response against intracellular and extracellular pathogens. An APC additionally plays an important role in priming the immune system to recognize a transformed cell, e.g., a malignant cell or tumor.

A CSR refers to a polypeptide comprising a fusion of an antibody reagent or a natural ligand that binds specifically to a TCR or co-stimulatory molecule, a linker domain, and a transmembrane domain. In one embodiment, the antibody reagent or natural ligand that binds specifically to a TCR or co-stimulatory molecule, the linker domain, and the transmembrane domain are arranged from N-terminus to C-terminus of the polypeptide. In another embodiment, the antibody reagent or natural ligand that binds specifically to a TCR or co-stimulatory molecule, the linker domain, and the transmembrane domain are arranged from C-terminus to N-terminus of the polypeptide. A CSR can be designed or engineered by a number of methods known in the art, as discussed below.

Figure 1:
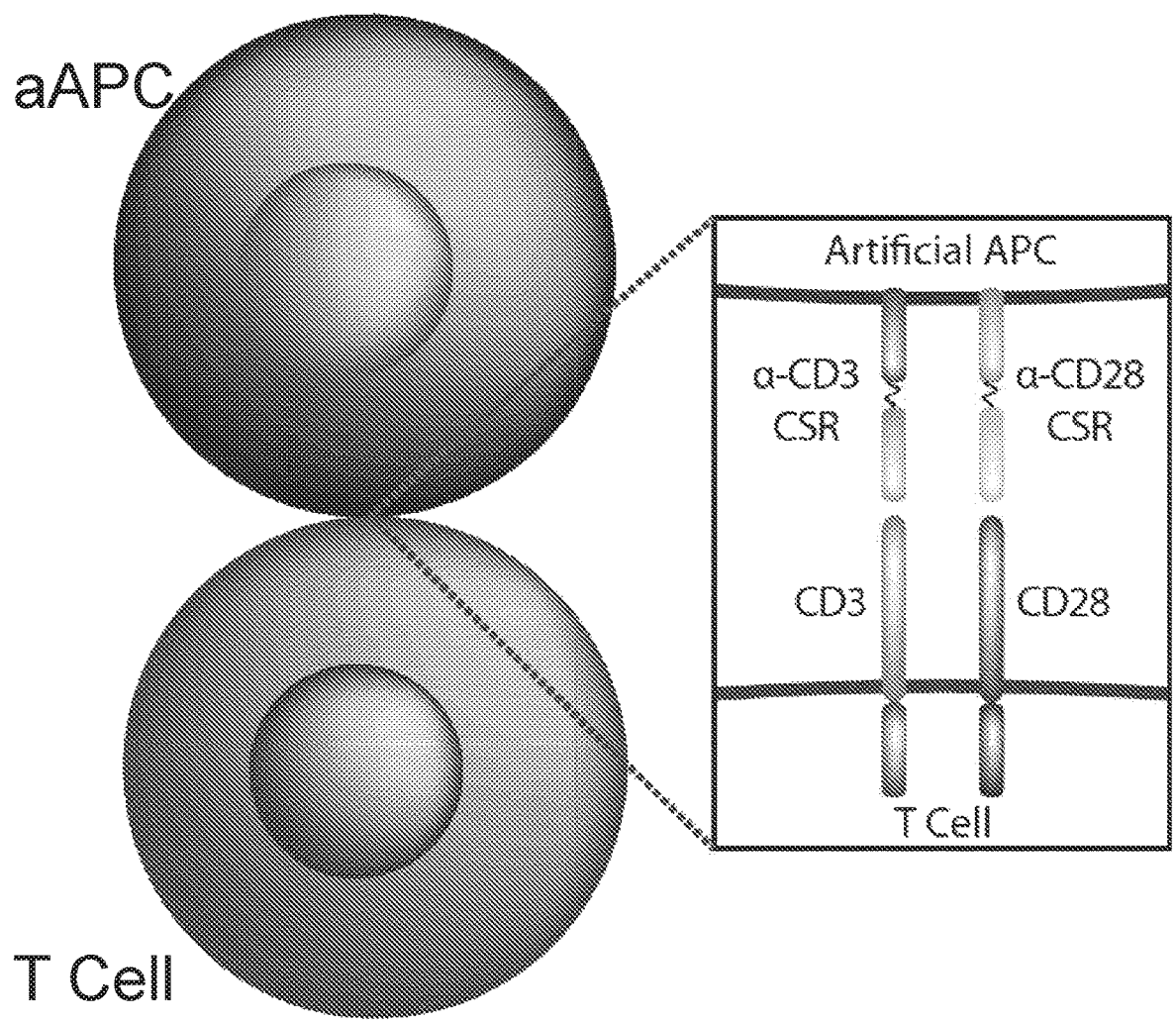
FIG. 1 depicts a diagram of the interface between a T cell and an aAPC. Both CD3 and CD28 molecules on the T cell surface are crosslinked by their respective chimeric stimulatory receptor expressed on the aAPC membrane inducing T cell activation and proliferation. Unlike anti-CD3 and anti-CD28-coated microspheres, genetically encoded anti-CD3 and anti-CD28 chimeric stimulatory receptors can be propagated without the need for soluble GMP-grade antibodies, which are expensive and not widely available.

In one embodiment, the first CSR and second CSR are expressed on the surface of the aAPC, such that the transmembrane domain spans the membrane of the aAPC, and the antibody reagent or natural ligand are present extracellularly, (i.e., extending outward, away from the cell membrane) (FIG. 1). In one embodiment, the first CSR and second CSR are expressed in tandem on a single receptor (e.g., a single receptor that comprises two different scFVs). In one embodiment, the first CSR and second CSR are expressed in a single construct, or from a single mRNA, e.g., use of an internal ribosomal entry site (IRES) to permit translation of both polypeptides.

In one embodiment, the first CSR and second CSR are constitutively expressed. As used herein, "constitutively expressed" refers to expression of a gene continuously by a cell. In one embodiment, the first CSR and second CSR are facultatively expressed, wherein the gene is only transcribed when required, or when induced by the presence of an exogenous agent or condition.

In one embodiment, the first CSR and second CSR are encoded by a first and second recombinant nucleic acid sequences, respectively. As used herein, "recombinant nucleic acid sequence," also referred to as "chimeric DNA" refers to human manipulated DNA molecules that are formed using, for example, molecular cloning, to create nucleic acid sequences not found in natively in a genome. The gene product of recombinant DNA is referred to as recombinant protein. The DNA used to generate recombinant DNA can originate from various species. In one embodiment, the first CSR and second CSR are derived from human DNA. In another embodiment, the first CSR and second CSR are derived from mammalian DNA. In another embodiment, the first CSR and second CSR are derived from non-mammalian DNA. In another embodiment, the first CSR and second CSR are derived from different species.

In one embodiments, recombinant DNA encoding a CSR is comprised in a vector for delivery into an aAPC. Non-limiting examples of vectors used for DNA delivery into a cell include viral vectors, plasmid vectors, and cosmid vectors.

As used herein, the term "antibody reagent" refers to a polypeptide that includes at least one immunoglobulin variable domain or immunoglobulin variable domain sequence and which specifically binds a given antigen. An antibody reagent can comprise an antibody or a polypeptide comprising an antigen-binding domain of an antibody. In some embodiments of any of the aspects, an antibody reagent can comprise a monoclonal antibody or a polypeptide comprising an antigen-binding domain of a monoclonal antibody. For example, an antibody can include a heavy (H) chain variable region (abbreviated herein as VH), and a light (L) chain variable region (abbreviated herein as VL). In another example, an antibody includes two heavy (H) chain variable regions and two light (L) chain variable regions. The term "antibody reagent" encompasses antigen-binding fragments of antibodies (e.g., single chain antibodies, Fab and sFab fragments, F(ab')2, Fd fragments, Fv fragments, scFv, CDRs, and domain antibody (dAb) fragments (see, e.g. de Wildt et al., Eur J. Immunol. 1996; 26(3):629-39; which is incorporated by reference herein in its entirety)) as well as complete antibodies. An antibody can have the structural features of IgA, IgG, IgE, IgD, or IgM (as well as subtypes and combinations thereof). Antibodies can be from any source, including mouse, rabbit, pig, rat, and primate (human and non-human primate) and primatized antibodies. Antibodies also include midibodies, humanized antibodies, chimeric antibodies, and the like.

The VH and VL regions can be further subdivided into regions of hypervariability, termed "complementarity determining regions" ("CDR"), interspersed with regions that are more conserved, termed "framework regions" ("FR"). The extent of the framework region and CDRs has been precisely defined (see, Kabat, E. A., et al. (1991) Sequences of Proteins of Immunological Interest, Fifth Edition, U.S. Department of Health and Human Services, NIH Publication No. 91-3242, and Chothia, C. et al. (1987) J. Mol. Biol. 196:901-917; which are incorporated by reference herein in their entireties). Each VH and VL is typically composed of three CDRs and four FRs, arranged from amino-terminus to carboxy-terminus in the following order: FR1, CDR1, FR2, CDR2, FR3, CDR3, FR4.

Antibody binding domains and ways to select and clone them are well known to those of ordinary skill in the art. In another embodiment, the antibody reagent is an anti-OKT3 antibody reagent and has the sequence selected from SEQ ID NO: 27 or 31. In one embodiment, the anti-OTK3 antibody reagent corresponds to the sequence of SEQ ID NO: 27 or 31; or comprises the sequence of SEQ ID NO: 27 or 31; or comprises a sequence with at least 80%, at least 85%, at least 90%, at least 91%, at least 92%, at least 93%, at least 94%, at least 95%, at least 96%, at least 97%, at least 98%, at least 99% or greater sequence identity to the sequence of SEQ ID NO: 27 or 31.

In another embodiment, the antibody reagent is an anti-CD28 antibody reagent and has the sequence of SEQ ID NO: 35. In one embodiment, the anti-CD28 antibody corresponds to the sequence of SEQ ID NO: 35; or comprises the sequence of SEQ ID NO: 35; or comprises a sequence with at least 80%, at least 85%, at least 90%, at least 91%, at least 92%, at least 93%, at least 94%, at least 95%, at least 96%, at least 97%, at least 98%, at least 99% or greater sequence identity to the sequence of SEQ ID NO: 35.

In one embodiment, the first CSR or second CSR is fused or crosslinked to a co-stimulatory molecule or co-stimulatory domain. As used herein, the term "co-stimulatory domain" refers to an intracellular signaling domain of a co-stimulatory molecule. Co-stimulatory molecules are cell surface molecules other than antigen receptors or Fc receptors that provide a second signal required for efficient activation and function of T lymphocytes upon binding to antigen. Illustrative examples of such co-stimulatory molecules include CARD11, CD2, CD7, CD27, CD28, CD30, CD40, CD54 (ICAM), CD83, CD134 (OX40), CD137 (4-1BB), CD150 (SLAMF1), CD152 (CTLA4), CD223 (LAG3), CD270 (HVEM), CD273 (PD-L2), CD274 (PD-L1), CD278 (ICOS), DAP10, LAT, NKD2C SLP76, TRIM, and ZAP70. In one embodiment, the intracellular domain is the intracellular domain of 4-1BB.

As used herein "natural ligand" refers to a naturally occurring ligand that binds a receptor in nature. Binding of a natural ligand to a receptor will generally transduce a signal, positive or negative, alone or in conjunction with other receptors or co-stimulatory or co-inhibiting molecules. A ligand is a molecule which specifically binds to a portion of a protein and/or receptor as that term is defined herein. A ligand can be found on the surface of a cell or organelle, or within the cytoplasmic space. Ligand-protein/receptor binding can result in the alteration of the protein and/or receptor, or activate a physiological response, for example, the activation of a signaling pathway. In one embodiment, a CSR described herein comprises a CD28 natural ligand. The CD28 natural ligand can be full length, or a fragment thereof. The CD28 natural ligand can be truncated to exclude its intracellular domain. Exemplary CD28 natural ligands are described below.

As used herein "linker domain" refers to an oligo- or polypeptide region from about 2 to about 100 amino acids in length, which links together any of the domains/regions of the CSR as described herein. In some embodiment, linkers can include or be composed of flexible residues such as glycine and serine so that the adjacent protein domains are free to move relative to one another. Longer linkers may be used when it is desirable to ensure that two adjacent domains do not sterically interfere with one another. Linkers may be cleavable or non-cleavable. Examples of cleavable linkers include 2A linkers (for example T2A), 2A-like linkers or functional equivalents thereof and combinations thereof. Non-limiting examples of linkers include linkers derived from *Thosea asigna*.

As used herein, a "transmembrane domain" (TM) refers to the region of the CSR which is inserted into or crosses the plasma membrane, e.g., of the aAPC. The transmembrane domain of a CSR as described herein can be a transmembrane region or fragment thereof of a transmembrane protein (for example Type I transmembrane proteins), an artificial hydrophobic sequence, or a combination thereof. Other transmembrane domains will be apparent to those of skill in the art and can be used in connection with alternate embodiments of the invention. A selected transmembrane domain would preferably not interfere with the intended function of the CSR. As used in the context of transmembrane regions, "fragment thereof" refers to a portion of a transmembrane region that is sufficient to anchor or attach a protein to a cell surface. In some embodiments, the transmembrane domain of a CSR described herein comprises a transmembrane domain or fragment thereof selected from the transmembrane domain of an alpha, beta, or zeta chain of a T-cell receptor, CD28, CD3 epsilon, CD45, CD4, CD5, CD8, CD9, CD16, CD22, CD33, CD37, CD64, CD80, CD86, CD134, CD137, CD154, KIRDS2, OX40, CD2, CD27, LFA-1 (CD11a, CD18), ICOS (CD278), 4-1BB (CD137), GITR, CD40, BAFFR, HVEM (LIGHTR), SLAMF7, NKp80 (KLRF1), CD160, CD19, IL2R beta, IL2R gamma, IL7Ra, ITGA1, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, TNFR2, DNAM1 (CD226), SLAMF4 (CD244, 2B4), CD84, CD96 (Tactile), CEACAM1, CRT AM, Ly9 (CD229), CD160 (BY55), PSGL1, CD100 (SEMA4D), SLAMF6 (NTB-A, Ly108), SLAM (SLAMF1, CD150, IPO-3), BLAME (SLAMF8), SELPLG (CD162), LTBR, PAG/Cbp, NKp44, NKp30, NKp46, NKG2D, and/or NKG2C. In some embodiments, the transmembrane domain or fragment thereof of a CSR as described herein comprises a transmembrane domain selected from the transmembrane domain of CD28 and CD8.

In one embodiment, the first CSR and/or second CSR further comprises the first five amino acids of CD3 zeta (CD3) (SEQ ID NOs: 7 and 6). CD3 is a T cell co-receptor that facilitates T lymphocytes activation when simultaneously engaged with the appropriate costimulation (e.g., binding of a co-stimulatory molecule). A CD3 complex consists of 4 distinct chains; mammalian CD3 consists of a CD3γ chain, a CD3δ chain, and two CD3ε chains. These chains associate with the T cell receptor (TCR) and CD3ζ to form a complex that generates an activation signal in T lymphocytes. In alternative embodiments, the first CSR and/or second CSR further comprises full length CD3ζ, truncated CD3ζ, or a fragment thereof that permit function in the context of the TCR complex.

In one embodiment, the first CSR and/or second CSR further comprises a fluorescent protein. In one embodiment, the first CSR and the second CSR express different color fluorescent proteins (i.e., the first CSR expresses a green fluorescent protein and the second CSR expresses a red fluorescent protein). Non-limiting examples of green fluorescent proteins include GFP, eGFP, Emerald, Superfolder GFP, Azami Green, mWasabi, TagGFP, TurboGFP, AcGFP, ZsGreen, and T-Sapphire. Non-limiting examples of blue fluorescent proteins include eBFP, eBFP2, Azurite, and mTagBFP. Non-limiting examples of cyan fluorescent proteins include eCFP, mECFP, Cerulean, mTurquoise, CyPet, AmCyanl, Midori-Ishi Cyan, TagCFP, and mTFP1. Non-limiting examples of yellow fluorescent proteins include eYFP, Topaz, Venus, mCitrine, YPet, TagYFP, PhiYFP, ZsYellow1, and mBanana. Non-limiting examples of orange fluorescent proteins include Kusabira Orange, Kusabira Orange2, mOrange, mOrange2, dTomato, dTomato-Tandem, TagRFP, TagR FP-T, DsRed, DsRed2, DsRed-Express, DsRed-Monomer, and mTangerine. Non-limiting examples of red fluorescent proteins include mRuby, mApple, mStrawberry, AsRed2, JRed, mCherry, HcRed1, mRasberry, dKeima-Tandem, HcRed-Tandem, mPlum, and AQ143. In one embodiment, the fluorescent protein comprised in the first CSR and second CSR is used to determine if an aAPC is expressing the first CSR and/or second CSR, for example by FACS sorting or microscopy analysis.

In one embodiment, the first CSR is a CD3 (OKT3) CSR, which comprises the CD8 hinge region and TM domain, the first 5 amino acids of CD3ζ, T2A linker, and GFP and comprises a sequence selected from SEQ ID NO: 1 or 10. In one embodiment, the second CSR is a CD28 CSR (9.3), which comprises the CD28 hinge region, TM domain, and intracellular domain, T2A linker, and mCherry and comprises a sequence of SEQ ID NO: 19.

In one embodiment, the first CSR sequence corresponds to the sequence of SEQ ID NO: 1 or 10; or comprises the sequence of SEQ ID NO: 1 or 10; or comprises a sequence with at least 80%, at least 85%, at least 90%, at least 91%, at least 92%, at least 93%, at least 94%, at least 95%, at least 96%, at least 97%, at least 98%, at least 99% or greater sequence identity to the sequence of SEQ ID NO: 1 or 10.

In one embodiment, the second CSR sequence corresponds to the sequence of SEQ ID NO: 19; or comprises the sequence of SEQ ID NO: SEQ ID NO: 19; or comprises a sequence with at least 80%, at least 85%, at least 90%, at least 91%, at least 92%, at least 93%, at least 94%, at least 95%, at least 96%, at least 97%, at least 98%, at least 99% or greater sequence identity to the sequence of SEQ ID NO: 19.

A "T cell receptor" (TCR) refers to a heterodimeric receptor molecule found on the surface of a T cell that recognizes and binds an antigen bound to/displayed upon the MHC or an APC. Binding of MHC-displayed antigen by the TCR initiates signal transduction by the TCR necessary for activation of the T cell. For a T cell to be fully activated, the T cell must be co-stimulated (e.g., receiving simultaneous first and second signaling via binding of an antigen-specific and antigen non-specific molecule, respectively).

In one embodiment, the first CSR comprises an antibody or antigen-binding domain thereof that specifically binds to CD28, and the second CSR comprises an antibody or antigen-binding domain thereof that specifically binds to CD3. Binding of CD28 and CD3 by the anti-CD28 and anti-CD3 domains stimulate T cells to proliferate and/or activate. In another embodiment, the first CSR comprises an antibody or antigen-binding domain thereof specific for binding to 4-1BBL; and the second CSR comprises an antibody or antigen-binding domain thereof specific for binding to OX40L. In another embodiment, the first CSR comprises a natural ligand that binds specifically to 4-1BBL, and the second CSR comprised a natural ligand that binds specifically to OX40L. It is contemplated herein that any other known T cell receptors and/or co-stimulatory molecules can be used to generate aAPC's as described herein.

CD28 is a receptor protein expressed on a T cell surface that provides a co-stimulatory signal for T cell activation. As noted above, engagement of CD28 and CD3 by their ligands promote T cell proliferation. CD28 natural ligands include CD80 (B7-1) and CD86 (B7-2). CD28 sequences are known for a number of species, e.g., human CD28 (NCBI Gene ID: 940) and mRNA (NCBI Ref Seq NM_001243077.1). CD28 can refer to human CD28, including naturally occurring variants and alleles thereof. In some embodiments of, e.g., in veterinary applications, CD28 can refer to the CD28 of, e.g., dog, cat, cow, horse, pig, and the like. Homologs and/or orthologs of human CD28 are readily identified for such species by one of skill in the art, e.g., using the NCBI ortholog search function or searching available sequence data for a given species for sequence similar to a reference CD28 sequence.

CD3 is a T cell co-receptor found on the surface of a T cell. CD3 sequences are known for a number of species, e.g., human CD3e (NCBI Gene ID: 916) and mRNA (NCBI Ref Seq NM_000733.3). CD3 can refer to human CD3, including naturally occurring variants, molecules, and alleles thereof. In some embodiments of any of the aspects, e.g., in veterinary applications, CD3 can refer to the CD3 of, e.g., dog, cat, cow, horse, pig, and the like. Homologs and/or orthologs of human CD3 are readily identified for such species by one of skill in the art, e.g., using the NCBI ortholog search function or searching available sequence data for a given species for sequence similar to a reference CD3 sequence.

4-1BBL is a type 2 transmembrane glycoprotein belonging to the TNFR/TNF ligand superfamily. 4-1BBL is a co-stimulatory ligand that binds receptor 4-1BB (CD137) expressed on T cell. 4-1BBL is expressed on professional APCs including dendritic cells, macrophages, and activated B cells. 4-1BBL sequences are known for a number of species, e.g., human 4-1BBL, also known as TNFSF9 (NCBI Gene ID: 8744) and mRNA (NCBI Ref Seq NM_003811.3). 4-1BBL can refer to human 4-1BBL, including naturally occurring variants, molecules, and alleles thereof. In some embodiments of any of the aspects, e.g., in veterinary applications, 4-1BBL can refer to the 4-1BBL of, e.g., dog, cat, cow, horse, pig, and the like. Homologs and/or orthologs of human 4-1BBL are readily identified for such species by one of skill in the art, e.g., using the NCBI ortholog search function or searching available sequence data for a given species for sequence similar to a reference 4-1BBL sequence.

OX40L is a natural ligand for the CD134 receptor, OX40. OX40L is expressed on APCs, and activated T cells, among others. OX40 and OX40L are both expressed at higher levels after antigen presentation to a T cell. CD28 ligation also induces OX40 and OX40L expression. OX40L sequences are known for a number of species, e.g., human OX40L, also known as TNFSF4 (NCBI Gene ID: 7292) and mRNA (NCBI Ref Seq NM_001297562.1). OX40L can refer to human OX40L, including naturally occurring variants, molecules, and alleles thereof. In some embodiments of any of the aspects, e.g., in veterinary applications, OX40L can refer to the OX40L of, e.g., dog, cat, cow, horse, pig, and the like. Homologs and/or orthologs of human OX40L are readily identified for such species by one of skill in the art, e.g., using the NCBI ortholog search function or searching available sequence data for a given species for sequence similar to a reference OX40L sequence.

In one embodiment, an aAPC as described herein is engineered to lack an expressible low density lipoprotein receptor (LDLR) gene. In another embodiment, an aAPC comprises a deletion in the native LDLR-encoding nucleic acid sequence. In another embodiment, an aAPC comprises a deletion of the native LDLR-encoding nucleic acid sequence, such that the cell does not express a functional LDLR gene product. The lack of a function LDLR can increase the capacity of the aAPC to take up a lentivirus (described herein below).

LDLR is a cell surface protein that mediates endocytosis of low density lipoprotein. LDLR sequences are known for a number of species, e.g., human LDLR, (NCBI Gene ID: 3949) and mRNA (NCBI Ref Seq NM_000527.4). LDLR can refer to human LDLR, including naturally occurring variants, molecules, and alleles thereof. In some embodiments, e.g., in veterinary applications, LDLR can refer to the LDLR of, e.g., dog, cat, cow, horse, pig, and the like. Homologs and/or orthologs of human LDLR are readily identified for such species by one of skill in the art, e.g., using the NCBI ortholog search function or searching available sequence data for a given species for sequence similar to a reference LDLR sequence.

One skilled in the art can engineer an aAPC to lack an expressible LDLR gene using standard techniques. In one embodiment, the recently-discovered CRISPR-associated (Cas) system, such as CRISPR-Cas9, can be used for genome-editing. CRISPR-Cas technology for editing of genomes is fully described in Doudna, J A, and Charpentier, E. Science, 346: 6213, 2014, which is incorporated by reference herein in its entirety. This is a practicable, convenient and flexible method of gene editing, and a number of adaptations and improvements on the basic technology are now in common use.

As described herein, a deletion of an entire gene, or fragment thereof can be introduced by utilizing the CRISPR/Cas system. Non-limiting exemplary CRISPR-Cas9 methods for inducing the loss of a functional LDLR gene are described in Example 1.

In alternative embodiments, mutations to delete LDLR coding sequence or otherwise mutate the gene to either eliminate expression of the protein or eliminate expression of functional LDLR protein can be introduced by utilizing TALENs or ZFN technology, which are known in the art. Methods of engineering nucleases to achieve a desired sequence specificity are known in the art and are described, e.g., in Kim (2014); Kim (2012); Belhaj et al. (2013); Urnov et al. (2010); Bogdanove et al. (2011); Jinek et al. (2012) Silva et al. (2011); Ran et al. (2013); Carlson et al. (2012); Guerts et al. (2009); Taksu et al. (2010); and Watanabe et al. (2012); each of which is incorporated by reference herein in its entirety.

In alternate embodiments, LDLR gene expression can be depleted via other techniques known in the field. In some embodiments, an agent that inhibits LDLR gene or gene product expression is an inhibitory nucleic acid. As used herein, "inhibitory nucleic acid" refers to a nucleic acid molecule, e.g., double-stranded RNAs (dsRNAs), inhibitory RNAs (iRNAs), and the like which can inhibit the expression of a target gene. Inhibitory nucleic acid technology is known to those of ordinary skill in the art and is more fully described in, e.g., Wilson, R C, and Doudna, J A. (2013) Annual Review of Biophysics 42(217-239) and references cited therein. In another embodiment, the agent is a nucleic acid that encodes a protein that specifically bind to and inhibits LDLR function. A non-limiting example of a protein that binds to and inhibits LDLR function is Proprotein convertase subtilisin/kexin type 9 (PCSK9).

One can evaluate the lack of expressible LDLR gene or LDLR gene expression, for example by RT-PCR, northern blotting, western blotting, ELISA, or immunohistochemistry. To evaluate the presence of a functional LDLR gene, one can evaluate whether LDLR is capable of mediating endocytosis of low density lipoprotein using standard assays.

In one embodiment, the aAPC is viable but non-dividing. aAPCs can be rendered non-dividing, for example by gamma irradiation or mitomycin treatment. See, e.g., Llames et al. Tissue Eng. Part B Rev. 21:345-353 (2015) and references cited therein. As one example, the aAPCs can be treated with gamma rays in the range of 3,000 to 3,600 rads.

One skilled in the art can assess the cellular viability of an aAPC using various assays, for example by dye exclusion assays using, e.g., trypan blue, eosin or propidium iodide. One can assess whether an aAPC is dividing using proliferation assays known in the art, for example using a [$^3$H] thymidine incorporation assay.

In some embodiments, aAPC are frozen, and thawed when needed, retaining function as an aAPC. In some embodiments, the frozen aAPC is stored at at least −20° C. In some embodiments, frozen aAPC are stored at at least −80° C. In some embodiments, frozen aAPC are stored in liquid nitrogen. In some embodiments of any aspect, frozen aAPC can be stored for at least 1 day, at least 2 days, at least 3 days, at least 4 days, at least 5 days, at least 6 days, at least 1 week, at least 2 weeks, at least 3 weeks, at least 1 month, at least 2 months, at least 3 months, at least 4 months, at least 5 months, at least 6 months, at least 7 months, at least 8 months, at least 9 months, at least 10 months, at least 11 months, at least 1 year, at least 2 years, at least 3 years, at least 4 years, at least 5 years, or more. In one embodiment, frozen aAPCs are stored in liquid nitrogen for more than 2 years.

In one embodiment, aAPC are slow thawed, e.g., placed in ice and allowed to thaw without any intervention. In one embodiment, aAPC are quick thawed, e.g., the frozen aAPC are placed in a water bath at 37° C. to thaw, and then placed on ice immediately after thawing is complete. As used herein, "a functional aAPC" refers to an aAPC that functions like and resembles an aAPC prior to being frozen (i.e., the thawed aAPC expresses the first CSR and second CSR at the same level as prior to being frozen). In one embodiment of any aspect, a thawed aAPC does not proliferate.

In one embodiment, the aAPC further comprises a T cell target molecule. As used herein, a "T cell target molecule" is a ligand for a T cell receptor, e.g., a naturally-occurring T cell receptor, or an engineered T cell receptor, e.g., a CAR. A T cell target molecule will activate a T cell, provided appropriate co-stimulatory signals. In this context, the T cell target molecule can be a full length target polypeptide, i.e., as it occurs in vivo or native to the genome, or a fragment thereof that binds the T cell receptor and promotes proliferation and/or activation of the T cell (given the appropriate co-stimulatory signals).

In one embodiment, the T cell target molecule expressed on the surface of an aAPC includes, but is not limited to CD19, BCMA, SLAMF7, EGFR or EGFR variant III. In one embodiment, the T cell target molecule is CD19. In addition, it is contemplated that any T cell target molecule expressed on the aAPC can be targeted by a chimeric antigen receptor CAR—that is, when an aAPC is engineered to express a T cell target molecule, that molecule can be any molecule that binds the ligand-binding moiety of a T cell receptor, e.g., a CAR or other T cell receptor. In one embodiment, the T cell target molecule expressed on the aAPC is constitutively expressed. In another embodiment, the T cell target molecule expressed on the aAPC is expressed in a facultative manner. One skilled in the art would be capable of engineering an aAPC to express a T cell target molecule using known techniques.

In one embodiment, the expression of a T cell target molecule expressed on the surface of the aAPC will facilitate the recognition of the aAPC by a T cell or CAR T cell. In this embodiment, the presence of the T cell target molecule on the aAPC provides a mechanism for eliminating the aAPC via T cell-mediated mechanisms.

In one embodiments of any aspect, the aAPC is engineered from a human cell. In one embodiments, the aAPC is engineered from an erthromyeloid cell. In one embodiment, the erthromyeloid cell is a K562 cell. In another embodiment, an aAPC is engineered from a cell of myeloid origin. Non-limiting examples of cells of myeloid origin include megakaryocytes, thrombocytes, erythrocytes, mast cells, myeloblasts, basophils, neutrophils, eosinophils, monocytes, macrophages, dendritic cells, and platelets. In another embodiment, an aAPC is engineered from a cell lacking HLA expression (e.g., an immature hematopoietic cell), or a cell that has been engineered to lack functional HLA via gene editing (e.g., CRISPR). An aAPC can be engineered from an non-adherent cell or an adherent cell.

K562 is an immortalized myelogenous leukemia cell line. The line is of the erythroleukemia type, derived from a patient presenting with chronic myelogenous leukemia in blast crisis. While other cells can be engineered to generate aAPCs as described herein, K562 cells are well suited for use as an aAPC as they do not express major histocompatibility complex molecules, and therefore would not provoke allogeneic responses. Further, K562 cells express adhesion molecules that enhance T cell-aAPC interactions. K562 cells are commercially available, for example from American Type Culture Collection (ATCC), Manassas, Va., product ATCC CCL-243. Standard cell culture protocols and techniques known in the art are used to maintain K562 cells in culutre.

In one embodiment, the first CSR and second CSR are expressed in the K562 cell via lentiviral expression, e.g., retroviral vector. Retroviruses, such as lentiviruses, provide a convenient platform for delivery of nucleic acid sequences encoding a gene, or chimeric gene of interest. A selected nucleic acid sequence can be inserted into a vector and packaged in retroviral particles using techniques known in the art. The recombinant virus can then be isolated and delivered to cells, e.g. in vitro or ex vivo. Retroviral systems are well known in the art and are described in, for example, U.S. Pat. No. 5,219,740; Kurth and Bannert (2010) "Retroviruses: Molecular Biology, Genomics and Pathogenesis" Calster Academic Press (ISBN:978-1-90455-55-4); and Hu and Pathak Pharmacological Reviews 2000 52:493-512; which are incorporated by reference herein in their entirety. Components of lentiviral system for efficient DNA delivery can be purchased from OriGene; Rockville, Md.

In one aspect provided herein is a method for expanding and/or activating a T cell or population thereof, comprising contacting any of the aAPC described herein with a T cell, or population thereof.

In one aspect provided herein is a method for treating cancer, a plasma cell disease or disorder, or an autoimmune disease or disorder comprising contacting an aAPC as described above with a CAR T cell or population thereof, thereby activating the CAR T cell, and administering the activated CAR T cell to a subject in need thereof.

T cell activation occurs through simultaneous engagement of the T cell receptor and co-stimulatory molecules (i.e., CD3 and CD28). This results in the activation of downstream signaling pathways (e.g., PI3K signaling), and eventual immune response (involving cytokine production). Following activation, a T cell expresses a variety of proteins (also known as markers), including, but not limited to CD69, CD71, CD25, and HLA-DR. In addition, an activated T cell has an altered cell surface protein glycosylation profile.

T cells to be contacted with an aAPC can be obtained using standard techniques known in the field. For example, T cells can be isolated from peripheral blood taken from a donor or patient. T cells can be isolated from a mammal. Preferably, T cells are isolated from a human. A ordinarily skilled person can generate CAR T cells to be contacted with an aAPC using standard techniques. Briefly, T cells isolated from peripheral blood of a patient are engineered to express a chimeric antigen receptor on their surface using viral or non-viral vectors. In one embodiment, the T cells can be isolated from a healthy subject. In antoher embodiment, the T cells can be isolated from a patient having been diagnosed with a disease or disorder.

In one embodiment, the contacting of an aAPC and T cell or CAR T cell occurs in vitro. In another embodiment, the contacting occurs in suspension. If an aAPC is engineered from an adherent cell, the adherent aAPC will be contacted by a T cell in suspension. In another embodiment, an aAPC is contacted with a T cell or CAR T cell for at least 4 days, for at least 5 days, for at least 6 days, for at least 7 days, for at least 8 days, for at least 9 days, or more. In a preferred embodiment of any aspect, the contact of the aAPC and T cell or CAR T cell is continuous for the duration of the contact.

In one embodiment of any aspect, contacting an aAPC with a T cell or CAR T cell results in the expansion of the T cell or CAR T cell population. In one embodiment, following contact by an aAPC, the T cell or CAR T cell population will undergo 5-7 doublings in 10 days. In one embodiment, following contact by an aAPC, the T cell or CAR T cell population increases at least 1-fold, at least 2-fold, at least 3-fold, at least 4-fold, at least 5-fold, at least 6-fold, at least 7-fold, at least 9-fold, or at least 10-fold or more. One skilled in the art will be capable of measuring T cell or CAR T cell growth, for example, via a T cell expansion curve. Briefly, T cells or CAR T cells are seeded at day 0 with an aAPC or population thereof. Total T cell or CAR T cell numbers and mean T cell or CAR T cell volumes are measured at days 3, 5, 7, and 9 using, e.g., a Multisizer™ 3 Coulter Counter (Beckman Coulter). Cellular viability can be determined by staining, e.g., with Acridine Orange/Propidiumlodide exclusion dye using a Luna-FL™ Cell Counter (Logos Biosystems).

One skilled in the art will be capable of determining if a T cell or CAR T cell has become activated following contact with an aAPC. For example, one can use a Proliferative Capacity assay (CFSE dilution and absolute T cell or CAR T cell numbers are assessed by FACS using fluorescently-labeled counting beads), a Cytokine Production assay (10-Plex Luminex Assays using cytokine levels as a readout), a Target-cell Killing Capacity assay (Bioluminescence analysis of target cells in vitro or animal model system to track both tumor and engineered T cells infused in immunodeficient mice), and/or a Cell Degranulation Analysis (CD107a release assay in response to target cells as measured by FACS). One skilled in the art can additionally determine if a T cell is activated by assessing the markers present on the T cell surface, or by examining the glycosylation profile of the cell surface.

In one embodiment of any aspect, a subject is administered activated CAR T cells that are engineered to express an XCAR, wherein X represents a tumor antigen (or cancer associated antigen) as described herein that is expressed on a subject's tumor cell.

In one embodiment, a subject is administered activated CAR T cells that are engineered to express an XCAR described herein, wherein the cancer cells express X on their surface. In one embodiment, X is expressed on both normal cells and cancers cells, but is expressed at lower levels on normal cells. In one embodiment, the method further comprises selecting a CAR that binds X with an affinity that allows the XCAR to recognize and kill the cancer cells expressing X but less than 30%, 25%, 20%, 15%, 10%, 5% or less of the normal cells expressing X are killed. Such activity can be evaluated for example in a cell killing assay such as a chromium-51 release cytotoxicity assay or a similar fluorescence-based assay. In one embodiment, the selected CAR has an antigen binding domain that has a binding affinity KD of $10^{-4}$ M to $10^{-8}$ M, e.g., $10^{-5}$ M to $10^{-7}$ M, e.g., $10^{-6}$ M or $10^{-7}$ M, for the target antigen.

Described herein is a type of cellular therapy in which activated CAR T cells are infused to a recipient in need thereof. The infused cell is able to kill tumor cells in the recipient. Unlike antibody therapies, CAR T cells, are able to replicate in vivo, resulting in long-term persistence that can lead to sustained tumor control. In various embodiments, activated CAR T cells administered to the patient persist in the patient for at least four months, five months, six months, seven months, eight months, nine months, ten months, eleven months, twelve months, thirteen months, fourteen month, fifteen months, sixteen months, seventeen months, eighteen months, nineteen months, twenty months, twenty-one months, twenty-two months, twenty-three months, two years, three years, four years, or five years after administration of the T cell to the patient.

In one embodiment, activated CAR T cells are administered to a subject who has cancer. In one embodiment, the subject has been diagnosed with cancer. In one embodiment, the cancer is leukemia, lymphoma, multiple myeloma, or a solid tumor.

With respect to leukemia, non-limiting examples of leukemia include acute myeloid leukemia (AML), Chronic myeloid leukemia (CML), Acute lymphocytic leukemia (ALL), and Chronic lymphocytic leukemia (CLL). In one embodiment, the cancer is ALL or CLL.

With respect to lymphoma, non-limiting examples of lymphoma include Diffuse large B-cell lymphoma (DLBCL), Follicular lymphoma, Small lymphocytic lymphoma (SLL), Mantle cell lymphoma (MCL), Marginal zone lymphomas, Burkitt lymphoma, hairy cell leukemia. (HCL).

In one embodiment, the cancer is DLBCL or Follicular lymphoma.

With respect to solid tumors, non-limiting examples of solid tumors include Adrenocortical Tumor, Alveolar Soft Part Sarcoma, Chondrosarcoma, Colorectal Carcinoma, Desmoid Tumors, Desmoplastic Small Round Cell Tumor, Endocrine Tumors, Endodermal Sinus Tumor, Epithelioid Hemangioendothelioma, Ewing Sarcoma, Germ Cell Tumors, Giant Cell Tumor of Bone and Soft Tissue, Hepatoblastoma, Hepatocellular Carcinoma, Melanoma, Nephroma, Neuroblastoma, Non-Rhabdomyosarcoma Soft Tissue Sarcoma (NRSTS), Osteosarcoma, Paraspinal Sarcoma, Renal Cell Carcinoma, Retinoblastoma, Rhabdomyosarcoma, Synovial Sarcoma, and Wilms Tumor. Solid tumors can be found in bones, muscles, or organs, and can be sarcomas or carinomas.

It is contemplated that CAR T cells activated following contact by any of the aAPC described herein can be used to treat all types of cancers, including cancers not listed herein. Effective treatment requires that one or more tumor antigens are known or identified for the cancer in question, and that an antigen-binding domain specific for the tumor antigen(s) is identified and cloned. When these conditions are met, one of skill in the art can prepare a CAR, introduce it to a T cell, and activate those T cells using an aAPC as described herein. The identification of a tumor antigen present on a tumor cell can be facilitated by assessing a tumor sample for known tumor antigens, e.g., using fluorescence microscopy or FACS with a panel of anti-tumor antigen antibodies.

Administration

In some embodiments, the methods described herein relate to treating a subject having or diagnosed as having cancer by administering activated CAR T cells. As used herein, a "condition" refers to a cancer, a plasma cell disease or disorder, or an autoimmune disease or disorder. Subjects having a condition can be identified by a physician using current methods of diagnosing the condition. Symptoms and/or complications of the condition, which characterize these conditions and aid in diagnosis are well known in the art and include but are not limited to, fatigue, persistent infections, and persistent bleeding. Tests that may aid in a diagnosis of, e.g. the condition, but are not limited to, blood screening and bone marrow testing, and are known in the art for a given condition. A family history for a condition, or exposure to risk factors for a condition can also aid in determining if a subject is likely to have the condition or in making a diagnosis of the condition.

The CAR T cell compositions described herein can be administered to a subject having or diagnosed as having a condition. In some embodiments, the methods described herein comprise administering an effective amount of activated CAR T cells described herein to a subject in order to alleviate a symptom of the condition. As used herein, "alleviating a symptom of the condition" is ameliorating any condition or symptom associated with the condition. As compared with an equivalent untreated control, such reduction is by at least 5%, 10%, 20%, 40%, 50%, 60%, 80%, 90%, 95%, 99% or more as measured by any standard technique. A variety of means for administering the compositions described herein to subjects are known to those of skill in the art. In one embodiment, the CAR T cell compositions described herein are administered systemically or locally. In a preferred embodiment, the compositions are administered intravenously. In another embodiment, the compositions are administered at the site of a tumor.

The term "effective amount" as used herein refers to the amount of activated CAR T cells needed to alleviate at least one or more symptom of the disease or disorder, and relates to a sufficient amount of the cell preparation or composition to provide the desired effect. The term "therapeutically effective amount" therefore refers to an amount of activated CAR T cells that is sufficient to provide a particular anti-condition effect when administered to a typical subject. An effective amount as used herein, in various contexts, would also include an amount sufficient to delay the development of a symptom of the disease, alter the course of a symptom disease (for example but not limited to, slowing the progression of a condition), or reverse a symptom of the condition. Thus, it is not generally practicable to specify an exact "effective amount". However, for any given case, an appropriate "effective amount" can be determined by one of ordinary skill in the art using only routine experimentation.

Effective amounts, toxicity, and therapeutic efficacy can be evaluated by standard pharmaceutical procedures in cell cultures or experimental animals. The dosage can vary depending upon the dosage form employed and the route of administration utilized. The dose ratio between toxic and therapeutic effects is the therapeutic index and can be expressed as the ratio LD50/ED50. Compositions and methods that exhibit large therapeutic indices are preferred. A therapeutically effective dose can be estimated initially from cell culture assays. Also, a dose can be formulated in animal models to achieve a circulating plasma concentration range that includes the IC50 (i.e., the concentration of activated CAR T cells, which achieves a half-maximal inhibition of symptoms) as determined in cell culture, or in an appropriate animal model. Levels in plasma can be measured, for example, by high performance liquid chromatography. The effects of any particular dosage can be monitored by a suitable bioassay, e.g., assay for bone marrow testing, among others. The dosage can be determined by a physician and adjusted, as necessary, to suit observed effects of the treatment.

In one aspect of the invention, the technology described herein relates to a pharmaceutical composition comprising activated CAR T cells as described herein, and optionally a pharmaceutically acceptable carrier. The active ingredients of the pharmaceutical composition at a minimum comprise activated CAR T cells as described herein. In some embodiments, the active ingredients of the pharmaceutical composition consist essentially of activated CAR T cells as described herein. In some embodiments, the active ingredients of the pharmaceutical composition consist of activated CAR T cells as described herein. Pharmaceutically acceptable carriers for cell-based therapeutic formulations include saline and aqueous buffer solutions, Ringer's solution, and serum component, such as serum albumin, HDL and LDL. The terms such as "excipient," "carrier," "pharmaceutically acceptable carrier" or the like are used interchangeably herein.

In some embodiments, the pharmaceutical composition comprising activated CAR T cells as described herein can be a parenteral dose form. Since administration of parenteral dosage forms typically bypasses the patient's natural defenses against contaminants, the components apart from the CAR T cells themselves are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions. Any of these can be added to the activated CAR T cells preparation prior to administration.

Suitable vehicles that can be used to provide parenteral dosage forms of activated CAR T cells as disclosed herein are well known to those skilled in the art. Examples include, without limitation: saline solution; glucose solution; aqueous vehicles including but not limited to, sodium chloride injection, Ringer's injection, dextrose Injection, dextrose and sodium chloride injection, and lactated Ringer's injection.

Dosage

"Unit dosage form" as the term is used herein refers to a dosage for suitable one administration. By way of example a unit dosage form can be an amount of therapeutic disposed in a delivery device, e.g., a syringe or intravenous drip bag. In one embodiment, a unit dosage form is administered in a single administration. In another, embodiment more than one unit dosage form can be administered simultaneously.

In some embodiments, the activated CAR T cells described herein are administered as a monotherapy, i.e., another treatment for the condition is not concurrently administered to the subject.

A pharmaceutical composition comprising the T cells described herein can generally be administered at a dosage of $10^4$ to $10^9$ cells/kg body weight, in some instances $10^5$ to $10^6$ cells/kg body weight, including all integer values within those ranges. If necessary, T cell compositions can also be administered multiple times at these dosages. The cells can be administered by using infusion techniques that are commonly known in immunotherapy (see, e.g., Rosenberg et al., New Eng. J. of Med. 319:1676, 1988).

In certain aspects, it may be desired to administer activated CAR T cells to a subject and then subsequently redraw blood (or have an apheresis performed), activate T cells therefrom as described herein, and reinfuse the patient with these activated and expanded T cells. This process can be carried out multiple times every few weeks. In certain aspects, T cells can be activated from blood draws of from 10 cc to 400 cc. In certain aspects, T cells are activated from blood draws of 20 cc, 30 cc, 40 cc, 50 cc, 60 cc, 70 cc, 80 cc, 90 cc, or 100 cc.

Modes of administration can include, for example intravenous (i.v.) injection or infusion. The compositions described herein can be administered to a patient transarterially, intratumorally, intranodally, or intramedullary. In some embodiments, the compositions of T cells may be injected directly into a tumor, lymph node, or site of infection. In one embodiment, the CAR T cell compositions are administered into a body cavity or body fluid (e.g., ascites, pleural fluid, peritoneal fluid, or cerebrospinal fluid).

In a particular exemplary aspect, subjects may undergo leukapheresis, wherein leukocytes are collected, enriched, or depleted ex vivo to select and/or isolate the cells of interest, e.g., T cells. These T cell isolates can be expanded by contact with an aAPC as described herein, e.g., an aAPC expressing anti-CD28 and anti-CD3 CDRs as described herein and treated such that one or more CAR constructs of the invention may be introduced, thereby creating a CAR T cell. Subjects in need thereof can subsequently undergo standard treatment with high dose chemotherapy followed by peripheral blood stem cell transplantation. Following or concurrent with the transplant, subjects can receive an infusion of the expanded CAR T cells. In one embodiment, expanded cells are administered before or following surgery.

In some embodiments, lymphodepletion is performed on a subject prior to administering one or more CAR T cell as described herein. In such embodiments, the lymphodepletion can comprise administering one or more of melphalan, Cytoxan, cyclophosphamide, and fludarabine.

The dosage of the above treatments to be administered to a patient will vary with the precise nature of the condition being treated and the recipient of the treatment. The scaling of dosages for human administration can be performed according to art-accepted practices.

In some embodiments, a single treatment regimen is required. In others, administration of one or more subsequent doses or treatment regimens can be performed. For example, after treatment biweekly for three months, treatment can be repeated once per month, for six months or a year or longer. In some embodiments, no additional treatments are administered following the initial treatment.

The dosage of a composition as described herein can be determined by a physician and adjusted, as necessary, to suit observed effects of the treatment. With respect to duration and frequency of treatment, it is typical for skilled clinicians to monitor subjects in order to determine when the treatment is providing therapeutic benefit, and to determine whether to administer further cells, discontinue treatment, resume treatment, or make other alterations to the treatment regimen. The dosage should not be so large as to cause adverse side effects, such as cytokine release syndrome. Generally, the dosage will vary with the age, condition, and sex of the patient and can be determined by one of skill in the art. The dosage can also be adjusted by the individual physician in the event of any complication.

Combinational Therapy

The activated CAR T cells described herein can be used in combination with other known agents and therapies. Administered "in combination," as used herein, means that two (or more) different treatments are delivered to the subject during the course of the subject's affliction with the disorder, e.g., the two or more treatments are delivered after the subject has been diagnosed with the disorder and before the disorder has been cured or eliminated or treatment has ceased for other reasons. In some embodiments, the delivery of one treatment is still occurring when the delivery of the second begins, so that there is overlap in terms of administration. This is sometimes referred to herein as "simultaneous" or "concurrent delivery." In other embodiments, the delivery of one treatment ends before the delivery of the other treatment begins. In some embodiments of either case, the treatment is more effective because of combined administration. For example, the second treatment is more effective, e.g., an equivalent effect is seen with less of the second treatment, or the second treatment reduces symptoms to a greater extent, than would be seen if the second treatment were administered in the absence of the first treatment, or the analogous situation is seen with the first treatment. In some embodiments, delivery is such that the reduction in a symptom, or other parameter related to the disorder is greater than what would be observed with one treatment delivered in the absence of the other. The effect of the two treatments can be partially additive, wholly additive, or greater than additive. The delivery can be such that an effect of the first treatment delivered is still detectable when the second is delivered. The activated CAR T cells described herein and the at least one additional therapeutic agent can be administered simultaneously, in the same or in separate compositions, or sequentially. For sequential administration, the CAR-expressing cell described herein can be administered first, and the additional agent can be administered second, or the order of administration can be reversed. The CAR T therapy and/or other therapeutic agents, procedures or modalities can be administered during periods of active disorder, or during a period of remission or less active disease. The CAR T therapy can be administered before another treatment, concurrently with the treatment, post-treatment, or during remission of the disorder.

When administered in combination, the activated CAR T cells and the additional agent (e.g., second or third agent), or all, can be administered in an amount or dose that is higher, lower or the same as the amount or dosage of each agent used individually, e.g., as a monotherapy. In certain embodiments, the administered amount or dosage of the activated CAR T cells, the additional agent (e.g., second or third agent), or all, is lower (e.g., at least 20%, at least 30%, at least 40%, or at least 50%) than the amount or dosage of each agent used individually. In other embodiments, the amount or dosage of the activated CAR T cells, the additional agent (e.g., second or third agent), or all, that results in a desired effect (e.g., treatment of cancer) is lower (e.g., at least 20%, at least 30%, at least 40%, or at least 50% lower) than the amount or dosage of each agent individually required to achieve the same therapeutic effect. In further embodiments, the activated CAR T cells described herein can be used in a treatment regimen in combination with surgery, chemotherapy, radiation, an mTOR pathway inhibitor, immunosuppressive agents, such as cyclosporin, azathioprine, methotrexate, mycophenolate, and FK506, antibodies, or other immunoablative agents such as CAMPATH, anti-CD3 antibodies or other antibody therapies, cytoxin, fludarabine, rapamycin, mycophenolic acid, steroids, FR901228, cytokines, or a peptide vaccine, such as that described in Izumoto et al. 2008 J Neurosurg 108:963-971.

In one embodiment, the activated CAR T cells described herein can be used in combination with a checkpoint inhibitor. Exemplary checkpoint inhibitors include anti-PD-1 inhibitors (Nivolumab, MK-3475, Pembrolizumas, Pidilizumab, AMP-224, AMP-514), anti-CTLA4 inhibitors (Ipilimumab and Tremelimumab), anti-PDL1 inhibitors (Atezolizumab, Avelomab, MSB0010718C, MEDI4736, and MPDL3280A), and anti-TIM3 inhibitors.

In one embodiment, the activated CAR T cells described herein can be used in combination with a chemotherapeutic agent. Exemplary chemotherapeutic agents include an anthracycline (e.g., doxorubicin (e.g., liposomal doxorubicin)), a vinca alkaloid (e.g., vinblastine, vincristine, vindesine, vinorelbine), an alkylating agent (e.g., cyclophosphamide, decarbazine, melphalan, ifosfamide, temozolomide), an immune cell antibody (e.g., alemtuzamab, gemtuzumab, rituximab, tositumomab), an antimetabolite (including, e.g., folic acid antagonists, pyrimidine analogs, purine analogs and adenosine deaminase inhibitors (e.g., fludarabine)), an mTOR inhibitor, a TNFR glucocorticoid induced TNFR related protein (GITR) agonist, a proteasome inhibitor (e.g., aclacinomycin A, gliotoxin or bortezomib), an immunomodulator such as thalidomide or a thalidomide derivative (e.g., lenalidomide). General chemotherapeutic agents considered for use in combination therapies include anastrozole (Arimidex®), bicalutamide (Casodex®), bleomycin sulfate (Blenoxane®), busulfan (Myleran®), busulfan injection (Busulfex®), capecitabine (Xeloda®), N4-pentoxycarbonyl-5-deoxy-5-fluorocytidine, carboplatin (Paraplatin®), carmustine (BiCNU®), chlorambucil (Leukeran®), cisplatin (Platinol®), cladribine (Leustatin®), cyclophosphamide (Cytoxan® or Neosar®), cytarabine, cytosine arabinoside (Cytosar-U®), cytarabine liposome injection (DepoCyt®), dacarbazine (DTIC-Dome®), dactinomycin (Actinomycin D, Cosmegan), daunorubicin hydrochloride (Cerubidine®), daunorubicin citrate liposome injection (DaunoXome®), dexamethasone, docetaxel (Taxotere®), doxorubicin hydrochloride (Adriamycin®, Rubex®), etoposide (Vepesid®), fludarabine phosphate (Fludara®), 5-fluorouracil (Adrucil®, Efudex®), flutamide (Eulexin®), tezacitibine, Gemcitabine (difluorodeoxycitidine), hydroxyurea (Hydrea®), Idarubicin (Idamycin®), ifosfamide (IFEX®), irinotecan (Camptosar®), L-asparaginase (ELSPAR®), leucovorin calcium, melphalan (Alkeran®), 6-mercaptopurine (Purinethol®), methotrexate (Folex®), mitoxantrone (Novantrone®), mylotarg, paclitaxel (Taxol®), phoenix (Yttrium90/MX-DTPA), pentostatin, polifeprosan 20 with carmustine implant (Gliadel®), tamoxifen citrate (Nolvadex®), teniposide (Vumon®), 6-thioguanine, thiotepa, tirapazamine (Tirazone®), topotecan hydrochloride for injection (Hycamptin®), vinblastine (Velban®), vincristine (Oncovin®), and vinorelbine (Navelbine®). Exemplary alkylating agents include, without limitation, nitrogen mustards, ethylenimine derivatives, alkyl sulfonates, nitrosoureas and triazenes): uracil mustard (Aminouracil Mustard®, Chlorethaminacil®, Demethyldopan®, Desmethyldopan®, Haemanthamine®, Nordopan®, Uracil nitrogen Mustard®, Uracillost®, Uracilmostaza®, Uramustin®, Uramustine®), chlormethine (Mustargen®), cyclophosphamide (Cytoxan®, Neosar®, Clafen®, Endoxan®, Procytox®, Revimmune™), ifosfamide (Mitoxana®), melphalan (Alkeran®), Chlorambucil (Leukeran®), pipobroman (Amedel®, Vercyte®), triethylenemelamine (Hemel®, Hexalen®, Hexastat®), triethylenethiophosphoramine, Temozolomide (Temodar®), thiotepa (Thioplex®), busulfan (Busilvex®, Myleran®), carmustine (BiCNU®), lomustine (CeeNU®), streptozocin (Zanosar®), and Dacarbazine (DTIC-Dome®). Additional exemplary alkylating agents include, without limitation, Oxaliplatin (Eloxatin®); Temozolomide (Temodar® and Temodal®); Dactinomycin (also known as actinomycin-D, Cosmegen®); Melphalan (also known as L-PAM, L-sarcolysin, and phenylalanine mustard, Alkeran®); Altretamine (also known as hexamethylmelamine (HMM), Hexalen®); Carmustine (BiCNU®); Bendamustine (Treanda®); Busulfan (Busulfex® and Myleran®); Carboplatin (Paraplatin®); Lomustine (also known as CCNU, CeeNU®); Cisplatin (also known as CDDP, Platinol® and Platinol®-AQ); Chlorambucil (Leukeran®); Cyclophosphamide (Cytoxan® and Neosar®); Dacarbazine (also known as DTIC, DIC and imidazole carboxamide, DTIC-Dome®); Altretamine (also known as hexamethylmelamine (HMM), Hexalen®); Ifosfamide (Ifex®); Prednumustine; Procarbazine (Matulane®); Mechlorethamine (also known as nitrogen mustard, mustine and mechloroethamine hydrochloride, Mustargen®); Streptozocin (Zanosar®); Thiotepa (also known as thiophosphoamide, TESPA and TSPA, Thioplex®); Cyclophosphamide (Endoxan®, Cytoxan®, Neosar®, Procytox®, Revimmune®); and Bendamustine HCl (Treanda®). Exemplary mTOR inhibitors include, e.g., temsirolimus; ridaforolimus (formally known as deferolimus, (1R,2R,45)-4-[(2R)-2 [(1R,95,125,15R,16E,18R,19R,21R,235,24E,26E,28Z,305, 325,35R)-1,18-dihydroxy-19,30-dimethoxy-15,17,21,23, 29,35-hexamethyl-2,3,10,14,20-pentaoxo-11,36-dioxa-4-azatricyclo[30.3.1.04'9] hexatriaconta-16,24,26,28-tetraen-12-yl]propyl]-2-methoxycyclohexyl dimethylphosphinate, also known as AP23573 and MK8669, and described in PCT Publication No. WO 03/064383); everolimus (Afinitor® or RADOO1); rapamycin (AY22989, Sirolimus®); simapimod (CAS 164301-51-3); emsirolimus, (5-{2,4-Bis[(35,)-3-methylmorpholin-4-yl]pyrido[2,3-(i]pyrimidin-7-yl}-2-methoxyphenyl)methanol (AZD8055); 2-Amino-8-[iraw5,-4-(2-hydroxyethoxy)cyclohexyl]-6-(6-methoxy-3-pyridinyl)-4-methyl-pyrido[2,3-JJpyrimidin-7(8H)-one (PF04691502, CAS 1013101-36-4); and N2-[1,4-dioxo-4-[[4-(4-oxo-8-phenyl-4H-1-benzopyran-2-yl)morpholinium-4-yl]methoxy]butyl]-L-arginylglycyl-L-a-aspartylL-serine-(SEQ ID NO: 39), inner salt (SF1126, CAS 936487-67-1), and XL765. Exemplary immunomodulators include, e.g., afutuzumab (available from Roche®); pegfilgrastim (Neulasta®); lenalidomide (CC-5013, Revlimid®); thalidomide (Thalomid®), actimid (CC4047); and IRX-2 (mixture of human cytokines including interleukin 1, interleukin 2, and interferon γ, CAS 951209-71-5, available from IRX Therapeutics). Exemplary anthracyclines include, e.g., doxorubicin (Adriamycin® and Rubex®); bleomycin (Lenoxane®); daunorubicin (dauorubicin hydrochloride, daunomycin, and rubidomycin hydrochloride, Cerubidine®); daunorubicin liposomal (daunorubicin citrate liposome, DaunoXome®); mitoxantrone (DHAD, Novantrone®); epirubicin (Ellence™); idarubicin (Idamycin®, Idamycin PFS®); mitomycin C (Mutamycin®); geldanamycin; herbimycin; ravidomycin; and desacetylravidomycin. Exemplary vinca alkaloids include, e.g., vinorelbine tartrate (Navelbine®), Vincristine (Oncovin®), and Vindesine (Eldisine®)); vinblastine (also known as vinblastine sulfate, vincaleukoblastine and VLB, Alkaban-AQ® and Velban®); and vinorelbine (Navelbine®). Exemplary proteosome inhibitors include bortezomib (Velcade®); carfilzomib (PX-171-007, (5)-4-Methyl-N4(5)-1-(((5)-4-methyl-1-((R)-2-methyloxiran-2-yl)-1-oxopentan-2-yl)amino)-1-oxo-3-phenylpropan-2-yl)-2-((5,)-2-(2-morpholinoacetamido)-4-phenylbutanamido)-pentanamide); marizomib (NPT0052); ixazomib citrate (MLN-9708); delanzomib (CEP-18770); and O-Methyl-N-[(2-methyl-5-thiazolyl)carbonyl]-L-seryl-O-methyl-N-[(11S')-2-[(2R)-2-methyl-2-oxiranyl]-2-oxo-1-(phenylmethyl)ethyl]-L-serinamide (ONX-0912).

One of skill in the art can readily identify a chemotherapeutic agent of use (e.g. see Physicians' Cancer Chemotherapy Drug Manual 2014, Edward Chu, Vincent T. DeVita Jr., Jones & Bartlett Learning; Principles of Cancer Therapy, Chapter 85 in Harrison's Principles of Internal Medicine, 18th edition; Therapeutic Targeting of Cancer Cells: Era of Molecularly Targeted Agents and Cancer Pharmacology, Chs. 28-29 in Abeloff's Clinical Oncology, 2013 Elsevier; and Fischer D S (ed): The Cancer Chemotherapy Handbook, 4th ed. St. Louis, Mosby-Year Book, 2003).

In an embodiment, activated CAR T cells described herein are administered to a subject in combination with a molecule that decreases the a molecule targeting GITR and/or modulating GITR functions, a molecule that decreases the Treg cell population, an mTOR inhibitor, a GITR agonist, a kinase inhibitor, a non-receptor tyrosine kinase inhibitor, a CDK4 inhibitor, and/or a BTK inhibitor.

Efficacy

The efficacy of activated CAR T cells in, e.g. the treatment of a condition described herein, or to induce a response as described herein (e.g. a reduction in cancer cells) can be determined by the skilled clinician. However, a treatment is considered "effective treatment," as the term is used herein, if one or more of the signs or symptoms of a condition described herein is altered in a beneficial manner, other clinically accepted symptoms are improved, or even ameliorated, or a desired response is induced e.g., by at least 10% following treatment according to the methods described herein. Efficacy can be assessed, for example, by measuring a marker, indicator, symptom, and/or the incidence of a condition treated according to the methods described herein or any other measurable parameter appropriate. Treatment according to the methods described herein can reduce levels of a marker or symptom of a condition, e.g. by at least 10%, at least 15%, at least 20%, at least 25%, at least 30%, at least 40%, at least 50%, at least 60%, at least 70%, at least 80% or at least 90% or more.

Efficacy can also be measured by a failure of an individual to worsen as assessed by hospitalization, or need for medical interventions (i.e., progression of the disease is halted). Methods of measuring these indicators are known to those of skill in the art and/or are described herein.

Treatment includes any treatment of a disease in an individual or an animal (some non-limiting examples include a human or an animal) and includes: (1) inhibiting the disease, e.g., preventing a worsening of symptoms (e.g. pain or inflammation); or (2) relieving the severity of the disease, e.g., causing regression of symptoms. An effective amount for the treatment of a disease means that amount which, when administered to a subject in need thereof, is sufficient to result in effective treatment as that term is defined herein, for that disease. Efficacy of an agent can be determined by assessing physical indicators of a condition or desired response. It is well within the ability of one skilled in the art to monitor efficacy of administration and/or treatment by measuring any one of such parameters, or any combination of parameters. Efficacy of a given approach can be assessed in animal models of a condition described herein, for example treatment of ALL. When using an experimental animal model, efficacy of treatment is evidenced when a statistically significant change in a marker is observed.

All patents and other publications; including literature references, issued patents, published patent applications, and co-pending patent applications; cited throughout this application are expressly incorporated herein by reference for the purpose of describing and disclosing, for example, the methodologies described in such publications that might be used in connection with the technology described herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure. Moreover, due to biological functional equivalency considerations, some changes can be made in protein structure without affecting the biological or chemical action in kind or amount. These and other changes can be made to the disclosure in light of the detailed description. All such modifications are intended to be included within the scope of the appended claims.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

The technology described herein is further illustrated by the following examples which in no way should be construed as being further limiting.

Some embodiments of the technology described herein can be defined according to any of the following numbered paragraphs:

1. An artificial antigen presenting cell (aAPC) comprising:
    a first chimeric stimulatory receptor (CSR) that binds specifically with a first co-stimulatory polypeptide; and a second CSR that binds specifically a second co-stimulatory polypeptide.
2. An artificial antigen presenting cell (aAPC) comprising:
    a first chimeric stimulatory receptor (CSR) that binds specifically with CD3; and
    a second CSR that binds specifically with CD28.
3. The aAPC of either paragraph 1 or 2, wherein the aAPC has been engineered to lack an expressible LDLR gene.
4. The aAPC of any of paragraphs 1-3, wherein the aAPC comprises a deletion in the native LDLR-encoding nucleic acid sequence.
5. The aAPC of any of paragraphs 1-3, wherein the aAPC comprises a deletion of the native LDLR-encoding nucleic acid sequence.
6. The aAPC of any of paragraphs 1-5, wherein the aAPC is viable but non-dividing.
7. The aAPC of any of paragraphs 1-6, wherein the aAPC has been gamma-irradiated.
8. The aAPC of any of paragraphs 1-7, further comprising a T-cell target molecule.
9. The aAPC of paragraph 8, wherein the T-cell target molecule is CD19, BCMA, CD37, SLAMF7, EGFR, or EGFR variant III.
10. The aAPC of paragraph 8 or 9, wherein the T-cell target molecule is CD19.
11. The aAPC of any of paragraphs 8-10, wherein the T-cell target molecule is any molecule that can be targeted by a CAR T cell.
12. The aAPC of any of paragraphs 1-11, wherein the first and second CSRs are expressed on the cell surface of the aAPC.
13. The aAPC of any of paragraphs 1-12, wherein the first and second CSRs are constitutively expressed.
14. The aAPC of any of paragraphs 1-13, wherein the first and second CSRs are encoded by a first recombinant nucleic acid sequence and a second recombinant nucleic acid sequence, respectively.
15. The aAPC of paragraph 14, wherein the sequence encoding the first and/or second CSR is operatively linked to a constitutive promoter.
16. The aAPC of paragraph 15, wherein the constitutive promoter is EF1-α.
17. The aAPC of any of paragraphs 1-16, wherein the aAPC is a human cell.
18. The aAPC of any of paragraphs 1-17, wherein the aAPC is engineered from an erythromyeloid cell.
19. The aAPC of paragraph 18, wherein the erthromyeloid cell is a K562 cell.
20. The aAPC of any of paragraphs 1-19, wherein the first and second CSRs bind specifically with human CD3 and CD28, respectively.
21. The aAPC of any of paragraphs 1 and 3-19, wherein the first CSR binds specifically with 4-1BBL, and the second CSR binds specifically with OX40L.
22. A method of expanding or activating a T cell, the method comprising contacting the aAPC of any of paragraphs 1-21 with a T cell.
23. A method of treating a cancer, a plasma cell disease or disorder, or an autoimmune disease or disorder in a subject in need thereof, the method comprising:
    contacting the aAPC of any of paragraphs 1-21 with a CAR T cell, thereby activating the CAR T cell; and administering the activated CAR T cell to the subject.
24. The method of paragraph 22 or 23, wherein the contacting step occurs in vitro.
25. The method of paragraph 22 or 23, wherein the contacting step occurs in suspension.
26. A composition comprising the aAPC of any of paragraphs 1-21 and a T cell.
27. The composition of paragraph 26, wherein the T cell is a CAR T cell.
28. A composition comprising the activated CAR T cells of the method of any of paragraphs 23-25, formulated for the treatment of cancer.
29. The composition of paragraph 28, further comprising a pharmaceutically acceptable carrier.
30. The method of any of paragraphs 23-25, wherein the cancer is a leukemia, a lymphoma, multiple myeloma, or a solid tumor.
31. The method of paragraph 30, wherein the leukemia is acute lymphocytic leukemia (ALL) or chronic lymphocytic leukemia (CLL).
32. The method of paragraph 30, wherein the lymphoma is follicular lymphoma or diffuse large B cell lymphoma (DLBCL).

EXAMPLES

Described herein is a novel technology to induce T cell proliferation and/or activation. These methods described in the following examples utilize gamma-irradiated artificial antigen-presenting cells (aAPCs) genetically engineered to constitutively express chimeric stimulatory receptors (CSR) specifically recognizing both CD3 and CD28 (FIG. 1). The feasibility and efficacy of aAPC in which antibody constructs binding both molecules are loaded onto the aAPC surface are demonstrated herein; the genetically engineered form described bypasses the need for clinical-grade soluble antibodies as accessory reagents.

Further contemplated herein is the use of the described technology for commercial applications in cellular immunotherapy.

CD3/CD28 microspheres to expand T cells are very costly ($6,000 per vial), representing a significant expense in cell manufacturing. Moreover, the process of "bead removal" prior to aliquotting into unit doses for cryopreservation and final use, represents an additional onerous step in T cell manufacturing that poses high contamination risks and increases the production costs. Microspheres can also provide continuous stimulation to T cells in culture which, accompanied by the presence of high concentrations of exogenous IL-2, may induce T cell exhaustion, which would be counter-productive in anti-cancer therapies.

In contrast, the aAPCs described herein can be manufactured as a clinical (GMP) grade reagent, expanded from an initial master cell bank and cryopreserved in production batches following gamma-irradiation to render them nondividing. More importantly, aAPC of this nature can be readily used after thawing, do not proliferate in culture, and can be completely eliminated if an additional target molecule is co-expressed on their surface (e.g., CD19 as target for CART19 cells). aAPCs described in this example and elsewhere herein, are engineered to express CSRs, which bypasses the need to use clinical grade antibodies. There is also no need for additional steps to purify T-cell products at the end of manufacturing runs, making these aAPC an attractive and cost-effective new technology in the production of engineered T cells for clinical therapies.

The methods described herein can be utilized to treat cancer patients with leukemias such as ALL or CLL, with lymphoma (follicular or DLBCL), or with multiple myeloma, each of which have been successfully treated with CART cell therapies. It is further contemplated that the patient population can be expanded to patients with solid tumors.

Example 1

Methods

Production of aAPC Co-Expressing CD3- and CD28-Targeting CSR (Chimeric Stimulatory Receptors).

CSR-CD3 (derived from an anti-CD3 Mab) and CSR-CD28 (from an anti-CD28 MAb) sequences are cloned into lentiviral vector (pMGH vector). Cells to be used as aAPC (K562, erythromyeloid cell line) are transduced with lentiviruses encoding pMGH-CSR-CD3-T2A-GFP and pMGH-CSR-CD28-T2A-mCherry. The fluorescent reporters will be used to FACS sort the aAPC that co-express both CSRs. Fluorescent reporters have no effect on the stability of the aAPC system. aAPC are expanded, gamma-irradiated and cryopreserved (5-10e6 cells/vial). aAPC are validated (cell viability and cell numbers, and FACS analysis for the expression of CSR-CD3 and CSR-CD28 post-thawing and at multiple time points during culture).

Analysis of Engineered T-Cell Products Manufactured with aAPC.

Figure 2:
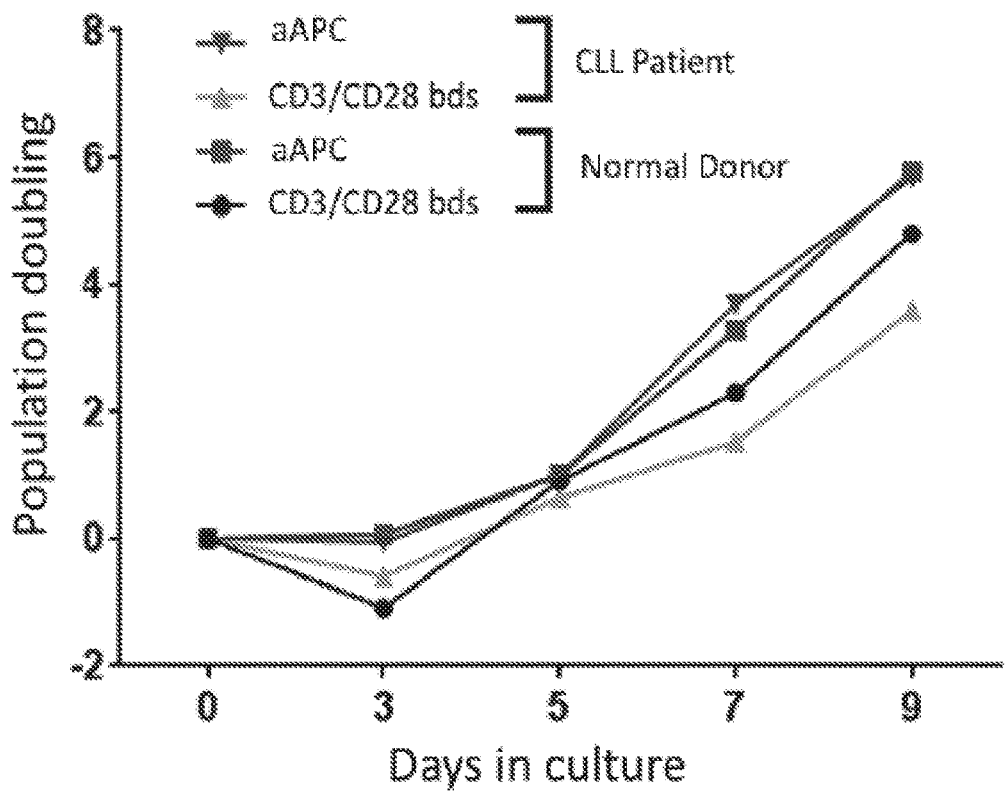
FIG. 2 depicts a graph of population doubling of purified T cells from a normal donor and a chronic lymphocytic leukemia (CLL) patient set in culture at day zero with either CD3/CD28 microspheres (beads) or with artificial APC (aAPC) loaded with anti-CD3 and anti-CD28 monoclonal antibodies. Population doubling of T cells was calculated for days 3, 5, 7, and 9 of culture.

The efficiency of aAPC to stimulate primary T cells is determined, e.g., by measuring T-cell growth with expansion curves as shown in FIG. 2. Briefly, T cells are seeded at day 0 at a 3:1 ratio (beads:T cells) and at different aAPC:T cell ratios (optimal ratio will be determined). Total cell numbers and mean cell volumes are measured at days 3, 5, 7, and 9 using a Multisizer™ 3 Coulter Counter (Beckman Coulter), and cellular viability is determined by staining with Acridine Orange/PropidiumIodide exclusion dye using a Luna-FL™ Cell Counter (Logos Biosystems).

Analysis of transduction efficiency of primary T cells co-cultured with aAPC. FACS analysis is performed to determine transduction efficiency. For example, when using the CAR19 lentiviral vector (recognizing CD19), streptavidin-conjugated protein L can be used to detect the single chain variable fragment of the CAR.

Potency tests of T cell products manufactured in the presence of aAPC; comparison with products made with CD3/CD28 microspheres. Functional characteristics are measured on transduced T cells upon re-stimulation with target-antigen (eg. CD19, BCMA, etc.) expressing cells:

Proliferative capacity (CFSE dilution and absolute cell numbers by FACS using fluorescently-labeled counting beads).

Cytokine production (10-Piex Luminex Assays).

Target-cell killing capacity (Bioluminesce analysis of target cells in vitro or animal model system to track both tumor and engineered T cells infused in immunodeficient mice).

Cell degranulation analysis (CD107a release assay in response to target cells, measured by FACS).

CSR Construction

The CD3 CSR (OKT3) comprised, in addition to an ScFv that binds CD3:

CD8 hinge and TM domain;

CD3ζ (5 first aminoacids);

T2A; and

GFP.

The CD28 CSR (9.3) comprised in addition to an ScFv that binds CD28:

CD28 hinge—TM—ICD;

T2A; and mCherry.

Figure 4:
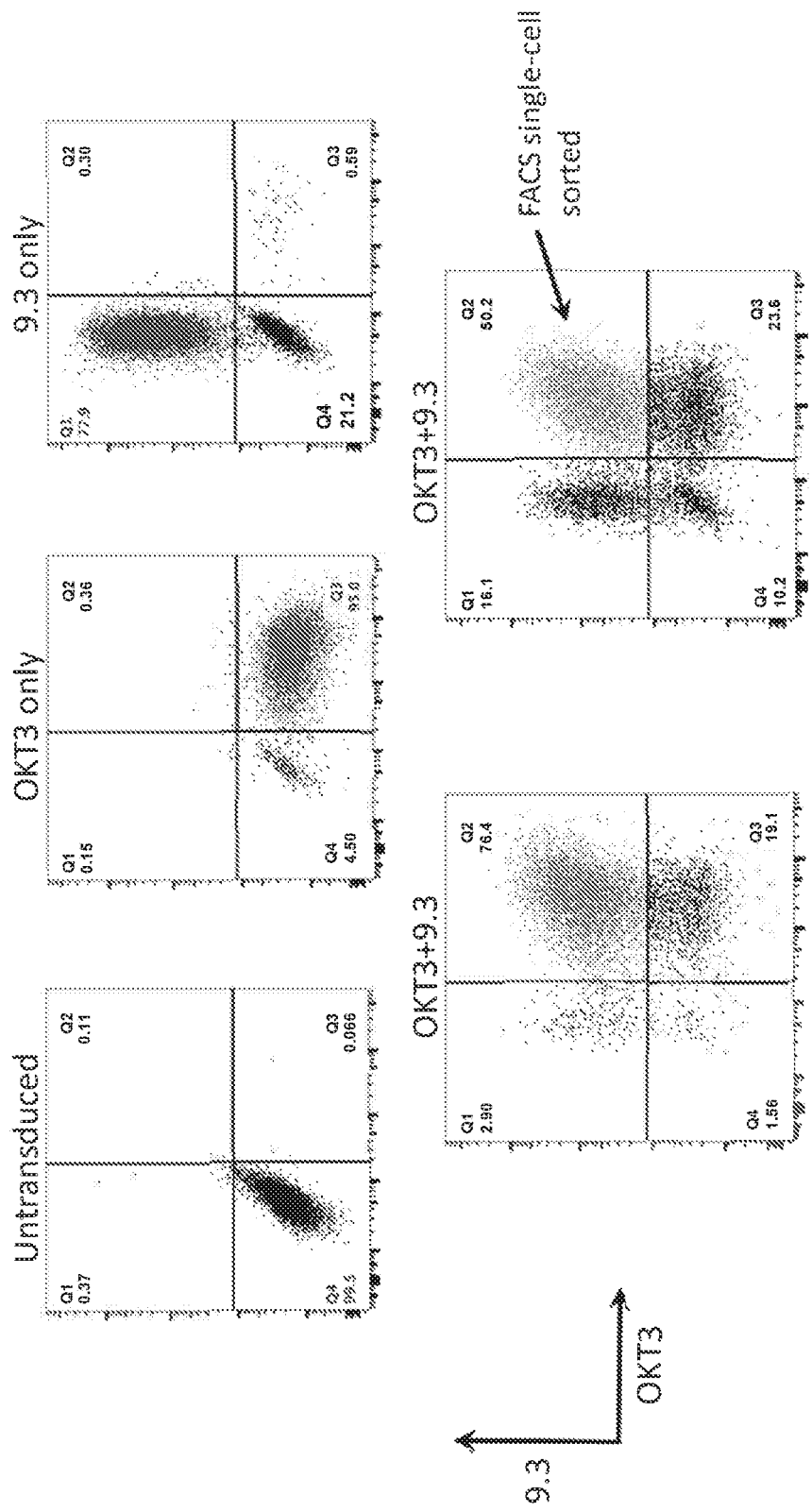
FIG. 4 depicts FACS results demonstrating that aAPCs express both OKT3 and 9.3 CSRs.
Figure 5:
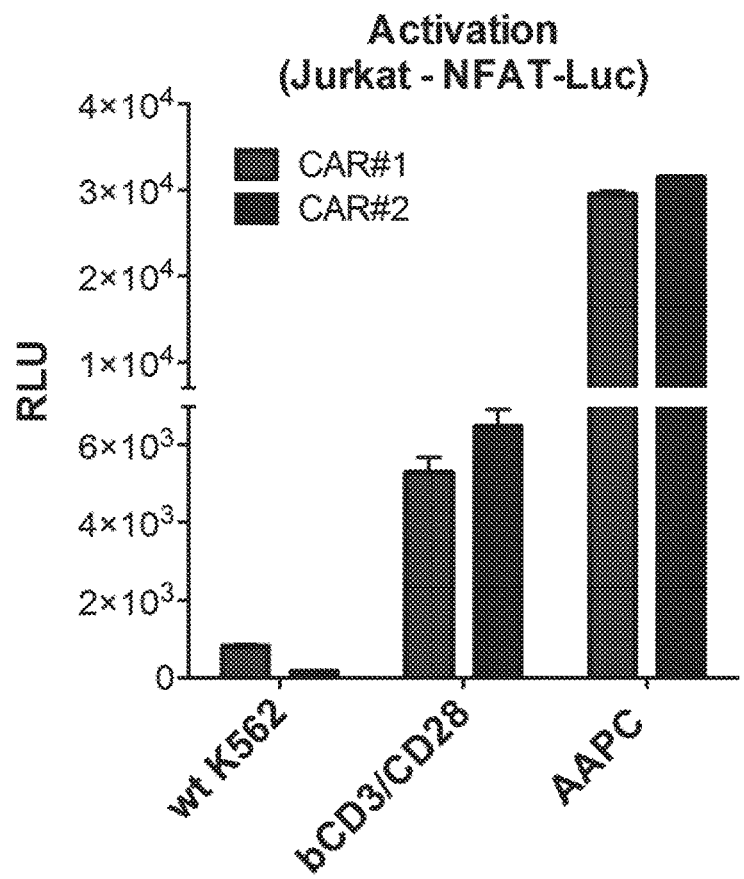
FIG. 5 is a graph of T cell activation demonstrating that aAPCs induce T-cell activation (NFAT).
Figure 6:
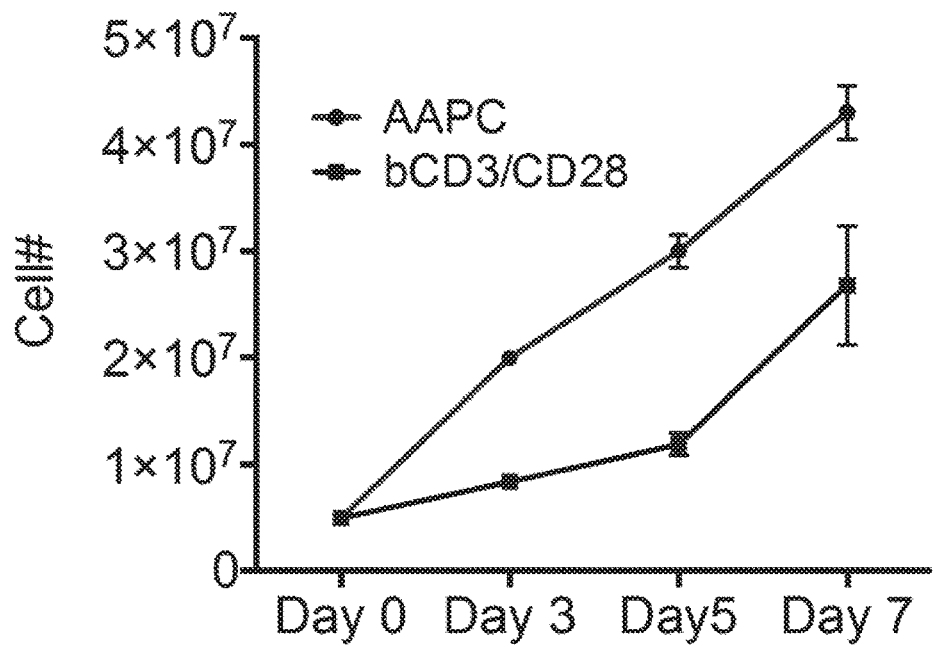
FIG. 6 is a graph of T cell growth demonstrating T-cell expansion using aAPCs.
Figure 7:
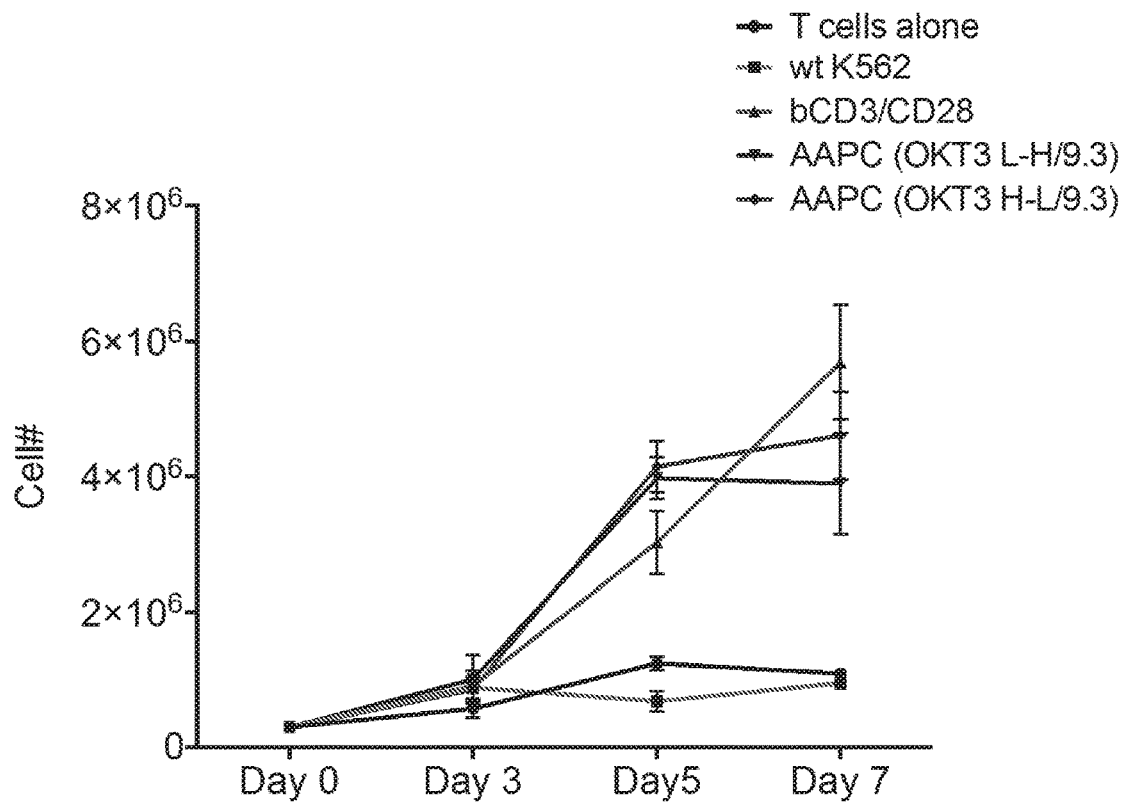
FIG. 7 is a graph of T cell growth demonstrating T-cell expansion using aAPCs v. anti-CD3 and anti-CD28 antibody-conjugated beads (bCD3/CD28).
Figure 8:
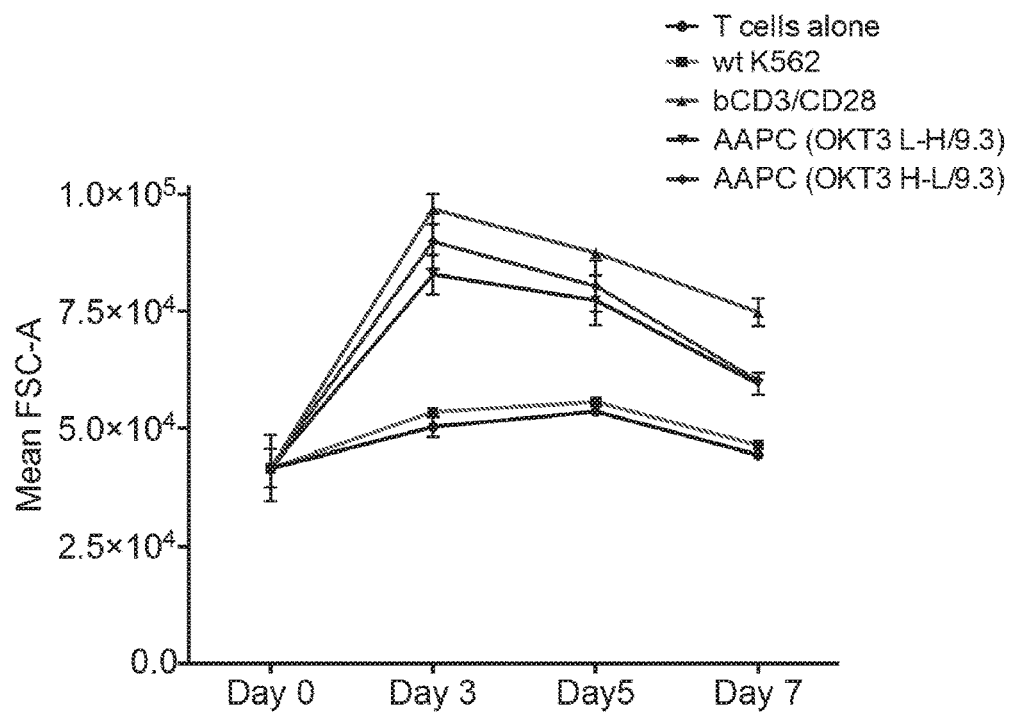
FIG. 8 is a graph of T-cell size analysis during culture with aAPCs v. bCD3/CD28 (3 normal donors).

Artificial Antigen Presenting Cells (aAPC) were designed to express two CSR (transgene structure shown in FIG. 1): CD3 CSR (OKT3 in both scFv configurations heavy-light and light-heavy). Reporter gene=GFP. CD28 CSR (clone 9.3 in light-heavy scFv configuration). Reporter gene=mCherry. Three lentiviruses were generated:

pMGH43=CD3 CSR (L-H)

pMGH44=CD3 CSR (H-L)

pMGH45—CD28 CSR (L-H)

aAPCs were single-cell sorted based on GFP and mCherry expression (FIG. 4), expanded and cryopreserved. Jurkat cells (a human T-cell line), expressing a luciferase gene under the control of an NFAT promoter were transduced with two different CAR-encoding lentiviruses. Jurkat cells were co-cultured for 18 hours with wild-type K562 cells (negative control), Dynabeads coated with anti-CD3 and anti-CD28 antibodies (positive control), and aAPCs (expressing both CD3 and CD28 CSRs). aAPCs induced higher activation of the Jurkat cells than Dynabeads as determined by the higher relative luminescence units (RLU) (FIG. 5). Surprisingly, aAPCs (expressing CD3+CD28 CSRs) promote more human primary T-cell growth than the conventional method using Dynabeads (FIG. 6; 1 donor and FIG. 7; 3 normal donors). Human T cells expand during activation with aAPCs during the first three days of culture, and subsequently contract following a similar pattern as when T cells are stimulated with Dynabeads (FIG. 8).

Generation and Validation of LDLR KO aAPCs Using Electroporated K562 Cells

Expression of the low-density lipoprotein receptor (LDLR) on cells is critical for the attachment and entrance of VSV-g-pseudotyped viruses. Using CRISPR, we knocked out the expression of the LDLR on K562 cells to be used as artificial antigen presenting cells (aAPC) to enhance the transduction efficiency of genetically-modified cells using a lentiviral system. The KO was validated as follows:

Nucleases Analyzed:
SpCas9
SpCas9-H1 (High fidelity)
AsCpf1
LbCpf1
RNA Guides Analyzed:
9→SpCas9
4→Cpf1
Total number of samples/cultures=54+24=78
Cas9: 2 nucleases×9 guides=18→In triplicates: 18×3=54
Cpf1: 2 nucleases×4 guides=8→In triplicates: 8×3=24
Validation of indels in extracted genomic DNA of K562 cells:
T7E1 assay (denature DNA—Annealing—Gel electrophoresis—Calculation)
WT:digested DNA bands
FACS (LDLR-PE surface staining)

The CRISPR technology was used to disrupt the expression of the LDLR on aAPCs. Four DNA nucleases (wt Cas9, Cas9 HF1, AsCpf1, and LbCpf1) and ten different RNA guides were tested. FIG. 9, top panel shows the results from a T7E1 assay indicating the percent disruption or modification level achieved on the LDLR gene using a specific combination of nuclease and guide RNA. The highest % disruption efficiencies were obtained using the following combinations:

1. Cas9 (both wt and HF1)+Exon1-Site1 guide RNA
2. Cpf1 (both As and Lb)+Exon1-Site1 guide RNA
3. Cpf1 (both As and Lb)+Exon3-Site2 guide RNA The results from the T7E1 assay were validated by flow cytometry, staining cells with an anti-human LDLR-PE antibody (FIG. 9, bottom panel). FACS controls were cells electroporated with nuclease-encoding DNA without guide RNA.

Figure 10:
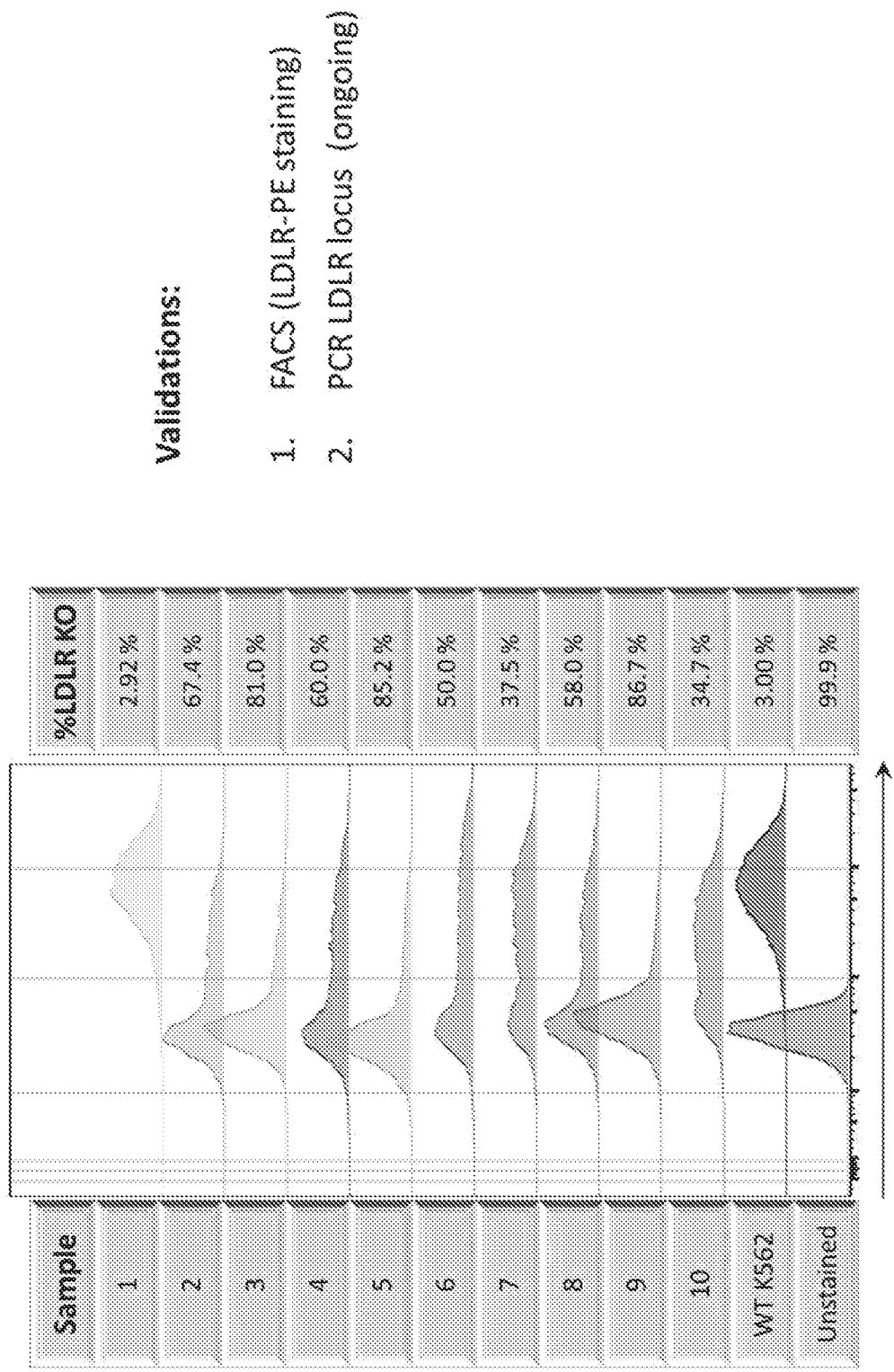
Figure 11:
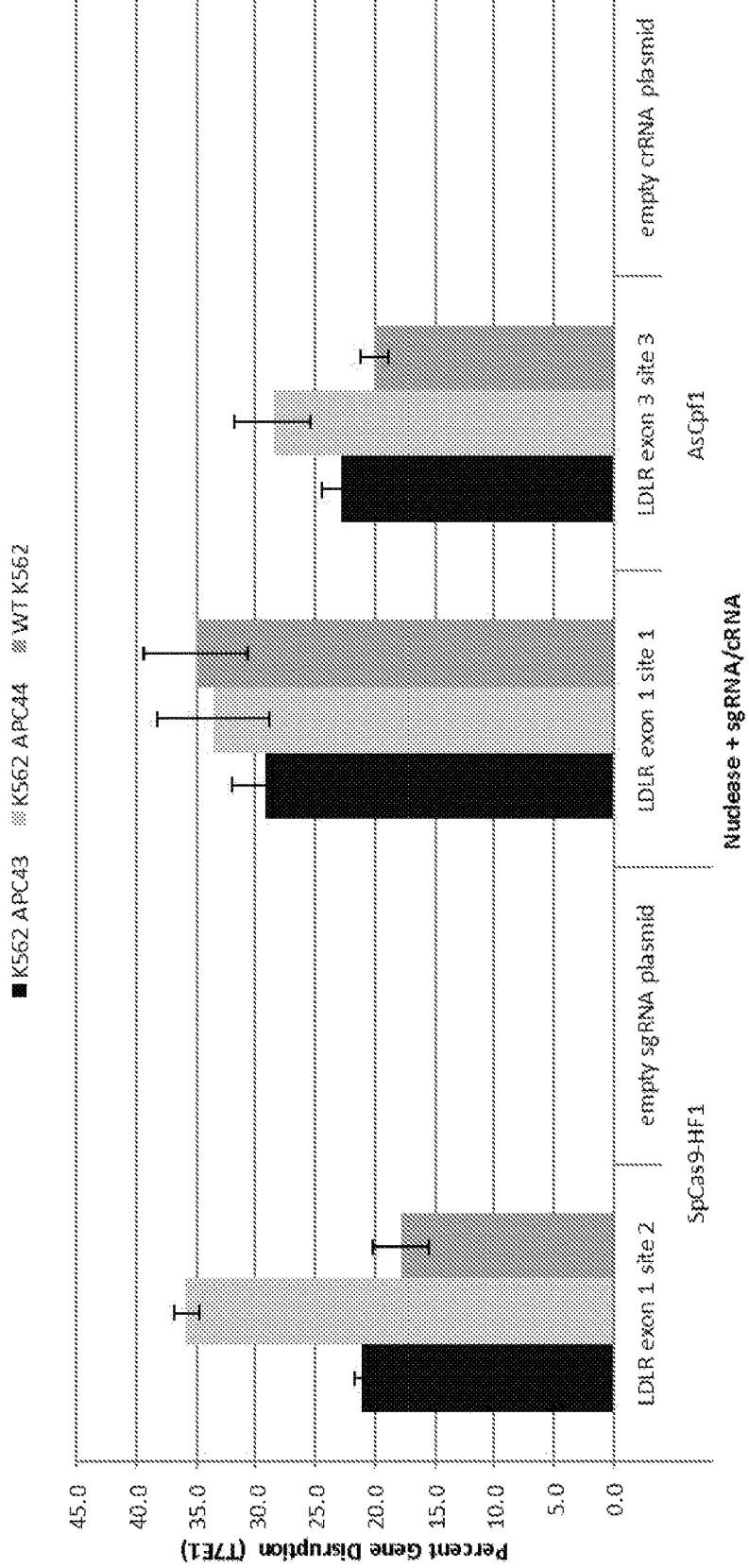
FIG. 11 depicts LDLR KO aAPC (with OKT3 and 9.3 CSRs)—T7E1 results. 5 conditions, in triplicate, are shown.
Figure 12:
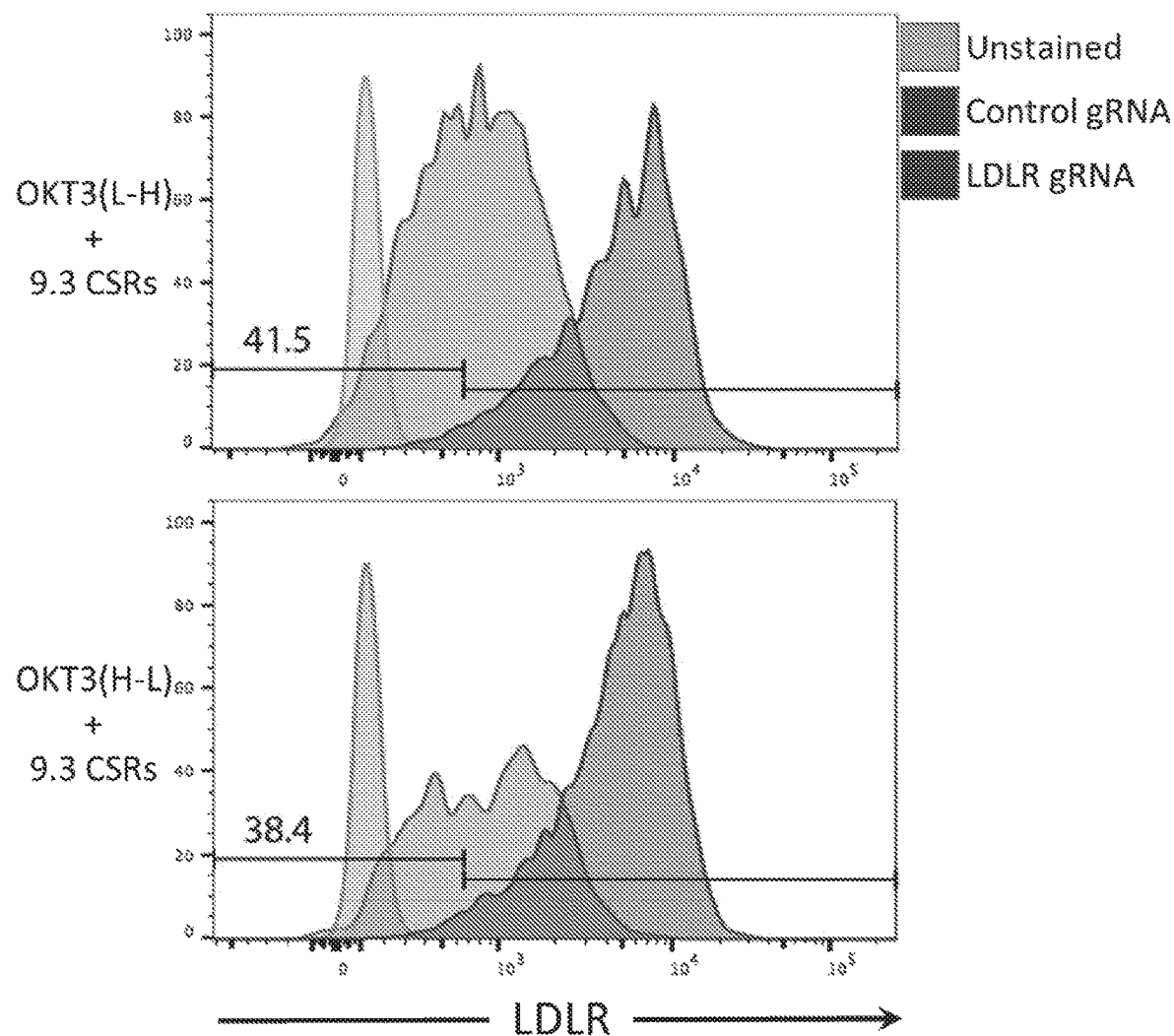
FIG. 12 depicts LDLR KO aAPC flow results.
Figure 13A:
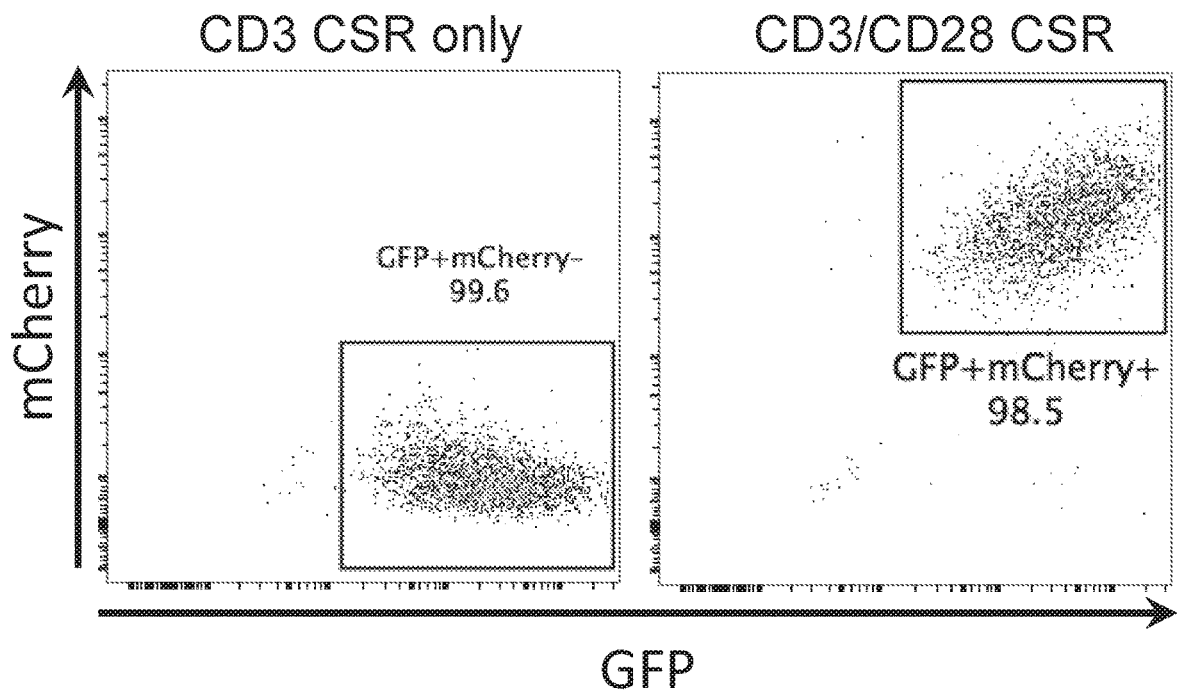
FIG. 13A is a graph showing the results of a flow cytometry experiment validating the expression of CD3 CSR and CD28 CSR on LDLR KO aAPCs, as assessed by mCherry and GFP staining.
Figure 13B:
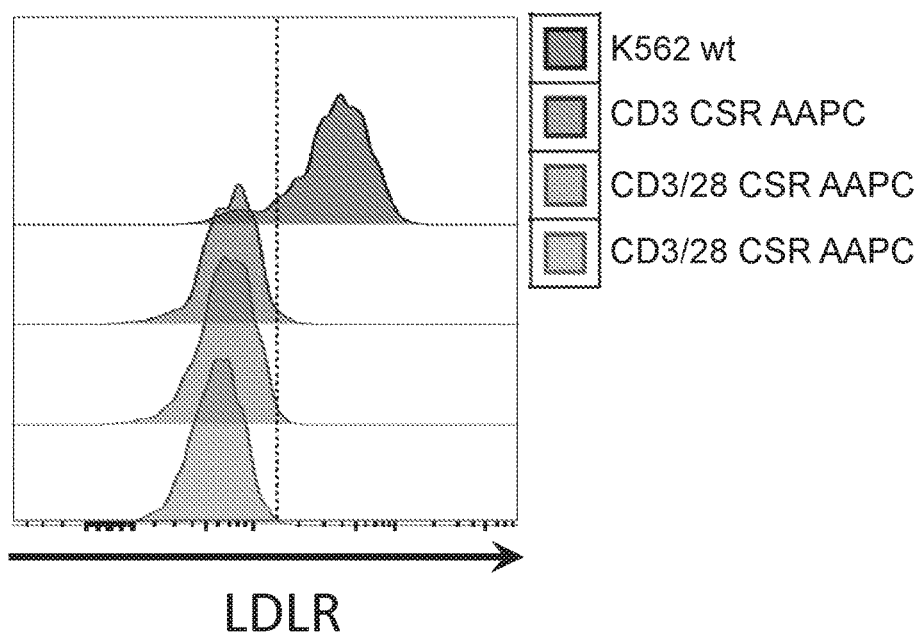
FIG. 13B is a plot showing the results of a flow cytometry experiment validating that LDLR is not expressed on LDLR KO aAPCs, as assessed by an anti-hLDLR-APC antibody. Unmanipulated wild-type K562 cells were used as a positive control for LDLR expression.

FIG. 10 depicts FACS results for 10 selected clones after single-cell sorting and expansion (>20 days). Homogeneous populations were obtained. In some of these clones, the disruption efficiency achieved was very high (eg. sample #9; 86.7%) 2^(15 days)=32,000 cells CRISPR targeting the LDLR gene was repeated for aAPCs exressing CD3+CD28 CSRs. High levels of gene disruption were achieved using the nuclease-guide RNA combinations from the previous assay (FIG. 11). Results of FACS analysis with anti-human LDLR-PE antibody are depicted in FIG. 12 for the nuclease+gRNA combinationof AsCpf1+LDLR Exon3, Site 3 gRNA. The LDLR KO aAPCs were confirmed by flow cytometry to express CD3 and CD8 CSRs (FIG. 13A) but not LDLR (FIG. 13B).

Figure 15A:
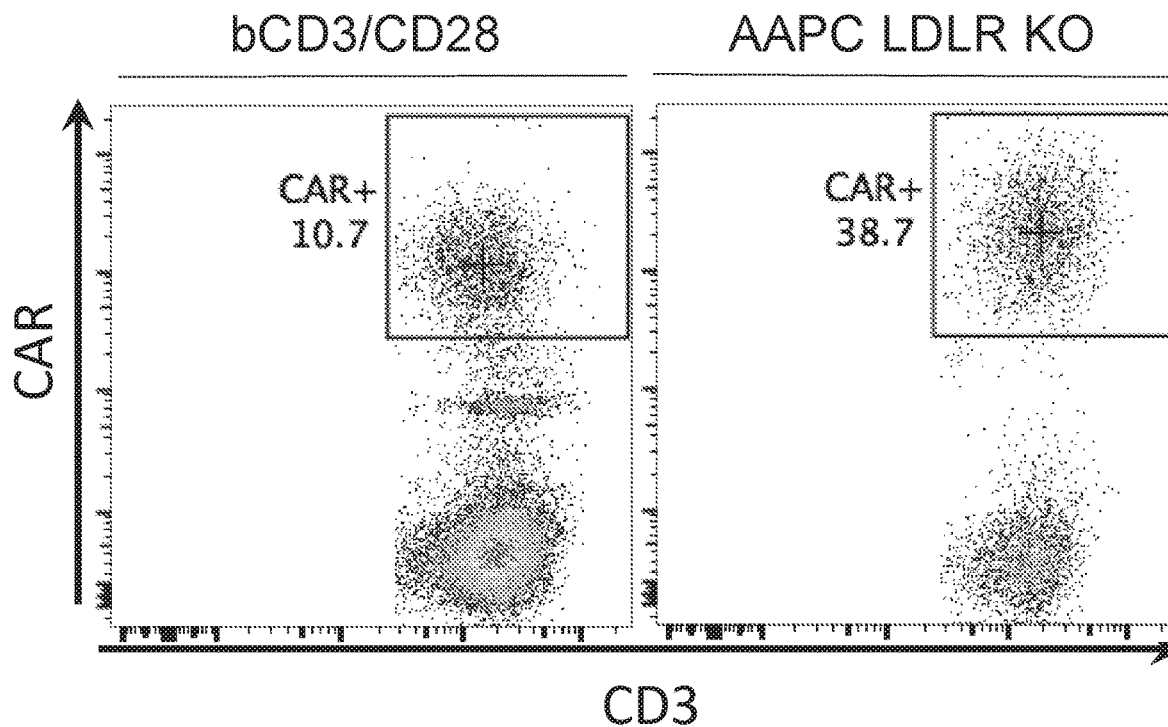
FIGS. 15A and 15B are graphs showing that significantly higher transduction efficiency is achieved using aAPCs compared to bCD3/CD28. Purified T cells from four normal donors were stimulated with either LDLR KO aAPCs (1:1) or bCD3/CD28 (3:1) and analyzed by FACS at day 5 post-stimulation (DAPI, CD3-APC, GFP, mCherry). CAR was detected by mCherry. *** indicates a p-value=0.0008.
Figure 15B:
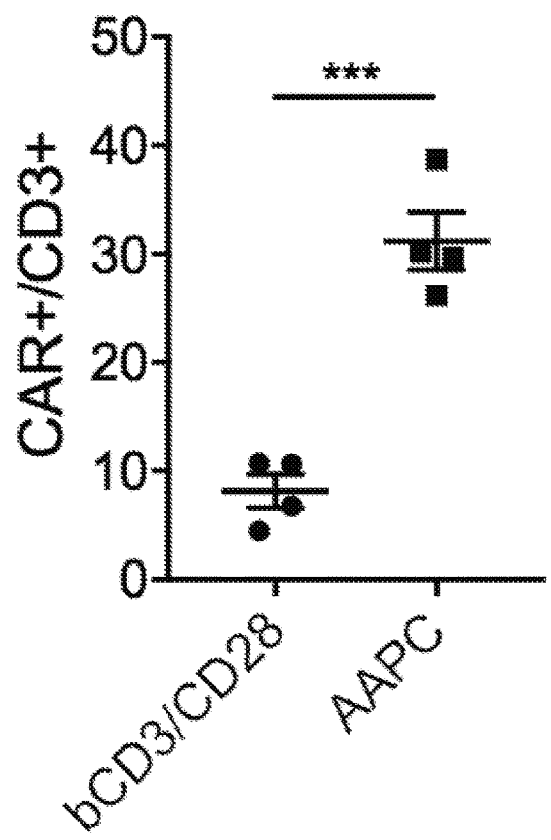
Figure 16:
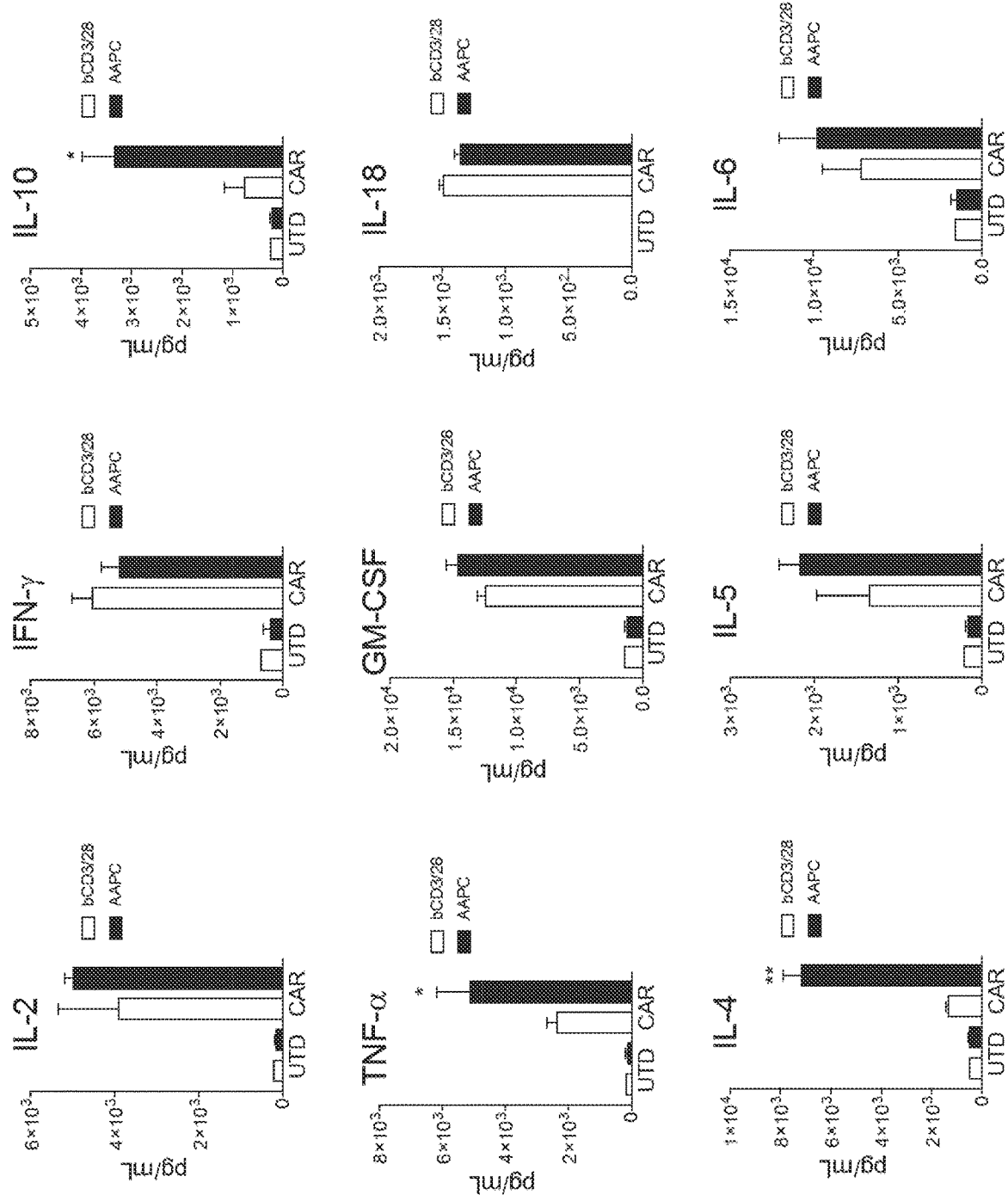
FIG. 16 is a series of graphs showing that CAR T cells expanded with aAPCs have similar cytokine profiles to CAR T cells expanded with bCD3/CD28, except for IL-10, IL-4, and TNF-α. CAR T cells (mut1+3) from a normal donor were stimulated with K562-BCMA for LUMINEX® assay (24 hours).
Figure 17:
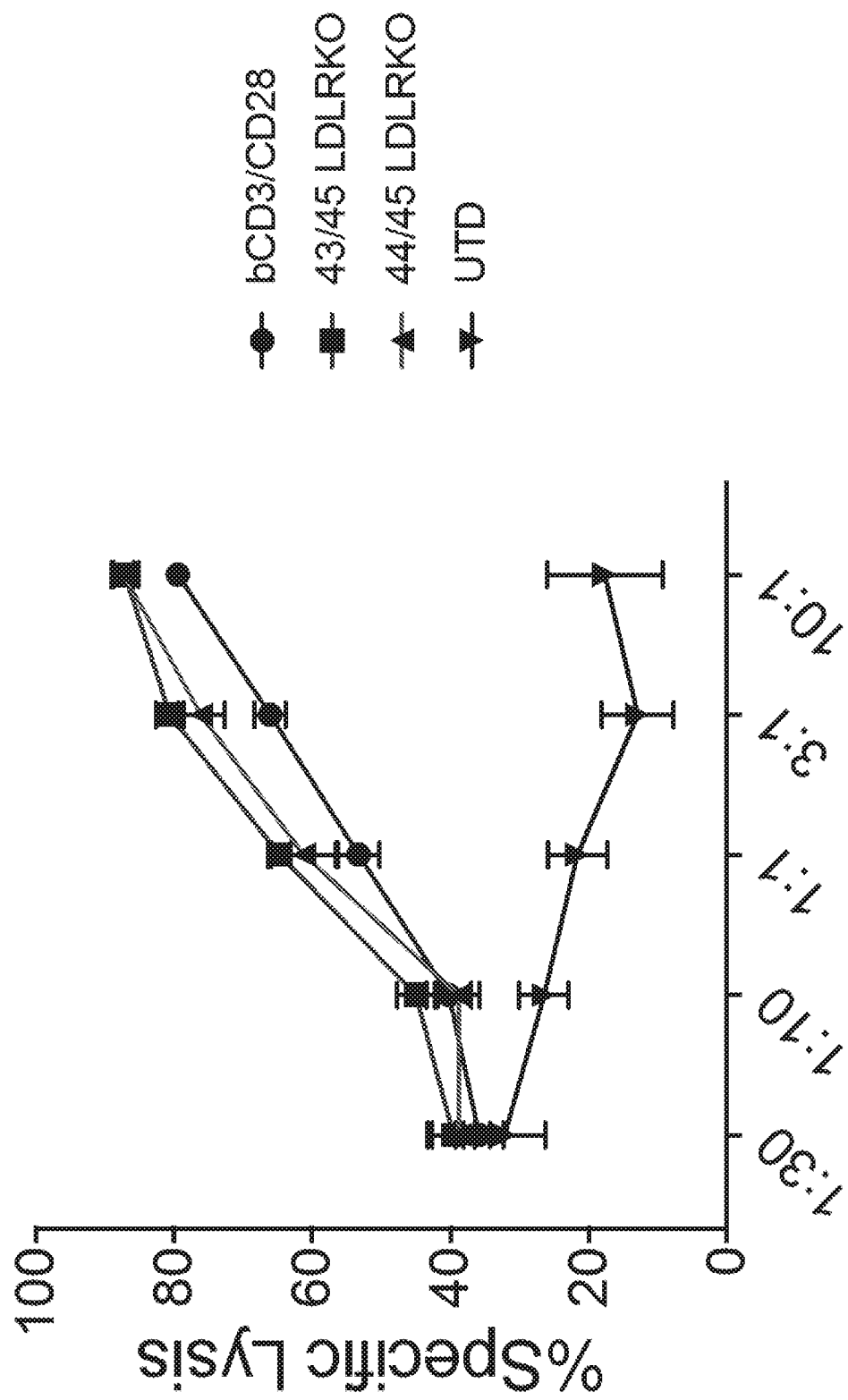
FIG. 17 is a graph showing that CAR T cells expanded with aAPCs have similar tumor killing capacity in vitro as compared to CAR T cells expanded with bCD3/CD28. CAR T cells from three normal donors were stimulated with U266-CBG luc (target: U266 multiple myeloma cells) and analyzed for specific lysis in a killing assay after 16 hours.
Figure 18:
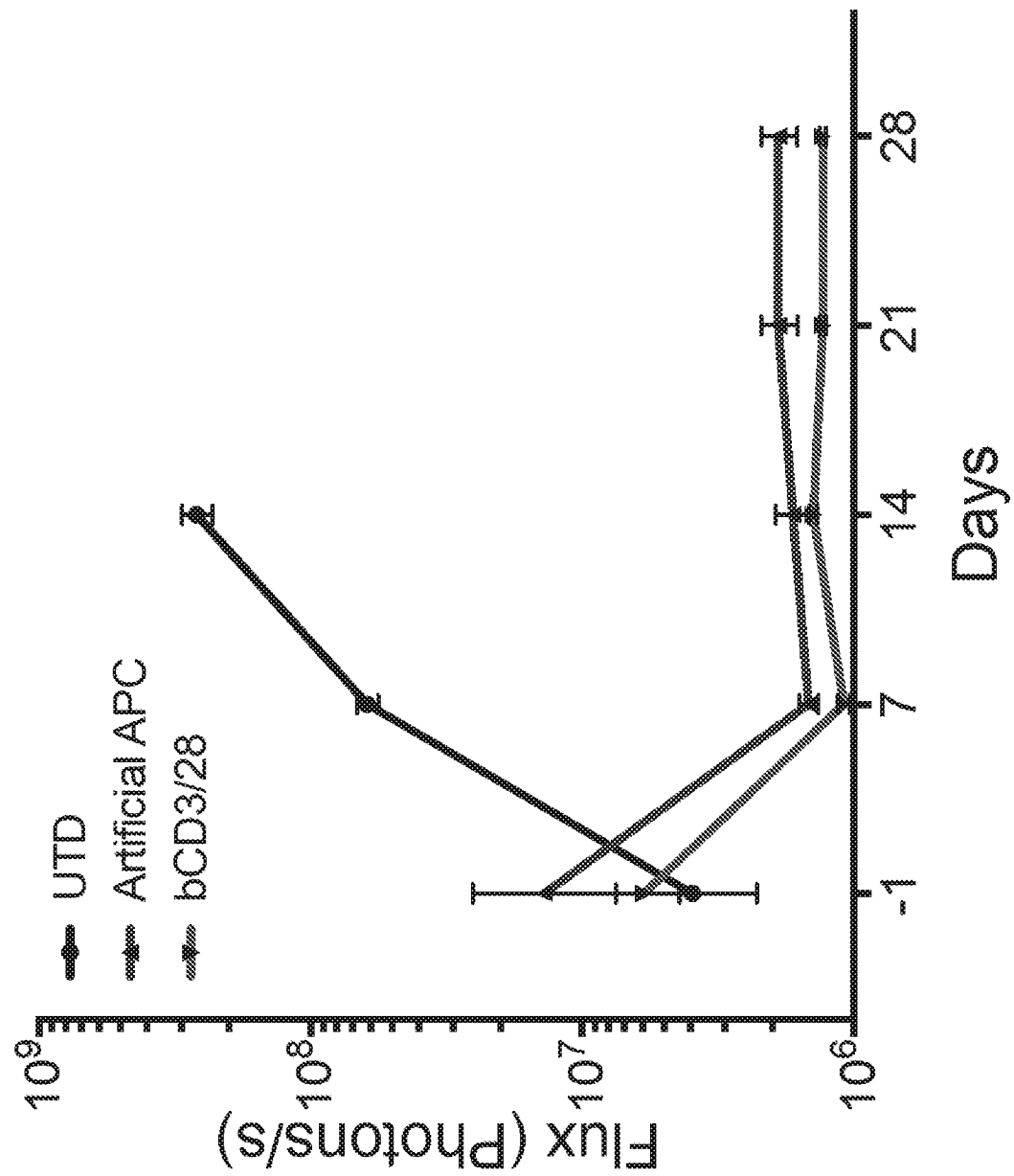
FIG. 18 is a graph showing that CAR T cells expanded with aAPCs have similar tumor killing capacity in vivo as compared to CAR T cells expanded with bCD3/CD28. Mice (n=5) were implanted with $10^6$ U266 multiple myeloma cells at day −7, administered with CAR T cells expanded with aAPCs or bCD3/CD28 at day 0, and assessed by in vivo imaging of produced proton flux at various time points over the course of 28 days post-CAR T cell inoculation. UTD: untreated.

Both LDLR+ and LDLR KO aAPCs were transduced with a GFP-encoding lentivirus. Transduction efficiency (measured by % GFP cells) is significantly reduced in LDLR KO aAPCs (FIGS. 14A and 14B). When purified T cells from normal donors were stimulated with either anti-CD3 and anti-CD28 antibody-conjugated beads (bCD3/CD28, 3:1) or LDLR KO aAPCs (1:1) and analyzed by FACS five days post-stimulation, a higher transduction efficiency was observed using the LDLR KO aAPCs as compared to the using bCD3/CD28 (FIGS. 15A and 15B). However, CAR T cells expanded with the aAPCs share similar cytokine profiles compared to CAR T cells expanded with bCD3/CD28 (FIG. 16). Additionally, CAR T cells expanded with the aAPCs exhibit similar tumor killing capacity compared to CAR T cells expanded with bCD3/CD28, both in vitro (FIG. 17) and in vivo (FIG. 18).

Example 2 aAPC can Induce Human T-Cell Proliferation

Figure 3:
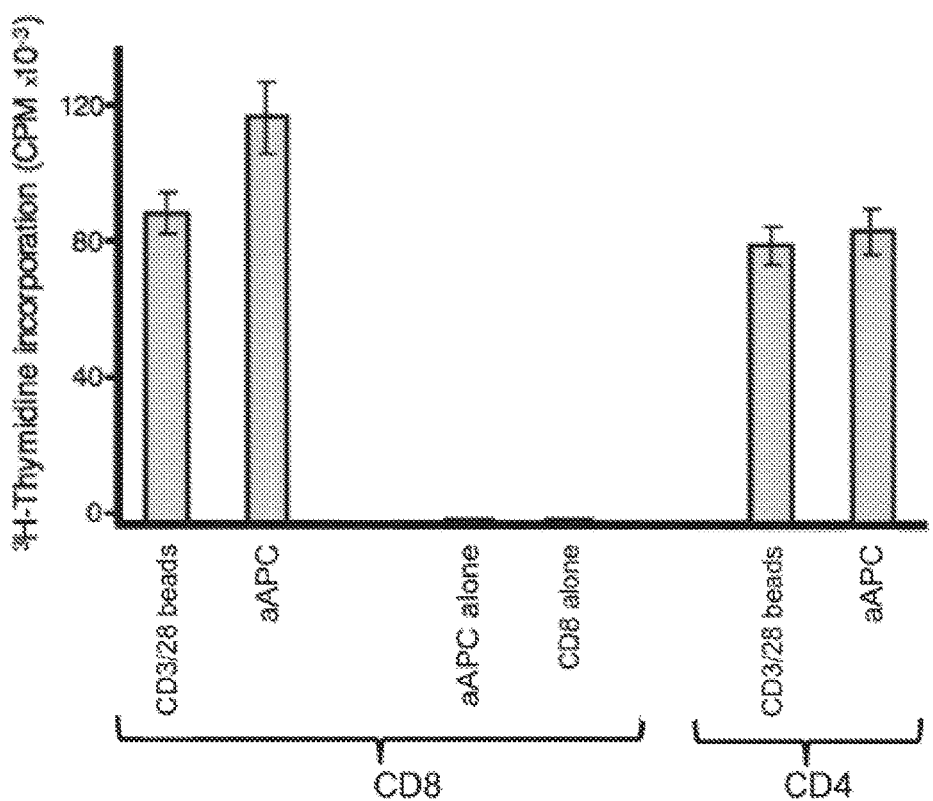
FIG. 3 depicts a graph of proliferation of polyclonal CD8+ and CD4+ T cells stimulated with either CD3/CD28 microspheres (beads) or with artificial APC (aAPC) loaded with anti-CD3 and anti-CD28 monoclonal antibodies as measured by [$^3$H] thymidine incorporation between days 3 and 4 of culture in the absence of cytokines. At 72 h, the cells were pulsed with [$^3$H] thymidine and incubated for an additional 18 h before harvesting. Counts per minute values are shown as mean±SEM from triplicate cultures.

The capacity of cell-based aAPC to stimulate human T cells and induce their proliferation has been tested as follows. Primary T cells were isolated from peripheral blood of a normal donor and a chronic lymphocytic leukemia patient. Both T cell preparations were cultured for 9 days in the presence of CD3/CD28 microspheres (current method) or with aAPC displaying anti-CD3 and anti-CD28 antibody constructs. T-cells co-cultured with aAPC expanded in a similar or even better fashion than the ones stimulated with the microspheres (FIG. 2). Similar results were obtained by measuring [$^3$H]thymidine incorporation in both polyclonal CD4+ and CD8+ T cells purified from multiple donors activated either by aAPC or microspheres (FIG. 3).

Example 3

CSR Construct Sequences pMGH43-anti-hOKT3-L/H-GFP (SEQ ID NO: 1) comprising CD8leader (amino acids 1-21 (SEQ ID NO: 2)); VL (amino acids 22-127 (SEQ ID NO: 3)); linker (amino acids 128-147 (SEQ ID NO: 4)), VH (amino acids 148-266 (SEQ ID NO: 5)), CD8hingeTM (amino acids 267-335 (SEQ ID NO: 6)); AAAAA-CD3Z (amino acids 336-340 (SEQ ID NO: 7)); T2A linker (amino acids 341-364 (SEQ ID NO: 8)); and GFP (amino acids 365-603 (SEQ ID NO: 9)).

```
                                         (SEQ ID NO: 1)
MALPVTALLLPLALLLHAARPDIQMTQSPSSLSASVGDRVTITCSASSSV

SYMNWYQQTPGKAPKRWIYDTSKLASGVPSRFSGSGSGTDYTFTISSLQP

EDIATYYCQQWSSNPFTFGQGTKLQITGGGGSGGGGSGGGGSGGGGSQVQ

LVQSGGGVVQPGRSLRLSCKASGYTFTRYTMHWVRQAPGKGLEWIGYINP

SRGYTNYNQKVKDRFTISRDNSKNTAFLQMDSLRPEDTGVYFCARYYDDH

YCLDYWGQGTPVTVSSTTTPAPRPPTPAPTIASQPLSLRPEACRPAAGGA

VHTRGLDFACDIYIWAPLAGTCGVLLLSLVITLYCRVKFSSGGGGEGRGS

LLTCGDVEENPGPRMVSKGEELFTGVVPILVELDGDVNGHKFSVSGEGEG

DATYGKLTLKFICTTGKLPVPWPTLVTTLTYGVQCFSRYPDHMKQHDFFK

SAMPEGYVQERTIFFKDDGNYKTRAEVKFEGDTLVNRIELKGIDFKEDGN

ILGHKLEYNYNSHNVYIMADKQKNGIKVNFKIRHNIEDGSVQLADHYQQN

TPIGDGPVLLPDNHYLSTQSALSKDPNEKRDHMVLLEFVTAAGITLGMDE

LYK
```

CD8 leader (SEQ ID NO: 2 (amino acids 1-21 of SEQ ID NO: 1))

```
                                         (SEQ ID NO: 2)
MALPVTALLLPLALLLHAARP
```

VL sequence (SEQ ID NO: 3 (amino acids 22-127 of SEQ ID NO: 1))

```
                                         (SEQ ID NO: 3)
DIQMTQSPSSLSASVGDRVTITCSASSSVSYMNWYQQTPGKAPKRWIYDT

SKLASGVPSRFSGSGSGTDYTFTISSLQPEDIATYYCQQWSSNPFTFGQG

TKLQIT
```

Linker sequence (SEQ ID NO: 4 (amino acids 128-147 of SEQ ID NO: 1))

```
                                         (SEQ ID NO: 4)
                GGGGSGGGGSGGGGSGGGGS
```

VH sequence (SEQ ID NO: 5 (amino acids 148-266 of SEQ ID NO: 1))

```
                                         (SEQ ID NO: 5)
QVQLVQSGGGVVQPGRSLRLSCKASGYTFTRYTMHWVRQAPGKGLEWIGY

INPSRGYTNYNQKVKDRFTISRDNSKNTAFLQMDSLRPEDTGVYFCARYY

DDHYCLDYWGQGTPVTVSS
```

CD8 hingeTM (SEQ ID NO: 6 (amino acids 267-335 of SEQ ID NO: 1))

```
                                         (SEQ ID NO: 6)
TTTPAPRPPTPAPTIASQPLSLRPEACRPAAGGAVHTRGLDFACDIYIWA

PLAGTCGVLLLSLVITLYC
```

AAAAA-CD3Z (SEQ ID NO: 7 (amino acids 336-340 of SEQ ID NO: 1))

```
                                         (SEQ ID NO: 7)
                      RVKFS
```

T2A linker (SEQ ID NO: 8 (amino acids 341-364 of SEQ ID NO: 1))

```
                                         (SEQ ID NO: 8)
             SGGGGEGRGSLLTCGDVEENPGPR
```

GFP (SEQ ID NO: 9 (amino acids 365-603 of SEQ ID NO: 1))

```
                                         (SEQ ID NO: 9)
MVSKGEELFTGVVPILVELDGDVNGHKFSVSGEGEGDATYGKLTLKFICT

TGKLPVPWPTLVTTLTYGVQCFSRYPDHMKQHDFFKSAMPEGYVQERTIF

FKDDGNYKTRAEVKFEGDTLVNRIELKGIDFKEDGNILGHKLEYNYNSHN

VYIMADKQKNGIKVNFKIRHNIEDGSVQLADHYQQNTPIGDGPVLLPDNH

YLSTQSALSKDPNEKRDHMVLLEFVTAAGITLGMDELYK
``` pMGH44/anti-hOKT3_H/L-GFP (SEQ ID NO: 10) comprising CD8leader (amino acids 1-21 (SEQ ID NO: 11)); VH (amino acids 22-140 (SEQ ID NO: 12)); linker (amino acids 141-160 (SEQ ID NO: 13)); VL (amino acids 161-266 (SEQ ID NO: 14)); CD8hingeTM (amino acids 267-335 (SEQ ID NO: 15)); AAAAA-CD3Z (amino acids 336-340 (SEQ ID NO: 16)); T2A (amino acids 341-364 (SEQ ID NO: 17)); and GFP (amino acids 365-603 (SEQ ID NO: 18)).

```
                                        (SEQ ID NO: 10)
MALPVTALLLPLALLLHAARPQVQLVQSGGGVVQPGRSLRLSCKASGYTF

TRYTMHWVRQAPGKGLEWIGYINPSRGYTNYNQKVKDRFTISRDNSKNTA

FLQMDSLRPEDTGVYFCARYYDDHYCLDYWGQGTPVTVSSGGGGSGGGGS

GGGGSGGGGSDIQMTQSPSSLSASVGDRVTITCSASSSVSYMNWYQQTPG

KAPKRWIYDTSKLASGVPSRFSGSGSGTDYTFTISSLQPEDIATYYCQQW

SSNPFTFGQGTKLQITTTTPAPRPPTPAPTIASQPLSLRPEACRPAAGGA

VHTRGLDFACDIYIWAPLAGTCGVLLLSLVITLYCRVKFSSGGGGEGRGS

LLTCGDVEENPGPRMVSKGEELFTGVVPILVELDGDVNGHKFSVSGEGEG

DATYGKLTLKFICTTGKLPVPWPTLVTTLTYGVQCFSRYPDHMKQHDFFK

SAMPEGYVQERTIFFKDDGNYKTRAEVKFEGDTLVNRIELKGIDFKEDGN

ILGHKLEYNYNSHNVYIMADKQKNGIKVNFKIRHNIEDGSVQLADHYQQN

TPIGDGPVLLPDNHYLSTQSALSKDPNEKRDHMVLLEFVTAAGITLGMDE

LYK
```

CD8 leader (SEQ ID NO: 11 (amino acids 1-21 of SEQ ID NO: 10))

```
                                        (SEQ ID NO: 11)
                 MALPVTALLLPLALLLHAARP
```

VH sequence (SEQ ID NO: 12 (amino acids 22-140 of SEQ ID NO: 10))

```
                                        (SEQ ID NO: 12)
QVQLVQSGGGVVQPGRSLRLSCKASGYTFTRYTMHWVRQAPGKGLEWIGY

INPSRGYTNYNQKVKDRFTISRDNSKNTAFLQMDSLRPEDTGVYFCARYY

DDHYCLDYWGQGTPVTVSS
```

Linker (SEQ ID NO: 13 (amino acids 141-160 of SEQ ID NO: 10))

```
                                        (SEQ ID NO: 13)
                GGGGSGGGGSGGGGSGGGGS
```

VL sequence (SEQ ID NO: 14 (amino acids 161-266 of SEQ ID NO: 10))

```
                                        (SEQ ID NO: 14)
DIQMTQSPSSLSASVGDRVTITCSASSSVSYMNWYQQTPGKAPKRWIYDT

SKLASGVPSRFSGSGSGTDYTFTISSLQPEDIATYYCQQWSSNPFTFGQG

TKLQIT
```

CD8 hingeTM (SEQ ID NO: 15 (amino acids 267-335 of SEQ ID NO: 10))

```
                                        (SEQ ID NO: 15)
TTTPAPRPPTPAPTIASQPLSLRPEACRPAAGGAVHTRGLDFACDIYIWA

PLAGTCGVLLLSLVITLYC
```

AAAAA-CD3Z (SEQ ID NO: 16 (amino acids 336-340 of SEQ ID NO: 10))

```
                                            (SEQ ID NO: 16)
RVKFS
```

T2A linker (SEQ ID NO: 17 (amino acids 341-364 of SEQ ID NO: 10))

```
                                            (SEQ ID NO: 17)
SGGGGEGRGSLLTCGDVEENPGPR
```

GFP (SEQ ID NO: 18 (amino acids 365-603 of SEQ ID NO: 10))

```
                                            (SEQ ID NO: 18)
MVSKGEELFTGVVPILVELDGDVNGHKFSVSGEGEGDATYGKLTLKFICT

TGKLPVPWPTLVTTLTYGVQCFSRYPDHMKQHDFFKSAMPEGYVQERTIF

FKDDGNYKTRAEVKFEGDTLVNRIELKGIDFKEDGNILGHKLEYNYNSHN

VYIMADKQKNGIKVNFKIRHNIEDGSVQLADHYQQNTPIGDGPVLLPDNH

YLSTQSALSKDPNEKRDHMVLLEFVTAAGITLGMDELYK
``` pMGH45/anti-9.3-CD28-T2A-mCHERRY (SEQ ID NO: 19) comprising CD8leader (amino acids 1-20 (SEQ ID NO: 20)); scFv-CD28-VL (amino acids 21-133 (SEQ ID NO: 21)); linker (amino acids 134-153 (SEQ ID NO: 22)); scFv-CD28-VH (amino acids 154-275 (SEQ ID NO: 23)); CD28-EC-TM-ICD (amino acids 276-358 (SEQ ID NO: 24)); T2A (amino acids 359-382 (SEQ ID NO: 25)); and mCHERRY (amino acids 383-618 (SEQ ID NO: 26)).

```
                                            (SEQ ID NO: 19)
MESDTLLLWVLLLWVPGSTGDIVLTQSPASLAVSLGQRATISCRASESVE

YYVTSLMQWYQQKPGQPPKLLIFAASNVESGVPARFSGSGSGTNFSLNIH

PVDEDDVAMYFCQQSRKVPYTFGGGTKLEIKRAGGGGSGGGGSGGGGSGG

GGSLAQVQLKESGPGLVTPSQSLSITCTVSGFSLSDYGVHWVRQSPGQGL

ECLGVIWAGGGTNYNSALMSRKSISKDNSKGQVFLKMKSLQADDTAVYYC

ARDKGYSYYYSMDYWGQGTSVTVSSKHLCPSPLFPGPSKPFWVLVVVGGV

LACYSLLVTVAFIIFWVRSKRSRLLHSDYMNMTPRRPGPTRKHYQPYAPP

RDFAAYRSSGGGGEGRGSLLTCGDVEENPGPRMVSKGEEDNMAIIKEFMR

FKVHMEGSVNGHEFEIEGEGEGRPYEGTQTAKLKVTKGGPLPFAWDILSP

QFMYGSKAYVKHPADIPDYLKLSFPEGFKWERVMNFEDGGVVTVTQDSSL

QDGEFIYKVKLRGTNFPSDGPVMQKKTMGWEASSERMYPEDGALKGEIKQ

RLKLKDGGHYDAEVKTTYKAKKPVQLPGAYNVNIKLDITSHNEDYTIVEQ

YERAEGRHSTGGMDELYK
```

CD8 leader (SEQ ID NO: 20 (amino acids 1-20 of SEQ ID NO: 19))

```
                                            (SEQ ID NO: 20)
MALPVTALLLPLALLLHAARP
``` scFv-CD28-VL (SEQ ID NO: 21 (amino acids 21-133 of SEQ ID NO: 19))

```
                                            (SEQ ID NO: 21)
DIVLTQSPASLAVSLGQRATISCRASESVEYYVTSLMQWYQQKPGQPPKL

LIFAASNVESGVPARFSGSGSGTNFSLNIHPVDEDDVAMYFCQQSRKVPY

TFGGGTKLEIKRA
```

Linker (SEQ ID NO: 22 (amino acids 134-153 of SEQ ID NO: 19))

```
                                            (SEQ ID NO: 22)
GGGGSGGGGSGGGGSGGGGS
``` scFv-CD28-VH (SEQ ID NO: 23 (amino acids 154-275 of SEQ ID NO: 19))

```
                                            (SEQ ID NO: 23)
LAQVQLKESGPGLVTPSQSLSITCTVSGFSLSDYGVHWVRQSPGQGLECL

GVIWAGGGTNYNSALMSRKSISKDNSKGQVFLKMKSLQADDTAVYYCARD

KGYSYYYSMDYWGQGTSVTVSS
```

CD28-EC-TM-ICD (SEQ ID NO: 24 (amino acids 276-358 of SEQ ID NO: 19))

```
                                            (SEQ D NO: 24)
KHLCPSPLFPGPSKPFWVLVVVGGVLACYSLLVTVAFIIFWVRSKRSR

LLHSDYMNMTPRRPGPTRKHYQPYAPPRDFAAYRS
```

T2A linker (SEQ ID NO: 25 (amino acids 359-382 of SEQ ID NO: 19))

```
                                            (SEQ ID NO: 25)
SGGGGEGRGSLLTCGDVEENPGPR
``` mCherry (SEQ ID NO: 26 (amino acids 383-618 of SEQ ID NO: 19))

```
                                            (SEQ ID NO: 26)
MVSKGEEDNMAIIKEFMRFKVHMEGSVNGHEFEIEGEGEGRPYEGTQT

AKLKVTKGGPLPFAWDILSPQFMYGSKAYVKHPADIPDYLKLSFPEGF

KWERVMNFEDGGVVTVTQDSSLQDGEFIYKVKLRGTNFPSDGPVMQKK

TMGWEASSERMYPEDGALKGEIKQRLKLKDGGHYDAEVKTTYKAKKPV

QLPGAYNVNIKLDITSHNEDYTIVEQYERAEGRHSTGGMDELYK
```

Example 4

Antibody Sequences

OKT3 L/H (SEQ ID NO: 27) comprising VL (amino acids 1-106 (SEQ ID NO: 28)); linker (amino acids 107-126 (SEQ ID NO: 29)); and VH (amino acids 127-245 (SEQ ID NO: 30)).

```
                                            (SEQ ID NO: 27)
DIQMTQSPSSLSASVGDRVTITCSASSSVSYMNWYQQTPGKAPKRWIY

DTSKLASGVPSRFSGSGSGTDYTFTISSLQPEDIATYYCQQWSSNPFT
```

-continued

FGQGTKLQITGGGGSGGGGSGGGGSGGGGSQVQLVQSGGGVVQPGRSL

RLSCKASGYTFTRYTMHWVRQAPGKGLEWIGYINPSRGYTNYNQKVKD

RFTISRDNSKNTAFLQMDSLRPEDTGVYFCARYYDDHYCLDYWGQGTP

VTVSS

VL (SEQ ID NO: 28 (amino acids 1-106 of SEQ ID NO: 27))

(SEQ ID NO: 28)
DIQMTQSPSSLSASVGDRVTITCSASSSVSYMNWYQQTPGKAPKRWIY

DTSKLASGVPSRFSGSGSGTDYTFTISSLQPEDIATYYCQQWSSNPFT

FGQGTKLQIT

Linker (SEQ ID NO: 29 (amino acids 107-126 of SEQ ID NO: 27))

(SEQ ID NO: 29)
GGGGSGGGGSGGGGSGGGGS

VH (SEQ ID NO: 30 (amino acids 127-245 of SEQ ID NO: 27))

(SEQ ID NO: 30)
QVQLVQSGGGVVQPGRSLRLSCKASGYTFTRYTMHWVRQAPGKGLEWI

GYINPSRGYTNYNQKVKDRFTISRDNSKNTAFLQMDSLRPEDTGVYFC

ARYYDDHYCLDYWGQGTPVTVSS

OKT3 H/L (SEQ ID NO: 31) comprising VH (amino acids 1-119 (SEQ ID NO: 32)); linker (amino acids 120-139 (SEQ ID NO: 33)); and VL (amino acids 140-245 (SEQ ID NO: 34)).

(SEQ ID NO: 31)
QVQLVQSGGGVVQPGRSLRLSCKASGYTFTRYTMHWVRQAPGKGLEWI

GYINPSRGYTNYNQKVKDRFTISRDNSKNTAFLQMDSLRPEDTGVYFC

ARYYDDHYCLDYWGQGTPVTVSSGGGGSGGGGSGGGGSGGGGSDIQMT

QSPSSLSASVGDRVTITCSASSSVSYMNWYQQTPGKAPKRWIYDTSKL

ASGVPSRFSGSGSGTDYTFTISSLQPEDIATYYCQQWSSNPFTFGQGT

KLQIT

VH (SEQ ID NO: 32 (amino acids 1-119 of SEQ ID NO: 31))

(SEQ ID NO: 32)
QVQLVQSGGGVVQPGRSLRLSCKASGYTFTRYTMHWVRQAPGKGLEWI

GYINPSRGYTNYNQKVKDRFTISRDNSKNTAFLQMDSLRPEDTGVYFC

ARYYDDHYCLDYWGQGTPVTVSS

Linker (SEQ ID NO: 33 (amino acids 120-139 of SEQ ID NO: 31))

(SEQ ID NO: 33)
GGGGSGGGGSGGGGSGGGGS

VL (SEQ ID NO: 34 (amino acids 140-245 of SEQ ID NO: 31))

(SEQ ID NO: 34)
DIQMTQSPSSLSASVGDRVTITCSASSSVSYMNWYQQTPGKAPKRWIY

DTSKLASGVPSRFSGSGSGTDYTFTISSLQPEDIATYYCQQWSSNPFT

FGQGTKLQIT anti-CD28 (9.3 L/H) (SEQ ID NO: 35) comprising VL (amino acids 1-113 (SEQ ID NO: 36)); linker (amino acids 114-133 (SEQ ID NO: 37)); and VH (amino acids 134-255 (SEQ ID NO: 38)).

(SEQ ID NO: 35)
DIVLTQSPASLAVSLGQRATISCRASESVEYYVTSLMQWYQQKPGQPP

KLLIFAASNVESGVPARFSGSGSGTNFSLNIHPVDEDDVAMYFCQQSR

KVPYTFGGGTKLEIKRAGGGGSGGGGSGGGGSGGGGSLAQVQLKESGP

GLVTPSQSLSITCTVSGFSLSDYGVHWVRQSPGQGLECLGVIWAGGGT

NYNSALMSRKSISKDNSKGQVFLKMKSLQADDTAVYYCARDKGYSYYY

SMDYWGQGTSVTVSS

VL (SEQ ID NO: 36 (amino acids 1-113 (SEQ ID NO: 35))

(SEQ ID NO: 36)
DIVLTQSPASLAVSLGQRATISCRASESVEYYVTSLMQWYQQKPGQPP

KLLIFAASNVESGVPARESGSGSGTNFSLNIHPVDEDDVAMYFCQQSR

KVPYTFGGGTKLEIKRA

Linker (SEQ ID NO: 37 (amino acids 114-133 (SEQ ID NO: 35))

(SEQ ID NO: 37)
GGGGSGGGGSGGGGSGGGGS

VH (SEQ ID NO: 38 (amino acids 134-255 (SEQ ID NO: 35))

(SEQ ID NO: 38)
LAQVQLKESGPGLVTPSQSLSITCTVSGFSLSDYGVHWVRQSPGQGLE

CLGVIWAGGGTNYNSALMSRKSISKDNSKGQVFLKMKSLQADDTAVYY

CARDKGYSYYYSMDYWGQGTSVTVSS

What is claimed herein is:

1. An artificial antigen presenting cell (aAPC) comprising:
   a first chimeric stimulatory receptor (CSR) comprising an antibody or antigen binding domain that specifically binds to CD3binds; and
   a second CSR comprising (i) an antibody or antigen binding domain that specifically binds to CD28, 4-1BB, CD134, CD2 or ICOS, or (ii) a natural ligand that binds to CD28,
   wherein the aAPC lacks an expressible low-density lipoprotein receptor (LDLR) gene.

2. The aAPC of claim 1 wherein:
   the first CSR specifically binds to CD3; and
   the second CSR specifically binds to CD28.

3. The aAPC of claim 1, wherein the aAPC comprises a deletion in the native LDLR-encoding nucleic acid sequence.

4. The aAPC of claim 1, wherein the aAPC is viable but non-dividing.

5. The aAPC of claim 1, wherein the first and second CSRs are expressed on the cell surface of the aAPC.

6. The aAPC of claim 1, wherein the first and second CSRs are constitutively expressed.

7. The aAPC of claim 1, wherein the first and second CSRs are encoded by a first recombinant nucleic acid sequence and a second recombinant nucleic acid sequence, respectively.

8. The aAPC of claim 1, wherein the aAPC is a human cell.

9. The aAPC of claim 1, wherein the aAPC is engineered from an erythromyeloid cell.

10. The aAPC of claim 1, wherein the first and second CSRs bind specifically with human CD3 and CD28, respectively.

11. A method of expanding or activating a T cell, the method comprising contacting the aAPC of claim 1 with a T cell.

12. The method of claim 11, wherein the contacting step occurs in vitro.

13. The method of claim 11, wherein the contacting step occurs in suspension.

14. A composition comprising the aAPC of claim 1 and a T cell.

15. The composition of claim 14, wherein the T cell is a CAR T cell.

16. An artificial antigen presenting cell (aAPC) comprising:
- a first chimeric stimulatory receptor (CSR) comprising the amino acid sequence of SEQ ID NO: 1 or SEQ ID NO: 10; and
- a second CSR comprising the amino acid sequence of SEQ ID NO: 19.

17. The aAPC of claim 1, wherein the aAPC has been engineered to lack an expressible low-density lipoprotein receptor (LDLR) gene.

* * * * *

SEQUENCE LISTING

<160> NUMBER OF SEQ ID NOS: 38

<210> SEQ ID NO 1
<211> LENGTH: 603

```
<212> TYPE: PRT
<213> ORGANISM: Artificial Sequence
<220> FEATURE:
<223> OTHER INFORMATION: Synthetic Construct

<400> SEQUENCE: 1

Met Ala Leu Pro Val Thr Ala Leu Leu Pro Leu Ala Leu Leu
1               5                   10                  15

His Ala Ala Arg Pro Asp Ile Gln Met Thr Gln Ser Pro Ser Ser Leu
                20                  25                  30

Ser Ala Ser Val Gly Asp Arg Val Thr Ile Thr Cys Ser Ala Ser Ser
            35                  40                  45

Ser Val Ser Tyr Met Asn Trp Tyr Gln Gln Thr Pro Gly Lys Ala Pro
50                  55                  60

Lys Arg Trp Ile Tyr Asp Thr Ser Lys Leu Ala Ser Gly Val Pro Ser
65                  70                  75                  80

Arg Phe Ser Gly Ser Gly Ser Gly Thr Asp Tyr Thr Phe Thr Ile Ser
                85                  90                  95

Ser Leu Gln Pro Glu Asp Ile Ala Thr Tyr Tyr Cys Gln Gln Trp Ser
            100                 105                 110

Ser Asn Pro Phe Thr Phe Gly Gln Gly Thr Lys Leu Gln Ile Thr Gly
        115                 120                 125

Gly Gly Gly Ser Gly Gly Gly Gly Ser Gly Gly Gly Gly Ser Gly Gly
130                 135                 140

Gly Gly Ser Gln Val Gln Leu Val Gln Ser Gly Gly Gly Val Val Gln
145                 150                 155                 160

Pro Gly Arg Ser Leu Arg Leu Ser Cys Lys Ala Ser Gly Tyr Thr Phe
                165                 170                 175

Thr Arg Tyr Thr Met His Trp Val Arg Gln Ala Pro Gly Lys Gly Leu
            180                 185                 190

Glu Trp Ile Gly Tyr Ile Asn Pro Ser Arg Gly Tyr Thr Asn Tyr Asn
        195                 200                 205

Gln Lys Val Lys Asp Arg Phe Thr Ile Ser Arg Asp Asn Ser Lys Asn
210                 215                 220

Thr Ala Phe Leu Gln Met Asp Ser Leu Arg Pro Glu Asp Thr Gly Val
225                 230                 235                 240

Tyr Phe Cys Ala Arg Tyr Tyr Asp Asp His Tyr Cys Leu Asp Tyr Trp
                245                 250                 255

Gly Gln Gly Thr Pro Val Thr Val Ser Ser Thr Thr Thr Pro Ala Pro
            260                 265                 270

Arg Pro Pro Thr Pro Ala Pro Thr Ile Ala Ser Gln Pro Leu Ser Leu
        275                 280                 285

Arg Pro Glu Ala Cys Arg Pro Ala Ala Gly Gly Ala Val His Thr Arg
290                 295                 300

Gly Leu Asp Phe Ala Cys Asp Ile Tyr Ile Trp Ala Pro Leu Ala Gly
305                 310                 315                 320

Thr Cys Gly Val Leu Leu Leu Ser Leu Val Ile Thr Leu Tyr Cys Arg
                325                 330                 335

Val Lys Phe Ser Ser Gly Gly Gly Glu Gly Arg Gly Ser Leu Leu
            340                 345                 350

Thr Cys Gly Asp Val Glu Glu Asn Pro Gly Pro Arg Met Val Ser Lys
        355                 360                 365

Gly Glu Glu Leu Phe Thr Gly Val Val Pro Ile Leu Val Glu Leu Asp
370                 375                 380
```

```
Gly Asp Val Asn Gly His Lys Phe Ser Val Ser Gly Glu Gly Glu Gly
385                 390                 395                 400

Asp Ala Thr Tyr Gly Lys Leu Thr Leu Lys Phe Ile Cys Thr Thr Gly
            405                 410                 415

Lys Leu Pro Val Pro Trp Pro Thr Leu Val Thr Thr Leu Thr Tyr Gly
        420                 425                 430

Val Gln Cys Phe Ser Arg Tyr Pro Asp His Met Lys Gln His Asp Phe
    435                 440                 445

Phe Lys Ser Ala Met Pro Glu Gly Tyr Val Gln Glu Arg Thr Ile Phe
    450                 455                 460

Phe Lys Asp Asp Gly Asn Tyr Lys Thr Arg Ala Glu Val Lys Phe Glu
465                 470                 475                 480

Gly Asp Thr Leu Val Asn Arg Ile Glu Leu Lys Gly Ile Asp Phe Lys
            485                 490                 495

Glu Asp Gly Asn Ile Leu Gly His Lys Leu Glu Tyr Asn Tyr Asn Ser
        500                 505                 510

His Asn Val Tyr Ile Met Ala Asp Lys Gln Lys Asn Gly Ile Lys Val
    515                 520                 525

Asn Phe Lys Ile Arg His Asn Ile Glu Asp Gly Ser Val Gln Leu Ala
530                 535                 540

Asp His Tyr Gln Gln Asn Thr Pro Ile Gly Asp Gly Pro Val Leu Leu
545                 550                 555                 560

Pro Asp Asn His Tyr Leu Ser Thr Gln Ser Ala Leu Ser Lys Asp Pro
            565                 570                 575

Asn Glu Lys Arg Asp His Met Val Leu Leu Glu Phe Val Thr Ala Ala
        580                 585                 590

Gly Ile Thr Leu Gly Met Asp Glu Leu Tyr Lys
        595                 600

<210> SEQ ID NO 2
<211> LENGTH: 21
<212> TYPE: PRT
<213> ORGANISM: Artificial Sequence
<220> FEATURE:
<223> OTHER INFORMATION: Synthetic Construct

<400> SEQUENCE: 2

Met Ala Leu Pro Val Thr Ala Leu Leu Leu Pro Leu Ala Leu Leu Leu
1               5                   10                  15

His Ala Ala Arg Pro
            20

<210> SEQ ID NO 3
<211> LENGTH: 106
<212> TYPE: PRT
<213> ORGANISM: Artificial Sequence
<220> FEATURE:
<223> OTHER INFORMATION: Synthetic Construct

<400> SEQUENCE: 3

Asp Ile Gln Met Thr Gln Ser Pro Ser Ser Leu Ser Ala Ser Val Gly
1               5                   10                  15

Asp Arg Val Thr Ile Thr Cys Ser Ala Ser Ser Ser Val Ser Tyr Met
            20                  25                  30

Asn Trp Tyr Gln Gln Thr Pro Gly Lys Ala Pro Lys Arg Trp Ile Tyr
        35                  40                  45

Asp Thr Ser Lys Leu Ala Ser Gly Val Pro Ser Arg Phe Ser Gly Ser
    50                  55                  60
```

```
Gly Ser Gly Thr Asp Tyr Thr Phe Thr Ile Ser Ser Leu Gln Pro Glu
 65                  70                  75                  80

Asp Ile Ala Thr Tyr Tyr Cys Gln Gln Trp Ser Ser Asn Pro Phe Thr
                 85                  90                  95

Phe Gly Gln Gly Thr Lys Leu Gln Ile Thr
                100                 105

<210> SEQ ID NO 4
<211> LENGTH: 20
<212> TYPE: PRT
<213> ORGANISM: Artificial Sequence
<220> FEATURE:
<223> OTHER INFORMATION: Synthetic Construct

<400> SEQUENCE: 4

Gly Gly Gly Gly Ser Gly Gly Gly Ser Gly Gly Gly Ser Gly
 1               5                  10                  15

Gly Gly Gly Ser
            20

<210> SEQ ID NO 5
<211> LENGTH: 119
<212> TYPE: PRT
<213> ORGANISM: Artificial Sequence
<220> FEATURE:
<223> OTHER INFORMATION: Synthetic Construct

<400> SEQUENCE: 5

Gln Val Gln Leu Val Gln Ser Gly Gly Gly Val Val Gln Pro Gly Arg
 1               5                  10                  15

Ser Leu Arg Leu Ser Cys Lys Ala Ser Gly Tyr Thr Phe Thr Arg Tyr
                20                  25                  30

Thr Met His Trp Val Arg Gln Ala Pro Gly Lys Gly Leu Glu Trp Ile
            35                  40                  45

Gly Tyr Ile Asn Pro Ser Arg Gly Tyr Thr Asn Tyr Asn Gln Lys Val
    50                  55                  60

Lys Asp Arg Phe Thr Ile Ser Arg Asp Asn Ser Lys Asn Thr Ala Phe
 65                  70                  75                  80

Leu Gln Met Asp Ser Leu Arg Pro Glu Asp Thr Gly Val Tyr Phe Cys
                 85                  90                  95

Ala Arg Tyr Tyr Asp Asp His Tyr Cys Leu Asp Tyr Trp Gly Gln Gly
                100                 105                 110

Thr Pro Val Thr Val Ser Ser
            115

<210> SEQ ID NO 6
<211> LENGTH: 69
<212> TYPE: PRT
<213> ORGANISM: Artificial Sequence
<220> FEATURE:
<223> OTHER INFORMATION: Synthetic Construct

<400> SEQUENCE: 6

Thr Thr Thr Pro Ala Pro Arg Pro Pro Thr Pro Ala Pro Thr Ile Ala
 1               5                  10                  15

Ser Gln Pro Leu Ser Leu Arg Pro Glu Ala Cys Arg Pro Ala Ala Gly
                20                  25                  30

Gly Ala Val His Thr Arg Gly Leu Asp Phe Ala Cys Asp Ile Tyr Ile
            35                  40                  45
```

```
Trp Ala Pro Leu Ala Gly Thr Cys Gly Val Leu Leu Ser Leu Val
    50              55                  60

Ile Thr Leu Tyr Cys
65
```

<210> SEQ ID NO 7
<211> LENGTH: 5
<212> TYPE: PRT
<213> ORGANISM: Artificial Sequence
<220> FEATURE:
<223> OTHER INFORMATION: Synthetic Construct

<400> SEQUENCE: 7

```
Arg Val Lys Phe Ser
1               5
```

<210> SEQ ID NO 8
<211> LENGTH: 24
<212> TYPE: PRT
<213> ORGANISM: Artificial Sequence
<220> FEATURE:
<223> OTHER INFORMATION: Synthetic Construct

<400> SEQUENCE: 8

```
Ser Gly Gly Gly Gly Glu Gly Arg Gly Ser Leu Leu Thr Cys Gly Asp
1               5                   10                  15

Val Glu Glu Asn Pro Gly Pro Arg
            20
```

<210> SEQ ID NO 9
<211> LENGTH: 239
<212> TYPE: PRT
<213> ORGANISM: Artificial Sequence
<220> FEATURE:
<223> OTHER INFORMATION: Synthetic Construct

<400> SEQUENCE: 9

```
Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175
```

-continued

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
            195                 200                 205

Ser Lys Asp Pro Asn Glu Lys Arg Asp His Met Val Leu Leu Glu Phe
210                 215                 220

Val Thr Ala Ala Gly Ile Thr Leu Gly Met Asp Glu Leu Tyr Lys
225                 230                 235

<210> SEQ ID NO 10
<211> LENGTH: 603
<212> TYPE: PRT
<213> ORGANISM: Artificial Sequence
<220> FEATURE:
<223> OTHER INFORMATION: Synthetic Construct

<400> SEQUENCE: 10

Met Ala Leu Pro Val Thr Ala Leu Leu Leu Pro Leu Ala Leu Leu Leu
1               5                   10                  15

His Ala Ala Arg Pro Gln Val Gln Leu Val Gln Ser Gly Gly Gly Val
            20                  25                  30

Val Gln Pro Gly Arg Ser Leu Arg Leu Ser Cys Lys Ala Ser Gly Tyr
        35                  40                  45

Thr Phe Thr Arg Tyr Thr Met His Trp Val Arg Gln Ala Pro Gly Lys
    50                  55                  60

Gly Leu Glu Trp Ile Gly Tyr Ile Asn Pro Ser Arg Gly Tyr Thr Asn
65                  70                  75                  80

Tyr Asn Gln Lys Val Lys Asp Arg Phe Thr Ile Ser Arg Asp Asn Ser
                85                  90                  95

Lys Asn Thr Ala Phe Leu Gln Met Asp Ser Leu Arg Pro Glu Asp Thr
            100                 105                 110

Gly Val Tyr Phe Cys Ala Arg Tyr Tyr Asp Asp His Tyr Cys Leu Asp
        115                 120                 125

Tyr Trp Gly Gln Gly Thr Pro Val Thr Val Ser Ser Gly Gly Gly Gly
    130                 135                 140

Ser Gly Gly Gly Gly Ser Gly Gly Gly Gly Ser Gly Gly Gly Gly Ser
145                 150                 155                 160

Asp Ile Gln Met Thr Gln Ser Pro Ser Ser Leu Ser Ala Ser Val Gly
                165                 170                 175

Asp Arg Val Thr Ile Thr Cys Ser Ala Ser Ser Ser Val Ser Tyr Met
            180                 185                 190

Asn Trp Tyr Gln Gln Thr Pro Gly Lys Ala Pro Lys Arg Trp Ile Tyr
        195                 200                 205

Asp Thr Ser Lys Leu Ala Ser Gly Val Pro Ser Arg Phe Ser Gly Ser
    210                 215                 220

Gly Ser Gly Thr Asp Tyr Thr Phe Thr Ile Ser Ser Leu Gln Pro Glu
225                 230                 235                 240

Asp Ile Ala Thr Tyr Tyr Cys Gln Gln Trp Ser Ser Asn Pro Phe Thr
                245                 250                 255

Phe Gly Gln Gly Thr Lys Leu Gln Ile Thr Thr Thr Thr Pro Ala Pro
            260                 265                 270

Arg Pro Pro Thr Pro Ala Pro Thr Ile Ala Ser Gln Pro Leu Ser Leu
        275                 280                 285

Arg Pro Glu Ala Cys Arg Pro Ala Ala Gly Gly Ala Val His Thr Arg
    290                 295                 300

Gly Leu Asp Phe Ala Cys Asp Ile Tyr Ile Trp Ala Pro Leu Ala Gly
305                 310                 315                 320

Thr Cys Gly Val Leu Leu Ser Leu Val Ile Thr Leu Tyr Cys Arg
            325                 330                 335

Val Lys Phe Ser Ser Gly Gly Gly Glu Gly Arg Gly Ser Leu Leu
            340                 345                 350

Thr Cys Gly Asp Val Glu Glu Asn Pro Gly Pro Arg Met Val Ser Lys
            355                 360                 365

Gly Glu Glu Leu Phe Thr Gly Val Val Pro Ile Leu Val Glu Leu Asp
370                 375                 380

Gly Asp Val Asn Gly His Lys Phe Ser Val Ser Gly Glu Gly Glu Gly
385                 390                 395                 400

Asp Ala Thr Tyr Gly Lys Leu Thr Leu Lys Phe Ile Cys Thr Thr Gly
            405                 410                 415

Lys Leu Pro Val Pro Trp Pro Thr Leu Val Thr Thr Leu Thr Tyr Gly
            420                 425                 430

Val Gln Cys Phe Ser Arg Tyr Pro Asp His Met Lys Gln His Asp Phe
            435                 440                 445

Phe Lys Ser Ala Met Pro Glu Gly Tyr Val Gln Glu Arg Thr Ile Phe
450                 455                 460

Phe Lys Asp Asp Gly Asn Tyr Lys Thr Arg Ala Glu Val Lys Phe Glu
465                 470                 475                 480

Gly Asp Thr Leu Val Asn Arg Ile Glu Leu Lys Gly Ile Asp Phe Lys
            485                 490                 495

Glu Asp Gly Asn Ile Leu Gly His Lys Leu Glu Tyr Asn Tyr Asn Ser
            500                 505                 510

His Asn Val Tyr Ile Met Ala Asp Lys Gln Lys Asn Gly Ile Lys Val
            515                 520                 525

Asn Phe Lys Ile Arg His Asn Ile Glu Asp Gly Ser Val Gln Leu Ala
530                 535                 540

Asp His Tyr Gln Gln Asn Thr Pro Ile Gly Asp Gly Pro Val Leu Leu
545                 550                 555                 560

Pro Asp Asn His Tyr Leu Ser Thr Gln Ser Ala Leu Ser Lys Asp Pro
            565                 570                 575

Asn Glu Lys Arg Asp His Met Val Leu Leu Glu Phe Val Thr Ala Ala
            580                 585                 590

Gly Ile Thr Leu Gly Met Asp Glu Leu Tyr Lys
            595                 600

<210> SEQ ID NO 11
<211> LENGTH: 21
<212> TYPE: PRT
<213> ORGANISM: Artificial Sequence
<220> FEATURE:
<223> OTHER INFORMATION: Synthetic Construct

<400> SEQUENCE: 11

Met Ala Leu Pro Val Thr Ala Leu Leu Leu Pro Leu Ala Leu Leu Leu
1               5                   10                  15

His Ala Ala Arg Pro
            20

<210> SEQ ID NO 12
<211> LENGTH: 119
<212> TYPE: PRT
<213> ORGANISM: Artificial Sequence

```
<220> FEATURE:
<223> OTHER INFORMATION: Synthetic Construct

<400> SEQUENCE: 12

Gln Val Gln Leu Val Gln Ser Gly Gly Gly Val Val Gln Pro Gly Arg
1               5                   10                  15

Ser Leu Arg Leu Ser Cys Lys Ala Ser Gly Tyr Thr Phe Thr Arg Tyr
            20                  25                  30

Thr Met His Trp Val Arg Gln Ala Pro Gly Lys Gly Leu Glu Trp Ile
        35                  40                  45

Gly Tyr Ile Asn Pro Ser Arg Gly Tyr Thr Asn Tyr Asn Gln Lys Val
    50                  55                  60

Lys Asp Arg Phe Thr Ile Ser Arg Asp Asn Ser Lys Asn Thr Ala Phe
65                  70                  75                  80

Leu Gln Met Asp Ser Leu Arg Pro Glu Asp Thr Gly Val Tyr Phe Cys
                85                  90                  95

Ala Arg Tyr Tyr Asp Asp His Tyr Cys Leu Asp Tyr Trp Gly Gln Gly
            100                 105                 110

Thr Pro Val Thr Val Ser Ser
        115

<210> SEQ ID NO 13
<211> LENGTH: 20
<212> TYPE: PRT
<213> ORGANISM: Artificial Sequence
<220> FEATURE:
<223> OTHER INFORMATION: Synthetic Construct

<400> SEQUENCE: 13

Gly Gly Gly Gly Ser Gly Gly Gly Ser Gly Gly Gly Ser Gly
1               5                   10                  15

Gly Gly Gly Ser
            20

<210> SEQ ID NO 14
<211> LENGTH: 106
<212> TYPE: PRT
<213> ORGANISM: Artificial Sequence
<220> FEATURE:
<223> OTHER INFORMATION: Synthetic Construct

<400> SEQUENCE: 14

Asp Ile Gln Met Thr Gln Ser Pro Ser Ser Leu Ser Ala Ser Val Gly
1               5                   10                  15

Asp Arg Val Thr Ile Thr Cys Ser Ala Ser Ser Ser Val Ser Tyr Met
            20                  25                  30

Asn Trp Tyr Gln Gln Thr Pro Gly Lys Ala Pro Lys Arg Trp Ile Tyr
        35                  40                  45

Asp Thr Ser Lys Leu Ala Ser Gly Val Pro Ser Arg Phe Ser Gly Ser
    50                  55                  60

Gly Ser Gly Thr Asp Tyr Thr Phe Thr Ile Ser Ser Leu Gln Pro Glu
65                  70                  75                  80

Asp Ile Ala Thr Tyr Tyr Cys Gln Gln Trp Ser Ser Asn Pro Phe Thr
                85                  90                  95

Phe Gly Gln Gly Thr Lys Leu Gln Ile Thr
            100                 105

<210> SEQ ID NO 15
<211> LENGTH: 69
```

```
<212> TYPE: PRT
<213> ORGANISM: Artificial Sequence
<220> FEATURE:
<223> OTHER INFORMATION: Synthetic Construct

<400> SEQUENCE: 15

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp Ile Tyr Ile
        35                  40                  45

Trp Ala Pro Leu Ala Gly Thr Cys Gly Val Leu Leu Leu Ser Leu Val
    50                  55                  60

Ile Thr Leu Tyr Cys
65

<210> SEQ ID NO 16
<211> LENGTH: 5
<212> TYPE: PRT
<213> ORGANISM: Artificial Sequence
<220> FEATURE:
<223> OTHER INFORMATION: Synthetic Construct

<400> SEQUENCE: 16

Arg Val Lys Phe Ser
1               5

<210> SEQ ID NO 17
<211> LENGTH: 24
<212> TYPE: PRT
<213> ORGANISM: Artificial Sequence
<220> FEATURE:
<223> OTHER INFORMATION: Synthetic Construct

<400> SEQUENCE: 17

Ser Gly Gly Gly Gly Glu Gly Arg Gly Ser Leu Leu Thr Cys Gly Asp
1               5                   10                  15

Val Glu Glu Asn Pro Gly Pro Arg
            20

<210> SEQ ID NO 18
<211> LENGTH: 239
<212> TYPE: PRT
<213> ORGANISM: Artificial Sequence
<220> FEATURE:
<223> OTHER INFORMATION: Synthetic Construct

<400> SEQUENCE: 18

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95
```

```
Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys
225                 230                 235

<210> SEQ ID NO 19
<211> LENGTH: 618
<212> TYPE: PRT
<213> ORGANISM: Artificial Sequence
<220> FEATURE:
<223> OTHER INFORMATION: Synthetic Construct

<400> SEQUENCE: 19

Met Glu Ser Asp Thr Leu Leu Leu Trp Val Leu Leu Leu Trp Val Pro
1               5                   10                  15

Gly Ser Thr Gly Asp Ile Val Leu Thr Gln Ser Pro Ala Ser Leu Ala
            20                  25                  30

Val Ser Leu Gly Gln Arg Ala Thr Ile Ser Cys Arg Ala Ser Glu Ser
        35                  40                  45

Val Glu Tyr Tyr Val Thr Ser Leu Met Gln Trp Tyr Gln Gln Lys Pro
    50                  55                  60

Gly Gln Pro Pro Lys Leu Leu Ile Phe Ala Ala Ser Asn Val Glu Ser
65                  70                  75                  80

Gly Val Pro Ala Arg Phe Ser Gly Ser Gly Ser Gly Thr Asn Phe Ser
                85                  90                  95

Leu Asn Ile His Pro Val Asp Glu Asp Asp Val Ala Met Tyr Phe Cys
            100                 105                 110

Gln Gln Ser Arg Lys Val Pro Tyr Thr Phe Gly Gly Gly Thr Lys Leu
        115                 120                 125

Glu Ile Lys Arg Ala Gly Gly Gly Ser Gly Gly Gly Ser Gly
    130                 135                 140

Gly Gly Ser Gly Gly Gly Gly Ser Leu Ala Gln Val Gln Leu Lys
145                 150                 155                 160

Glu Ser Gly Pro Gly Leu Val Thr Pro Ser Gln Ser Leu Ser Ile Thr
                165                 170                 175

Cys Thr Val Ser Gly Phe Ser Leu Ser Asp Tyr Gly Val His Trp Val
            180                 185                 190

Arg Gln Ser Pro Gly Gln Gly Leu Glu Cys Leu Gly Val Ile Trp Ala
        195                 200                 205

Gly Gly Gly Thr Asn Tyr Asn Ser Ala Leu Met Ser Arg Lys Ser Ile
    210                 215                 220
```

Ser Lys Asp Asn Ser Lys Gly Gln Val Phe Leu Lys Met Lys Ser Leu
225                 230                 235                 240

Gln Ala Asp Asp Thr Ala Val Tyr Tyr Cys Ala Arg Asp Lys Gly Tyr
            245                 250                 255

Ser Tyr Tyr Tyr Ser Met Asp Tyr Trp Gly Gln Gly Thr Ser Val Thr
        260                 265                 270

Val Ser Ser Lys His Leu Cys Pro Ser Pro Leu Phe Pro Gly Pro Ser
    275                 280                 285

Lys Pro Phe Trp Val Leu Val Val Gly Gly Val Leu Ala Cys Tyr
290                 295                 300

Ser Leu Leu Val Thr Val Ala Phe Ile Ile Phe Trp Val Arg Ser Lys
305                 310                 315                 320

Arg Ser Arg Leu Leu His Ser Asp Tyr Met Asn Met Thr Pro Arg Arg
            325                 330                 335

Pro Gly Pro Thr Arg Lys His Tyr Gln Pro Tyr Ala Pro Pro Arg Asp
        340                 345                 350

Phe Ala Ala Tyr Arg Ser Ser Gly Gly Gly Glu Gly Arg Gly Ser
    355                 360                 365

Leu Leu Thr Cys Gly Asp Val Glu Glu Asn Pro Gly Pro Arg Met Val
370                 375                 380

Ser Lys Gly Glu Glu Asp Asn Met Ala Ile Ile Lys Glu Phe Met Arg
385                 390                 395                 400

Phe Lys Val His Met Glu Gly Ser Val Asn Gly His Glu Phe Glu Ile
            405                 410                 415

Glu Gly Glu Gly Glu Gly Arg Pro Tyr Glu Gly Thr Gln Thr Ala Lys
        420                 425                 430

Leu Lys Val Thr Lys Gly Gly Pro Leu Pro Phe Ala Trp Asp Ile Leu
    435                 440                 445

Ser Pro Gln Phe Met Tyr Gly Ser Lys Ala Tyr Val Lys His Pro Ala
450                 455                 460

Asp Ile Pro Asp Tyr Leu Lys Leu Ser Phe Pro Glu Gly Phe Lys Trp
465                 470                 475                 480

Glu Arg Val Met Asn Phe Glu Asp Gly Gly Val Val Thr Val Thr Gln
            485                 490                 495

Asp Ser Ser Leu Gln Asp Gly Glu Phe Ile Tyr Lys Val Lys Leu Arg
        500                 505                 510

Gly Thr Asn Phe Pro Ser Asp Gly Pro Val Met Gln Lys Lys Thr Met
    515                 520                 525

Gly Trp Glu Ala Ser Ser Glu Arg Met Tyr Pro Glu Asp Gly Ala Leu
530                 535                 540

Lys Gly Glu Ile Lys Gln Arg Leu Lys Leu Lys Asp Gly Gly His Tyr
545                 550                 555                 560

Asp Ala Glu Val Lys Thr Thr Tyr Lys Ala Lys Lys Pro Val Gln Leu
            565                 570                 575

Pro Gly Ala Tyr Asn Val Asn Ile Lys Leu Asp Ile Thr Ser His Asn
        580                 585                 590

Glu Asp Tyr Thr Ile Val Glu Gln Tyr Glu Arg Ala Glu Gly Arg His
    595                 600                 605

Ser Thr Gly Gly Met Asp Glu Leu Tyr Lys
610                 615

<210> SEQ ID NO 20
<211> LENGTH: 21
<212> TYPE: PRT

```
<213> ORGANISM: Artificial Sequence
<220> FEATURE:
<223> OTHER INFORMATION: Synthetic Construct

<400> SEQUENCE: 20

Met Ala Leu Pro Val Thr Ala Leu Leu Leu Pro Leu Ala Leu Leu Leu
1               5                   10                  15

His Ala Ala Arg Pro
            20

<210> SEQ ID NO 21
<211> LENGTH: 113
<212> TYPE: PRT
<213> ORGANISM: Artificial Sequence
<220> FEATURE:
<223> OTHER INFORMATION: Synthetic Construct

<400> SEQUENCE: 21

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Glu Tyr Tyr
            20                  25                  30

Val Thr Ser Leu Met Gln Trp Tyr Gln Gln Lys Pro Gly Gln Pro Pro
        35                  40                  45

Lys Leu Leu Ile Phe Ala Ala Ser Asn Val Glu Ser Gly Val Pro Ala
    50                  55                  60

Arg Phe Ser Gly Ser Gly Ser Gly Thr Asn Phe Ser Leu Asn Ile His
65                  70                  75                  80

Pro Val Asp Glu Asp Asp Val Ala Met Tyr Phe Cys Gln Gln Ser Arg
                85                  90                  95

Lys Val Pro Tyr Thr Phe Gly Gly Gly Thr Lys Leu Glu Ile Lys Arg
            100                 105                 110

Ala

<210> SEQ ID NO 22
<211> LENGTH: 20
<212> TYPE: PRT
<213> ORGANISM: Artificial Sequence
<220> FEATURE:
<223> OTHER INFORMATION: Synthetic Construct

<400> SEQUENCE: 22

Gly Gly Gly Gly Ser Gly Gly Gly Ser Gly Gly Gly Ser Gly
1               5                   10                  15

Gly Gly Gly Ser
            20

<210> SEQ ID NO 23
<211> LENGTH: 122
<212> TYPE: PRT
<213> ORGANISM: Artificial Sequence
<220> FEATURE:
<223> OTHER INFORMATION: Synthetic Construct

<400> SEQUENCE: 23

Leu Ala Gln Val Gln Leu Lys Glu Ser Gly Pro Gly Leu Val Thr Pro
1               5                   10                  15

Ser Gln Ser Leu Ser Ile Thr Cys Thr Val Ser Gly Phe Ser Leu Ser
            20                  25                  30

Asp Tyr Gly Val His Trp Val Arg Gln Ser Pro Gly Gln Gly Leu Glu
        35                  40                  45
```

```
Cys Leu Gly Val Ile Trp Ala Gly Gly Thr Asn Tyr Asn Ser Ala
 50                  55                  60

Leu Met Ser Arg Lys Ser Ile Ser Lys Asp Asn Ser Lys Gly Gln Val
 65                  70                  75                  80

Phe Leu Lys Met Lys Ser Leu Gln Ala Asp Asp Thr Ala Val Tyr Tyr
                 85                  90                  95

Cys Ala Arg Asp Lys Gly Tyr Ser Tyr Tyr Tyr Ser Met Asp Tyr Trp
            100                 105                 110

Gly Gln Gly Thr Ser Val Thr Val Ser Ser
            115                 120
```

<210> SEQ ID NO 24
<211> LENGTH: 83
<212> TYPE: PRT
<213> ORGANISM: Artificial Sequence
<220> FEATURE:
<223> OTHER INFORMATION: Synthetic Construct

<400> SEQUENCE: 24

```
Lys His Leu Cys Pro Ser Pro Leu Phe Pro Gly Pro Ser Lys Pro Phe
 1               5                  10                  15

Trp Val Leu Val Val Val Gly Gly Val Leu Ala Cys Tyr Ser Leu Leu
                 20                  25                  30

Val Thr Val Ala Phe Ile Ile Phe Trp Val Arg Ser Lys Arg Ser Arg
             35                  40                  45

Leu Leu His Ser Asp Tyr Met Asn Met Thr Pro Arg Arg Pro Gly Pro
 50                  55                  60

Thr Arg Lys His Tyr Gln Pro Tyr Ala Pro Pro Arg Asp Phe Ala Ala
 65                  70                  75                  80

Tyr Arg Ser
```

<210> SEQ ID NO 25
<211> LENGTH: 24
<212> TYPE: PRT
<213> ORGANISM: Artificial Sequence
<220> FEATURE:
<223> OTHER INFORMATION: Synthetic Construct

<400> SEQUENCE: 25

```
Ser Gly Gly Gly Gly Glu Gly Arg Gly Ser Leu Leu Thr Cys Gly Asp
 1               5                  10                  15

Val Glu Glu Asn Pro Gly Pro Arg
                 20
```

<210> SEQ ID NO 26
<211> LENGTH: 236
<212> TYPE: PRT
<213> ORGANISM: Artificial Sequence
<220> FEATURE:
<223> OTHER INFORMATION: Synthetic Construct

<400> SEQUENCE: 26

```
Met Val Ser Lys Gly Glu Glu Asp Asn Met Ala Ile Ile Lys Glu Phe
 1               5                  10                  15

Met Arg Phe Lys Val His Met Glu Gly Ser Val Asn Gly His Glu Phe
                 20                  25                  30

Glu Ile Glu Gly Glu Gly Glu Gly Arg Pro Tyr Glu Gly Thr Gln Thr
             35                  40                  45
```

```
Ala Lys Leu Lys Val Thr Lys Gly Gly Pro Leu Pro Phe Ala Trp Asp
 50                  55                  60

Ile Leu Ser Pro Gln Phe Met Tyr Gly Ser Lys Ala Tyr Val Lys His
 65                  70                  75                  80

Pro Ala Asp Ile Pro Asp Tyr Leu Lys Leu Ser Phe Pro Glu Gly Phe
                 85                  90                  95

Lys Trp Glu Arg Val Met Asn Phe Glu Asp Gly Gly Val Val Thr Val
            100                 105                 110

Thr Gln Asp Ser Ser Leu Gln Asp Gly Glu Phe Ile Tyr Lys Val Lys
        115                 120                 125

Leu Arg Gly Thr Asn Phe Pro Ser Asp Gly Pro Val Met Gln Lys Lys
    130                 135                 140

Thr Met Gly Trp Glu Ala Ser Ser Glu Arg Met Tyr Pro Glu Asp Gly
145                 150                 155                 160

Ala Leu Lys Gly Glu Ile Lys Gln Arg Leu Lys Leu Lys Asp Gly Gly
                165                 170                 175

His Tyr Asp Ala Glu Val Lys Thr Thr Tyr Lys Ala Lys Lys Pro Val
            180                 185                 190

Gln Leu Pro Gly Ala Tyr Asn Val Asn Ile Lys Leu Asp Ile Thr Ser
        195                 200                 205

His Asn Glu Asp Tyr Thr Ile Val Glu Gln Tyr Glu Arg Ala Glu Gly
    210                 215                 220

Arg His Ser Thr Gly Gly Met Asp Glu Leu Tyr Lys
225                 230                 235

<210> SEQ ID NO 27
<211> LENGTH: 245
<212> TYPE: PRT
<213> ORGANISM: Artificial Sequence
<220> FEATURE:
<223> OTHER INFORMATION: Synthetic Construct

<400> SEQUENCE: 27

Asp Ile Gln Met Thr Gln Ser Pro Ser Ser Leu Ser Ala Ser Val Gly
 1                   5                  10                  15

Asp Arg Val Thr Ile Thr Cys Ser Ala Ser Ser Ser Val Ser Tyr Met
                 20                  25                  30

Asn Trp Tyr Gln Gln Thr Pro Gly Lys Ala Pro Lys Arg Trp Ile Tyr
             35                  40                  45

Asp Thr Ser Lys Leu Ala Ser Gly Val Pro Ser Arg Phe Ser Gly Ser
 50                  55                  60

Gly Ser Gly Thr Asp Tyr Thr Phe Thr Ile Ser Ser Leu Gln Pro Glu
 65                  70                  75                  80

Asp Ile Ala Thr Tyr Tyr Cys Gln Gln Trp Ser Ser Asn Pro Phe Thr
                 85                  90                  95

Phe Gly Gln Gly Thr Lys Leu Gln Ile Thr Gly Gly Gly Gly Ser Gly
            100                 105                 110

Gly Gly Gly Ser Gly Gly Gly Ser Gly Gly Gly Ser Gln Val
        115                 120                 125

Gln Leu Val Gln Ser Gly Gly Val Val Gln Pro Gly Arg Ser Leu
    130                 135                 140

Arg Leu Ser Cys Lys Ala Ser Gly Tyr Thr Phe Thr Arg Tyr Thr Met
145                 150                 155                 160

His Trp Val Arg Gln Ala Pro Gly Lys Gly Leu Glu Trp Ile Gly Tyr
                165                 170                 175
```

Ile Asn Pro Ser Arg Gly Tyr Thr Asn Tyr Asn Gln Lys Val Lys Asp
            180                 185                 190

Arg Phe Thr Ile Ser Arg Asp Asn Ser Lys Asn Thr Ala Phe Leu Gln
        195                 200                 205

Met Asp Ser Leu Arg Pro Glu Asp Thr Gly Val Tyr Phe Cys Ala Arg
210                 215                 220

Tyr Tyr Asp Asp His Tyr Cys Leu Asp Tyr Trp Gly Gln Gly Thr Pro
225                 230                 235                 240

Val Thr Val Ser Ser
                245

<210> SEQ ID NO 28
<211> LENGTH: 106
<212> TYPE: PRT
<213> ORGANISM: Artificial Sequence
<220> FEATURE:
<223> OTHER INFORMATION: Synthetic Construct

<400> SEQUENCE: 28

Asp Ile Gln Met Thr Gln Ser Pro Ser Ser Leu Ser Ala Ser Val Gly
1               5                   10                  15

Asp Arg Val Thr Ile Thr Cys Ser Ala Ser Ser Ser Val Ser Tyr Met
            20                  25                  30

Asn Trp Tyr Gln Gln Thr Pro Gly Lys Ala Pro Lys Arg Trp Ile Tyr
        35                  40                  45

Asp Thr Ser Lys Leu Ala Ser Gly Val Pro Ser Arg Phe Ser Gly Ser
    50                  55                  60

Gly Ser Gly Thr Asp Tyr Thr Phe Thr Ile Ser Ser Leu Gln Pro Glu
65                  70                  75                  80

Asp Ile Ala Thr Tyr Tyr Cys Gln Gln Trp Ser Ser Asn Pro Phe Thr
                85                  90                  95

Phe Gly Gln Gly Thr Lys Leu Gln Ile Thr
            100                 105

<210> SEQ ID NO 29
<211> LENGTH: 20
<212> TYPE: PRT
<213> ORGANISM: Artificial Sequence
<220> FEATURE:
<223> OTHER INFORMATION: Synthetic Construct

<400> SEQUENCE: 29

Gly Gly Gly Gly Ser Gly Gly Gly Ser Gly Gly Gly Ser
1               5                   10                  15

Gly Gly Gly Ser
            20

<210> SEQ ID NO 30
<211> LENGTH: 119
<212> TYPE: PRT
<213> ORGANISM: Artificial Sequence
<220> FEATURE:
<223> OTHER INFORMATION: Synthetic Construct

<400> SEQUENCE: 30

Gln Val Gln Leu Val Gln Ser Gly Gly Gly Val Val Gln Pro Gly Arg
1               5                   10                  15

Ser Leu Arg Leu Ser Cys Lys Ala Ser Gly Tyr Thr Phe Thr Arg Tyr
            20                  25                  30

Thr Met His Trp Val Arg Gln Ala Pro Gly Lys Gly Leu Glu Trp Ile
            35                  40                  45

Gly Tyr Ile Asn Pro Ser Arg Gly Tyr Thr Asn Tyr Asn Gln Lys Val
 50                  55                  60

Lys Asp Arg Phe Thr Ile Ser Arg Asp Asn Ser Lys Asn Thr Ala Phe
 65                  70                  75                  80

Leu Gln Met Asp Ser Leu Arg Pro Glu Asp Thr Gly Val Tyr Phe Cys
                85                  90                  95

Ala Arg Tyr Tyr Asp Asp His Tyr Cys Leu Asp Tyr Trp Gly Gln Gly
            100                 105                 110

Thr Pro Val Thr Val Ser Ser
            115

<210> SEQ ID NO 31
<211> LENGTH: 245
<212> TYPE: PRT
<213> ORGANISM: Artificial Sequence
<220> FEATURE:
<223> OTHER INFORMATION: Synthetic Construct

<400> SEQUENCE: 31

Gln Val Gln Leu Val Gln Ser Gly Gly Gly Val Val Gln Pro Gly Arg
 1               5                   10                  15

Ser Leu Arg Leu Ser Cys Lys Ala Ser Gly Tyr Thr Phe Thr Arg Tyr
            20                  25                  30

Thr Met His Trp Val Arg Gln Ala Pro Gly Lys Gly Leu Glu Trp Ile
            35                  40                  45

Gly Tyr Ile Asn Pro Ser Arg Gly Tyr Thr Asn Tyr Asn Gln Lys Val
 50                  55                  60

Lys Asp Arg Phe Thr Ile Ser Arg Asp Asn Ser Lys Asn Thr Ala Phe
 65                  70                  75                  80

Leu Gln Met Asp Ser Leu Arg Pro Glu Asp Thr Gly Val Tyr Phe Cys
                85                  90                  95

Ala Arg Tyr Tyr Asp Asp His Tyr Cys Leu Asp Tyr Trp Gly Gln Gly
            100                 105                 110

Thr Pro Val Thr Val Ser Ser Gly Gly Gly Ser Gly Gly Gly Gly
            115                 120                 125

Ser Gly Gly Gly Gly Ser Gly Gly Gly Ser Asp Ile Gln Met Thr
130                 135                 140

Gln Ser Pro Ser Ser Leu Ser Ala Ser Val Gly Asp Arg Val Thr Ile
145                 150                 155                 160

Thr Cys Ser Ala Ser Ser Ser Val Ser Tyr Met Asn Trp Tyr Gln Gln
                165                 170                 175

Thr Pro Gly Lys Ala Pro Lys Arg Trp Ile Tyr Asp Thr Ser Lys Leu
            180                 185                 190

Ala Ser Gly Val Pro Ser Arg Phe Ser Gly Ser Gly Ser Gly Thr Asp
        195                 200                 205

Tyr Thr Phe Thr Ile Ser Ser Leu Gln Pro Glu Asp Ile Ala Thr Tyr
    210                 215                 220

Tyr Cys Gln Gln Trp Ser Ser Asn Pro Phe Thr Phe Gly Gln Gly Thr
225                 230                 235                 240

Lys Leu Gln Ile Thr
            245

<210> SEQ ID NO 32
<211> LENGTH: 119

```
<212> TYPE: PRT
<213> ORGANISM: Artificial Sequence
<220> FEATURE:
<223> OTHER INFORMATION: Synthetic Construct

<400> SEQUENCE: 32

Gln Val Gln Leu Val Gln Ser Gly Gly Gly Val Val Gln Pro Gly Arg
1               5                   10                  15

Ser Leu Arg Leu Ser Cys Lys Ala Ser Gly Tyr Thr Phe Thr Arg Tyr
            20                  25                  30

Thr Met His Trp Val Arg Gln Ala Pro Gly Lys Gly Leu Glu Trp Ile
        35                  40                  45

Gly Tyr Ile Asn Pro Ser Arg Gly Tyr Thr Asn Tyr Asn Gln Lys Val
    50                  55                  60

Lys Asp Arg Phe Thr Ile Ser Arg Asp Asn Ser Lys Asn Thr Ala Phe
65                  70                  75                  80

Leu Gln Met Asp Ser Leu Arg Pro Glu Asp Thr Gly Val Tyr Phe Cys
                85                  90                  95

Ala Arg Tyr Tyr Asp Asp His Tyr Cys Leu Asp Tyr Trp Gly Gln Gly
            100                 105                 110

Thr Pro Val Thr Val Ser Ser
            115

<210> SEQ ID NO 33
<211> LENGTH: 20
<212> TYPE: PRT
<213> ORGANISM: Artificial Sequence
<220> FEATURE:
<223> OTHER INFORMATION: Synthetic Construct

<400> SEQUENCE: 33

Gly Gly Gly Gly Ser Gly Gly Gly Ser Gly Gly Gly Gly Ser Gly
1               5                   10                  15

Gly Gly Gly Ser
            20

<210> SEQ ID NO 34
<211> LENGTH: 106
<212> TYPE: PRT
<213> ORGANISM: Artificial Sequence
<220> FEATURE:
<223> OTHER INFORMATION: Synthetic Construct

<400> SEQUENCE: 34

Asp Ile Gln Met Thr Gln Ser Pro Ser Ser Leu Ser Ala Ser Val Gly
1               5                   10                  15

Asp Arg Val Thr Ile Thr Cys Ser Ala Ser Ser Ser Val Ser Tyr Met
            20                  25                  30

Asn Trp Tyr Gln Gln Thr Pro Gly Lys Ala Pro Lys Arg Trp Ile Tyr
        35                  40                  45

Asp Thr Ser Lys Leu Ala Ser Gly Val Pro Ser Arg Phe Ser Gly Ser
    50                  55                  60

Gly Ser Gly Thr Asp Tyr Thr Phe Thr Ile Ser Ser Leu Gln Pro Glu
65                  70                  75                  80

Asp Ile Ala Thr Tyr Tyr Cys Gln Gln Trp Ser Ser Asn Pro Phe Thr
                85                  90                  95

Phe Gly Gln Gly Thr Lys Leu Gln Ile Thr
            100                 105
```

```
<210> SEQ ID NO 35
<211> LENGTH: 255
<212> TYPE: PRT
<213> ORGANISM: Artificial Sequence
<220> FEATURE:
<223> OTHER INFORMATION: Synthetic Construct

<400> SEQUENCE: 35

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Glu Tyr Tyr
            20                  25                  30

Val Thr Ser Leu Met Gln Trp Tyr Gln Gln Lys Pro Gly Gln Pro Pro
        35                  40                  45

Lys Leu Leu Ile Phe Ala Ala Ser Asn Val Glu Ser Gly Val Pro Ala
    50                  55                  60

Arg Phe Ser Gly Ser Gly Ser Gly Thr Asn Phe Ser Leu Asn Ile His
65                  70                  75                  80

Pro Val Asp Glu Asp Asp Val Ala Met Tyr Phe Cys Gln Gln Ser Arg
                85                  90                  95

Lys Val Pro Tyr Thr Phe Gly Gly Gly Thr Lys Leu Glu Ile Lys Arg
            100                 105                 110

Ala Gly Gly Gly Gly Ser Gly Gly Gly Gly Ser Gly Gly Gly Gly Ser
        115                 120                 125

Gly Gly Gly Gly Ser Leu Ala Gln Val Gln Leu Lys Glu Ser Gly Pro
    130                 135                 140

Gly Leu Val Thr Pro Ser Gln Ser Leu Ser Ile Thr Cys Thr Val Ser
145                 150                 155                 160

Gly Phe Ser Leu Ser Asp Tyr Gly Val His Trp Val Arg Gln Ser Pro
                165                 170                 175

Gly Gln Gly Leu Glu Cys Leu Gly Val Ile Trp Ala Gly Gly Gly Thr
            180                 185                 190

Asn Tyr Asn Ser Ala Leu Met Ser Arg Lys Ser Ile Ser Lys Asp Asn
        195                 200                 205

Ser Lys Gly Gln Val Phe Leu Lys Met Lys Ser Leu Gln Ala Asp Asp
    210                 215                 220

Thr Ala Val Tyr Tyr Cys Ala Arg Asp Lys Gly Tyr Ser Tyr Tyr Tyr
225                 230                 235                 240

Ser Met Asp Tyr Trp Gly Gln Gly Thr Ser Val Thr Val Ser Ser
                245                 250                 255

<210> SEQ ID NO 36
<211> LENGTH: 113
<212> TYPE: PRT
<213> ORGANISM: Artificial Sequence
<220> FEATURE:
<223> OTHER INFORMATION: Synthetic Construct

<400> SEQUENCE: 36

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Glu Tyr Tyr
            20                  25                  30

Val Thr Ser Leu Met Gln Trp Tyr Gln Gln Lys Pro Gly Gln Pro Pro
        35                  40                  45
```

```
Lys Leu Leu Ile Phe Ala Ala Ser Asn Val Glu Ser Gly Val Pro Ala
 50                  55                  60

Arg Phe Ser Gly Ser Gly Ser Gly Thr Asn Phe Ser Leu Asn Ile His
 65                  70                  75                  80

Pro Val Asp Glu Asp Asp Val Ala Met Tyr Phe Cys Gln Gln Ser Arg
                 85                  90                  95

Lys Val Pro Tyr Thr Phe Gly Gly Gly Thr Lys Leu Glu Ile Lys Arg
                100                 105                 110

Ala

<210> SEQ ID NO 37
<211> LENGTH: 20
<212> TYPE: PRT
<213> ORGANISM: Artificial Sequence
<220> FEATURE:
<223> OTHER INFORMATION: Synthetic Construct

<400> SEQUENCE: 37

Gly Gly Gly Gly Ser Gly Gly Gly Gly Ser Gly Gly Gly Gly Ser Gly
 1               5                  10                  15

Gly Gly Ser
         20

<210> SEQ ID NO 38
<211> LENGTH: 122
<212> TYPE: PRT
<213> ORGANISM: Artificial Sequence
<220> FEATURE:
<223> OTHER INFORMATION: Synthetic Construct

<400> SEQUENCE: 38

Leu Ala Gln Val Gln Leu Lys Glu Ser Gly Pro Gly Leu Val Thr Pro
 1               5                  10                  15

Ser Gln Ser Leu Ser Ile Thr Cys Thr Val Ser Gly Phe Ser Leu Ser
                 20                  25                  30

Asp Tyr Gly Val His Trp Val Arg Gln Ser Pro Gly Gln Gly Leu Glu
             35                  40                  45

Cys Leu Gly Val Ile Trp Ala Gly Gly Thr Asn Tyr Asn Ser Ala
         50                  55                  60

Leu Met Ser Arg Lys Ser Ile Ser Lys Asp Asn Ser Lys Gly Gln Val
 65                  70                  75                  80

Phe Leu Lys Met Lys Ser Leu Gln Ala Asp Asp Thr Ala Val Tyr Tyr
                 85                  90                  95

Cys Ala Arg Asp Lys Gly Tyr Ser Tyr Tyr Tyr Ser Met Asp Tyr Trp
                100                 105                 110

Gly Gln Gly Thr Ser Val Thr Val Ser Ser
            115                 120
```

UNITED STATES PATENT AND TRADEMARK OFFICE
CERTIFICATE OF CORRECTION

PATENT NO. : 11,613,574 B2
APPLICATION NO. : 16/476592
DATED : March 28, 2023
INVENTOR(S) : Marcela V. Maus et al.

It is certified that error appears in the above-identified patent and that said Letters Patent is hereby corrected as shown below:

In the Specification

At Column 1, Line 1, please replace the paragraph titled CROSS-REFERENCE TO RELATED APPLICATIONS with the following paragraph:
This application is a national stage filing under 35 U.S.C. 371 of international patent application number PCT/US2018/013215, filed January 10, 2018, which claims benefit under 35 U.S.C. § 119(e) of U.S. Provisional Application Nos. 62/444,608, filed January 10, 2017, 62/485,679, filed April 14, 2017, and 62/580,256, filed November 1, 2017, the contents of which are incorporated herein by reference in their entirety.

In the Claims

At Column 79, Line 62, Claim 1:
"binds to CD3binds; and"
Should be:
—binds to CD3e; and—

Signed and Sealed this
Eighth Day of August, 2023

Katherine Kelly Vidal
*Director of the United States Patent and Trademark Office*